United States Patent
Rink et al.

(10) Patent No.: US 6,342,373 B1
(45) Date of Patent: Jan. 29, 2002

(54) PROCESS FOR PREPARING RECOMBINANT EGLIN, PROTEASE INHIBITOR

(75) Inventors: Hans Rink; Manfred Liersch, both of Riehen; Peter Sieber, Reinach; Werner Rittel, Arlesheim; Francois Meyer, Zurich, all of (CH); Ursula Seemüller, München; Hans Fritz, Hohenbrunn, both of (DE); Walter Märki, Möhlin; Sefik Alkan, Reihen, both of (CH)

(73) Assignee: UCP GEN-Pharma AG, Zurich (CH)

( * ) Notice: Subject to any disclaimer, the term of this patent is extended or adjusted under 35 U.S.C. 154(b) by 0 days.

(21) Appl. No.: 07/707,265

(22) Filed: May 24, 1991

Related U.S. Application Data

(63) Continuation of application No. 07/186,828, filed on Apr. 27, 1988, now abandoned, which is a continuation of application No. 06/736,601, filed on May 21, 1985, now abandoned, and a continuation-in-part of application No. 06/673,951, filed on Nov. 21, 1984, now abandoned.

(30) Foreign Application Priority Data

Apr. 13, 1984 (CH) .............................................. 1863/84
Nov. 12, 1984 (CH) .............................................. 5403/84

(51) Int. Cl.$^7$ .............................................. C12N 15/09
(52) U.S. Cl. ..................... 435/69.2; 435/440; 435/471; 435/483; 435/252.3; 435/252.33; 435/254.11; 435/254.21; 435/320.1; 530/300; 530/324; 530/350
(58) Field of Search .............................. 435/69.2, 172.3, 435/252.33, 255, 320.1, 69.1, 440, 471, 483, 252.3, 254.11, 254.21; 530/300, 350, 324

(56) References Cited

U.S. PATENT DOCUMENTS

| | | | | |
|---|---|---|---|---|
| 4,431,739 A | * | 2/1984 | Riggs .................... | 435/252.33 |
| 4,551,433 A | * | 11/1985 | DeBoer ....................... | 935/14 |
| 4,636,489 A | * | 1/1987 | Seemuller et al. ............ | 514/12 |
| 4,664,506 A | * | 5/1987 | Merz et al. .................. | 210/635 |
| 5,079,229 A | * | 1/1992 | Gruttner et al. ............... | 514/12 |

OTHER PUBLICATIONS

Brown, J. Biol. Chem., 254:1447–1449 (1979).
Brown et al., J. Biol. Chem., 251:1009–1014 (1976).
Hallewell et al., Biotechnology, 5:363–366 (1987).
Itakura et al., Science, 198:1056–1063 (1977).
Smyth et al., Nature, 279:252–254 (1979).
Tsunasawa et al., Methods in Enzymology, 106:165–170 (1984).
Tsunasawa et al., J. Biol. Chem., 260:5382–5391 (1985).
Waller et al., Biochem. J., 75:320–326 (1960).
Wold, TIBS, 256–257 (1984).
Narita, Biophys. Acta, 28:184–191 (1958).
Roth et al., J. Biol Chem., 243:3782–3784 (1978).
Goldberg et al., Methods in Enzymology, 80:680–695 (1981).
Wetzel et al., "Synthesis of Polypeptides by Recombinant DNA Methods" in The Peptides, vol. 5 (Academic Press, New York 1983), pp. 1–64.
Winnacker, From Genes to Clones: Introduction to Gene Technology (VCH Publishers 1987), pp. 279–293.
Ross, "Production of Medically Important Polypeptides Using Recombinant DNA Technology" in Insulines, Growth Hormone, and Recombinant DNA Technlolgy, ed. John L. Gueriguian (Raven Press, New York 1981) pp. 33–48.
Marki et al., in Peptides: Structure and Function (Deber et al., ed.) (Pierece Chemical Company 1985) pp. 385–388.
Persson et al., (19850, Eur. J. Biochem., vol. 152, pp 523–527.*
Huang et al., (1987), Biochemistry, vol. 26, pp 8242–8246.*
Knecht et al. (1983), "Sequence Determination of Eglin C," Anla. Biochem, vol. 130, pp 65–71.*
Seemuller et al (1980), "Structure of Elastase Cathepsin G Inhibitor of Leech," Hoppe–Seyler's Z. Phys. Chem., vol. 361, pp 1841–1846.*
Miyanohara et al (1983), "Expression of Hepatitis B Antigen in Yeast," PNAS, vol. 80, pp 1–5.*
R. A. Hallewell et al., Bio–Technology, 5, 363 (1987).
S. Tsunasawa et al., J. Biol. Chem., 260, 5382 (1985).
H. F. Bunn et al., J. Chin. Invest., 49, 1088 (1970).
D. G. Smyth et al., Nature 279, 252 (1979).
G. J. Roth et al., J. Biol. Chem. 253, 3782 (1987).
J. P. Waller et al., Biochem. J. 75, 320 (1960).
Cumberlidge et al., J. Mol. Biol. 131, 169 (1979).
W. Maerki et al., "Inpeptides: Structure and Function", 1985, p. 385.
E. Fink et al., Biol. Chem. Hoppe–Seyler 367, 567 (1986).
M. Jochum et al., Chirurg. Forum f. exp. u. klin. Forsch. (1985), p. 43.
F. N. J. Braun et al., Biol. Chem. Hoppe–Seyler 368, 155 (1987).

* cited by examiner

Primary Examiner—Remy Yucel
(74) Attorney, Agent, or Firm—Oblon, Spivak, McClelland, Maier & Neustadt, P.C.

(57) ABSTRACT

The invention relates to DNA sequences which code an eglin, expression plasmids containing such DNA sequences, hosts transformed with such expression plasmids, novel eglin compounds produced from such transformed hosts, monoclonal antibodies against eglins, hybridoma cells which produce such antibodies, and test kits for immunoassays containing such antibodies, and furthermore the processes for their preparation and a process for the preparation of eglins with the aid of the transformed hosts. The eglins which can be prepared according to the invention have useful pharmacological properties.

3 Claims, 6 Drawing Sheets

PROCESS FOR PREPARING RECOMBINANT EGLIN, PROTEASE INHIBITOR

CROSS REFERENCE

This application is a continuation, of application Ser. No. 07/186,828, filed Apr. 27, 1988, now abandoned which is a continuation of Ser. No. 06/736,601 filed May 21, 1985, abandoned and a continuation-in-part of Ser. No. 06/673,951 filed Nov. 21, 1984, abandoned.

The invention relates to DNA sequences which code protease inhibitors designated eglins, hybrid vectors containing such DNA sequences, hosts transformed by such hybrid vectors, novel potypeptides which have protease inhibitor activity and have been produced by such transformed hosts, processes for the preparation of these DNA sequences, hybrid vectors and transformed hosts, and processes for the preparation of eglins with the aid of the transformed microorganisms.

Two protease inhibitors which are isolated from leeches (*Hirudo medicinalis*) and which are designated eglin B and eglin C are known from German Offenlegungsschrift 2,808, 396. These polypeptides each consist of 70 aminoacids, have a molecular weight of about 8,100 and are potent inhibitors for chymotrypsin, subtilisin, the animal and human granulocyte proteases elastase and cathepsin G and the mast cell protease chymase (1). Trypsin-like proteases are inhibited to a lesser degree.

Eglin C has the following primary structure (2):

ThrGluPheGlySerGluLeuLysSerPheProGluValValGlyLysThrVal
        AspGlnAlaArgGluTyrPheThrLeu-
        HisTyrProGlnTyrAspValTyrPheLeuProGluGly SerProValThr-
        LeuAspLeuArgTyrAsnArgV-
        alArgValPheTyrAsnProGlyThrAsnVal
        ValAsnHisValProHisValGly

In contrast to most of the known proteinase inhibitors, eglin C contains no disulfide bridge and, even for a miniprotein, it proves to be unusually stable towards denaturation by acid, alkali or heat and towards proteolytic degradation. The primary structure of eglin B differs from that of eglin C by replacement of the aminoacid 35, tyrosine, by histidine.

The eglins belong to the most potent inhibitors known at present for human and animal granulocyte elastase, and for human granulocyte cathepsin G and bacterial proteases of the subtilisin type. Uncontrolled or excessive release of these cellular proteases in the organism can intensify an inflammation process and cause tissue degradation by non-specific proteolysis. This is particularly due to the fact that these enzymes, which are responsible for intracellular digestion, have an optimum action in the physiological (neutral to weakly alkaline) medium and are capable of rapidly destroying and inactivating natural tissue substances (for example elastin) and humoral factors (for example blood coagulation factors and complement factors). On the basis of their properties known so far, the eglins are therefore of great interest for use in medical therapy (antiinflammation, antiphlogistics, septic shock, pulmonary emphysema, mucoviscidosis and the like).

Only very small amounts of eglins are formed in leeches (about 16 μg/leech). Isolation and purification of the eglins from leeches is therefore very time-consuming and expensive and cannot be carried out on a commercial scale.

On the basis of the enormous advances in so-called recombinant DNA technology (or genetic engineering), it has recently become possible to prepare the most diverse physiologically active polypeptides using this technology.

The present invention is based on the object of providing, with the aid of genetic engineering means, expression systems which allow the microbial preparation of eglins on an industrial scale. In the present invention, this object is achieved by providing hybrid vectors containing a DNA sequence which codes an eglin and which is regulated by an expression control sequence such that an eglin is expressed in a host transformed by these hybrid vectors.

Preparation of DNA Sequences which Code an Eglin

The invention relates to DNA sequences which code an eglin, for example eglin B and, in particular, eglin C, or a modified eglin, for example modified eglin B or, in particular, modified eglin C, the modification consisting of a shortening of the primary structure of the eglin whilst maintaining the eglin activity, and fragments thereof.

Unless defined more specifically, the general designation "eglins" in the context of the present invention is to be understood as meaning polypeptides with proteinase inhibitor activity, the primary structure of which largely corresponds to the primary structures of eglin B or C (structure homology in general up to 80%), but which can also be modified N-terminally, for example Nα-acetylated, $N^\alpha$-methionylated or $N_\alpha$-acetylmethionylated on the threonine.

In the case of modified eglins, the modification preferably consists of a shortening of the primary structure of the natural eglins, for example by 1 to 10, in particular 1 to 6, aminoacid units at the N-terminus and/or by 1 to 6, in particular 2, aminoacid units at the C-terminus, derivatives modified on the N-terminus, for example acetylated and methionylated or N-acetylmethionylated derivatives, also being included here.

The invention furthermore relates to processes for the preparation of DNA sequences which code an eglin, for example eglin B and, in particular, eglin C, or a modified eglin, for example modified eglin B or, in particular, modified eglin C, and of fragments thereof, which comprises isolating the eglin structure geno from genomic leech-DNA, or preparing a complementary double-stranded eglin-DNA (eglin-ds cDNA) from eglin-mRNA, and, for the preparation of DNA sequences which code a modified eglin, treating the genomic eglin structure gene or the eglin-ds cDNA with suitable nucleases, or which comprises preparing a corresponding (modified) eglin structure gene or fragments thereof by means of chemical and enzymatic processes.

Genomic eglin-DNA and eglin-ds cDNA are obtained, for example, by methods which are known per se. Thus, genomic eglin-DNA is obtained, for example, from a leech gene bank containing the eglin gene, by cloning the leech-DNA fragments in a microorganism and identifying clones containing the eglin-DNA, for example by colony hybridisation using a radioactively labelled eglin-DNA-specific oligodeoxynucleotide containing at least 15, preferably 15 to 30, deoxynucleotides. The DNA fragments thus obtained as a rule contain, in addition to the eglin gene, further undesired DNA constituents, which can be detached by treatment with suitable exo- or endonucleases.

Double-stranded eglin-cDNA can be prepared, for example, by obtaining mRNA from suitable leech cells, preferably those which have been induced into eglin formation, enriching the eglin-mRNA in the resulting mRNA mixture in a manner which is known per se, using the mRNA as a template for the preparation of single-stranded cDNA, synthesising the ds cDNA therefrom with the aid of an RNA-dependent DNA-polymerase and cloning this in a suitable vector. Clones containing the eglin-cDNA are identified, for example, as described above, by colony hybridisation using a radioactively labelled eglin-DNA-specific oligodeoxynucleotide.

To prepare DNA sequences which code modified eglins, the genomic eglin-DNA or eglin-cDNA obtainable can be treated with suitable exo- and/or endo-nucleases which detach the DNA sections coding the N- or C-terminal eglin aminoacids.

The genomic eglin-DNA obtained in this manner or the eglin-cDNA are preferably linked on the 5'- and on the 3'-end with chemically synthesised adapter oligodeoxynucleotides which contain the recognition sequence for one or more restriction endonuclease(s) and thus facilitate the incorporation into suitable vectors. In addition, the adapter molecule for the 5'-end of the eglin-DNA or -cDNA must also contain the translation start signat (ATG). The translation start signal must be located such that it is followed directly by the codon for the first aminoacid of the eglin.

Since the structure of the natural eglin gene is unknown and the chemical synthesis of an eglin gene offers advantages, especially in respect of time, on the basis of modern synthesis possibilities, chemical synthesis is a preferred embodiment of the present invention.

Chemical Synthesis of an Eglin Gene

The invention particularly relates to a process for the preparation of a structure gene for an eglin or for a modified eglin or of fragments thereof, which comprises chemically synthesising segments of the coding and complementary strand of an eglin gene or modified eglin gene and enzymatically converting the segments obtainable into a structure gene of the eglin or the modified eglin or into fragments thereof.

The invention furthermore relates to double-stranded DNAs which code eglins, for example eglin B or eglin C, modified eglins, for example modified eglin B or modified eglin C, or fragments thereof.

In addition to the codons for the eglins or modified eglins, the DNAs according to the invention contain translation start signals and translation stop signals which make expression in suitable host cells, for example in *E. coli*, possible, and furthermore nucleotide sequences at the ends which are suitable for incorporation into a vector.

In a preferred embodiment of the invention, the DNA comprises, at the 5'-end, a nucleotide sequence which can be cleaved by a restriction enzyme, followed by the translation start signal, codons for an eglin or for a modified eglin, which, if appropriate, make possible cleaving by a restriction enzyme at one or more sites, a translation stop signal and, at the 3'-end, a nucleotide sequence which can be cleaved by a restriction enzyme. Examples of restriction enzymes which can be used according to the invention are EcoRI, BamHI, HpaII, PstI, AvaI and HindIII.

The invention particularly relates to an eglin-coding, double-stranded DNA consisting of a nucleotide sequence of the formula I and the complementary nucleotide sequence

|  | Met | B |  |  |  |  |  |  |  | (I) |
|---|---|---|---|---|---|---|---|---|---|---|
| 5'(X)$_n$ | ATG | D |  |  |  |  |  |  |  |  |
| Pro | Glu | Val | Val | Gly | Lys | Thr | Val | Asp | Gln |  |
| CCX | GAM | GTX | GTX | GGX | AAM | ACX | GTX | GAY | CAM |  |
| Ala | Arg | Glu | Tyr | Phe | Thr | Leu | His | Tyr | Pro |  |
| GCX | LGN | GAM | TAY | TTY | ACX | YTZ | CAY | TAY | CCX |  |
| Gln | Tyr | Asp | Val | W | Phe | Leu | Pro | Glu | Gly |  |
| CAM | TAY | GAY | GTX | YAY | TTY | YTZ | CCX | GAM | GGX |  |
| Ser | Pro | Val | Thr | Leu | Asp | Leu | Arg | Tyr | Asn |  |
| QRS | CCX | GTX | ACX | YTZ | GAY | YTZ | LGN | TAY | AAY |  |

-continued

| Arg | Val | Arg | Val | Phe | Tyr | Asn | Pro | Gly | Thr |
|---|---|---|---|---|---|---|---|---|---|
| LGN | GTX | LGN | GTX | TTY | TAY | AAY | CCX | GGX | ACX |
| Asn | Val | Val | Asn | B' | NON |  |  |  |  |
| AAY | GTX | GTX | AAY | D' |  | TMK | (X)$_m$3' |  |  | in which the nucleotide sequence is shown starting with the 5'-end and, for better understanding, the amino acids coded by each triplet are given, and in which D is a direct bond or a nucleotide sequence which codes N-terminal aminoacids of the eglin, and B is a direct bond or the corresponding N-terminal aminoacids chosen from the group comprising

| Ser | Phe | Leu | Lys | Ser | Phe | Ser | Glu | Leu | Lys |
|---|---|---|---|---|---|---|---|---|---|
| QRS | TTY, | YTZ | AAM | QRS | TTY, | QRS | GAM | YTZ | AAM |
| Ser | Phe | Phe | Gly | Ser | Glu | Leu | Lys | Ser | Phe |
| QRS | TTY, | TTY | GGX | QRS | GAM | YTZ | AAM | QRS | TTY |
| or |  |  |  |  |  |  |  |  |  |
| Thr | Glu | Phe | Gly | Ser | Glu | Leu | Lys | Ser | Phe |
| ACX | GAM | TTY | GGX | QRS | GAM | YTZ | AAM | QRS | TTY | and D' is a direct bond or a nucleotide sequence which codes C-terminal aminoacids of the eglin, and B' is a direct bond or the corresponding C-terminal aminoacids chosen from the group comprising

| His | Val | His | Val | Pro | His |  |
|---|---|---|---|---|---|---|
| CAY | GTX | CAY | GTX | CCX | CAY |  |
|  |  |  |  |  |  | and |
| His | Val | Pro | His | Val | Gly |  |
| CAY | GTX | CCX | CAY | GTX | GGX |  | and in which A is deoxyadenosyl, T is thymidyl, G is deoxyguanosyl, C is deoxycytidyl, X is A, T, C or G, Y is T or C, Z is A, T, C or G, if Y=C, or Z is A or G, if Y=T, Q is T or A, R is C, and S is A, T, C or G, if Q=T, or R is G and S is T or C, if Q=A, M is A or G, L is A or C, N is A or G, if L=A, or N is A, T, C or G, if L=C, K is A or G, if M=A, or K is A, if M=G, W is Tyr or His, and (X)$_n$ and (X)$_m$ are each any nucleotide sequences with n and m greater than 3 and less than 100, in particular greater than 5 and less than 12, which can be recognised and cleaved by a restriction enzyme, and fragments of such a double-stranded DNA of the formula I.

The invention particularly relates to an eglin-coding double-stranded DNA of the formula I in which D is a nucleotide sequence selected from the group comprising YTZ AAM QRS TTY, QRS GAM YTZ AAM QRS TTY and ACX GAM TTY GGX QRS GAM YTZ AAM QRS TTY, and D' is the nucleotide sequence of the formula CAY GTX CCX CAY GTX GGX, and the other symbols are as defined under formula I.

The invention especially relates to an eglin-coding double-stranded DNA of the formula I, in which D is the nucleotide sequence ACX GAM TTY GGX QRS GAM YTZ AAM QRS TTY and D' is the nucleotide sequence CAY GTX CCX CAY GTX GGX, and the remaining symbols are as defined under formula I.

In a preferred embodiment, the DNA sequence contains, at the 5'-end, a nucleotide sequence which can be cleaved by EcoRI, and, in the middle, a nucleotide sequence which can be cleaved by HpaII, and, at the 3'-end, a nucleotide sequence which can be cleaved by BamHI.

The invention especially relates to a double-stranded DNA containing triplets which are preferred by *E. coli* and which code the aminoacids of eglins or modified eglins. Such triplets are: for glycine (Gly): GGT; alanine (Ala): GCT; valine (Val): GTT; leucine (Leu): CTG; serine (Ser): TCT; threonine (Thr): ACT; phenylalanine (Phe): TTC; tyrosine (Tyr): TAC; Methionine (Met): ATG; asparaginic acid (Asp): GAC; glutamic acid (Glu): GAA; lysine (Lys): AAA; arginine (Arg): CGT; histidine (His): CAT; proline (Pro): CCG; glutamine (Gln): CAG; and asparagine (Asn): AAC.

In the present invention, the codon TTT is also used for phenylalanine and CCA or CCT is used for proline, so that, besides the cleavage site for EcoRI at the 5'-end and for BamHI at the 3'-end and a cleavage site for HpaII, no other cleavage sites are present for the restriction enzymes mentioned. The preferred stop signal (NON) is the codon TAG.

A preferred embodiment of a gene for eglin C in the manner shown above is the DNA of the formula IIa

```
        MetThrGluPheGlySerGluLeuLysSerPheProGluValValGlyLysThrVal    (IIa)
CTGGAATTCATGACTGAATTTGGTTCTGAACTGAAATCTTTCCCAGAAGTTGTTGGTAAAACTGTT
GACCTTAAGTACTGACTTAAACCAAGACTTGACTTTAGAAAGGGTCTTCAACAACCATTTTGACAA
    (EcoRI)

AspGlnAlaArgGluTyrPheThrLeuHisTyrProGlnTyrAspValTyrPheLeuProGluGly
GACCAGGCTCGTGAATACTTCACTCTGCATTACCCGCAGTACGACGTTTACTTCCTGCCGGAAGGT
CTGGTCCGAGCACTTATGAAGTGAGACGTAATGGGCGTCATGCTGCAAATGAAGGACGGCCTTCCA
                                                              (HpaII)

SerProValThrLeuAspLeuArgTyrAsnArgValArgValPheTyrAsnProGlyThrAsnVal
TCTCCTGTTACTCTGGACCTGCGTTACAACCGTGTTCGTGTTTTCTACAACCCAGGTACTAACGTT
AGAGGACAATGAGACCTGGACGCAATGTTGGCACAAGCACAAAAGATGTTGGGTCCATGATTGCAA

ValAsnHisValProHisValGlyNON
GTTAACCATGTTCCGCATGTTGGTTAGGATCCTG
CAATTGGTACAAGGCGTACAACCAATCCTAGGAC
                 (BamHI)
``` a preferred embodiment of a gene for eglin B is the DNA of the formula IIb

```
        MetThrGluPheGlySerGluLeuLysSerPheProGluValValGlyLysThrVal    (IIb)
CTGGAATTCATGACTGAATTTGGTTCTGAACTGAAATCTTTCCCAGAAGTTGTTGGTAAAACTGTT
GACCTTAAGTACTGACTTAAACCAAGACTTGACTTTAGAAAGGGTCTTCAACAACCATTTTGACAA
    (EcoRI)

AspGlnAlaArgGluTyrPheThrLeuHisTyrProGlnTyrAspValHisPheLeuProGluGly
GACCAGGCTCGTGAATACTTCACTCTGCATTACCCGCAGTACGACGTTCATTTCCTGCCGGAAGGT
CTGGTCCGAGCACTTATGAAGTGAGACGTAATGGGCGTCATGCTGCAAGTAAAGGACGGCCTTCCA
                                                              (HpaII)

SerProValThrLeuAspLeuArgTyrAsnArgValArgValPheTyrAsnProGlyThrAsnVal
TCTCCTGTTACTCTGGACCTGCGTTACAACCGTGTTCGTGTTTTCTACAACCCAGGTACTAACGTT
AGAGGACAATGAGACCTGGACGCAATGTTGGCACAAGCACAAAAGATGTTGGGTCCATGATTGCAA

ValAsnHisValProHisValGlyNON
GTTAACCATGTTCCGCATGTTGGTTAGGATCCTG
CAATTGGTACAAGGCGTACAACCAATCCTAGGAC
                 (BamHI)
``` and preferred embodiments of genes for modified (N-terminally shortened) eglin C polypeptides are the DNAs of the formulae IIc and IId

```
        MetSerGluLeuLysSerPheProGluValValGlyLysThrVal    (IIc)
CTGGAATTCATGTCTGAACTGAAATCTTTCCCAGAAGTTGTTGGTAAAACTGTT
GACCTTAAGTACAGACTTGACTTTAGAAAGGGTCTTCAACAACCATTTTGACAA
    (EcoRI)
```

```
                                                       -continued
AspGlnAlaArgGluTyrPheThrLeuHisTyrProGlnTyrAspValTyrPheLeuProGluCly
GACCAGGCTCGTGAATACTTCACTCTGCATTACCCGCAGTACGACGTTTACTTCCTGCCGGAAGGT
CTGGTCCGAGCACTTATGAAGTGAGACGTAATGGGCGTCATGCTGCAAATGAAGGACGGCCTTCCA
                                                        (HpaII)

SerProValThrLeuAspLeuArgTyrAsnArgValArgValPheTyrAsnProGlyThrAsnVal
TCTCCTGTTACTCTGGACCTGCGTTACAACCGTGTTCGTGTTTTCTACAACCCAGGTACTAACGTT
AGAGGACAATGAGACCTGGACGCAATGTTGGCACAAGCACAAAAGATGTTGGGTCCATGATTGCAA

ValAsnHisValProHisValGlyNON
GTTAACCATGTTCCGCATGTTGGTTAGGATCCTG
CAATTGGTACAAGGCGTACAACCAATCCTAGGAC
                        (BamHI)

and

MetLeuLysSerPheProGluValValGlyLysThrVal                       (IId)
CTGGAATTCATGCTGAAATCTTTCCCAGAAGTTGTTGGTAAAACTGTT
GACCTTAAGTACGACTTTAGAAAGGGTCTTCAACAACCATTTTGACAA
     (EcoRI)

AspGlnAlaArgGluTyrPheThrLeuHisTyrProGlnTyrAspValTyrPheLeuProGluGly
GACCAGGCTCGTGAATACTTCACTCTGCATTACCCGCAGTACGACGTTTACTTCCTGCCGGAAGGT
CTGGTCCGAGCACTTATGAAGTGAGACGTAATGGGCGTCATGCTGCAAATGAAGGACGGCCTTCCA
                                                         (HpaII)

SerProValThrLeuAspLeuArgTyrAsnArgValArgValPheTyrAsnProGlyThrAsnVal
TCTCCTGTTACTCTGGACCTGCGTTACAACCGTGTTCGTGTTTTCTACAACCCAGGTACTAACGTT
AGAGGACAATGAGACCTGGACGCAATGTTGGCACAAGCACAAAAGATGTTGGGTCCATGATTGCAA

ValAsnHisValProHisValGlyNON
GTTAACCATGTTCCGCATGTTGGTTAGGATCCTG
CAATTGGTACAAGGCGTACAACCAATCCTAGGAC
                        (BamHI)
``` in which A, T, G and C are as defined under formula I and, for better understanding, the aminoacids coded by each triplet and the cleavage sites for the restriction enzymes are given.

The invention furthermore relates to double-stranded DNA fragments of eglin genes, the ends of which can be cleaved by restriction enzymes, and which can be brought together to form complete eglin or modified eglin genes.

Such double-stranded DNA fragments of eglin genes have, in particular, 30 to 70 base pairs.

The invention relates, for example, to the DNA fragments of the formula IIIa [$F_1$(C)], the DNA of the formula IIIa' [$F_1$(C')], the DNA of the formula IIIa" [$F_1$(C")], the DNA of the formula IIIb [$F_1$(B)] and the DNA of the formula IV ($F_2$):

```
         MetThrGluPheGlySerGluLeuLysSerPheProGluValValGlyLysThrVal   (IIIa)
CTGGAATTCATGACTGAATTTGGTTCTGAACTGAAATCTTTCCCAGAAGTTGTTGGTAAAACTGTT
GACCTTAAGTACTGACTTAAACCAAGACTTGACTTTAGAAAGGGTCTTCAACAACCATTTTGACAA

AspGlnAlaArgGluTyrPheThrLeuHisTyrProGlnTyrAspValTyrPheLeuPro
GACCAGGCTCGTGAATACTTCACTCTGCATTACCCGCAGTACGACGTTTACTTCCTGCCGG
CTGGTCCGAGCACTTATGAAGTGAGACGTAATGGGCGTCATGCTGCAAATGAAGGACGGCC
                           F1(C)

MetSerGluLeuLysSerPheProGluValValGlyLysThrVal               (IIIa')
CTGGAATTCATGTCTGAACTGAAATCTTTCCCAGAAGTTGTTGGTAAAACTGTT
GACCTTAAGTACAGACTTGACTTTAGAAAGGGTCTTCAACAACCATTTTGACAA

AspGlnAlaArgGluTyrPheThrLeuHisTyrProGlnTyrAspValTyrPheLeuPro
GACCAGGCTCGTGAATACTTCACTCTGCATTACCCGCAGTACGACGTTTACTTCCTGCCGG
CTGGTCCGAGCACTTATGAAGTGAGACGTAATGGGCGTCATGCTGCAAATGAAGGACGGCG
                           F1(C')

MetLeuLysSerPheProGluValValGlyLysThrVal                     (IIIa")
CTGGAATTCATGCTGAAATCTTTCCCAGAAGTTGTTGGTAAAACTGTT
GACCTTAAGTACGACTTTAGAAAGGGTCTTCAACAACCATTTTGACAA

AspGlnAlaArgGluTyrPheThrLeuHisTyrProGlnTyrAspValTyrPheLeuPro
GACCAGGCTCGTGAATACTTCACTCTGCATTACCCGCAGTACGACGTTTACTTCCTGCCGG
CTGGTCCGAGCACTTATGAAGTGAGACGTAATGGGCGTCATGCTGCAAATGAAGGACGGCC
                           F1(C")

MetThrGluPheGlySerGluLeuLysSerPheProGluValValGlyLysThrVal   (IIIb)
CTGGAATTCATGACTGAATTTGGTTCTGAACTGAAATCTTTCCCAGAAGTTGTTGGTAAAACTGTT
GACCTTAAGTACTGACTTAAACCAAGACTTGACTTTAGAAAGGGTCTTCAACAACCATTTTGACAA
```

-continued

```
AspGlnAlaArgGluTyrPheThrLeuHisTyrProGlnTyrAspValHisPheLeuPro
GACCAGGCTCGTGAATACTTCACTCTGCATTACCCGCAGTACGACGTTCATTTCCTGCCGG
CTGGTCCGAGCACTTATGAAGTGAGACGTAATGGGCGTCATGCTGCAAGTAAAGGACGGCC
                        F₁(B)
``` and

```
ProGlyGlySerProValThrLeuAspLeuArgTyrAsnArgValArgValPheTyrAsnProGly    (IV)
CCGGAAGGTTCTCCTGTTACTCTGGACCTGCGTTACAACCGTGTTCGTGTTTCTACAACCCAGGT
GGCCTTCCAAGAGGACAATGAGACCTGGACGCAATGTTGGCACAAGCACAAAAGATGTTGGGTCCA

ThrAsnValValAsnHisValProHisValGlyNON
ACTAACGTTGTTAACCATGTTCCGCATGTTGGTTAGGATCCTG
TGATTGCAACAATTGGTACAAGGCGTACAACCAATCCTAGGAC
                        F₂
```

The invention also relates to single-stranded DNA fragments of eglin and modified eglin genes, in particular those which can be joined together by chemical and/or enzymatic methods to give eglin or modified eglin genes. The invention particularly relates to single-stranded DNA fragments with more than twenty nucleotides, in particuLar with 20 to 70 nucleotides.

The invention above all relates to the single-stranded and double-stranded DNA fragments described in the examples.

Methods for the synthesis of DNA have been presented in summary form by S. A. Narang (11). The known synthesis techniques allow the preparation of polynucleotides towards 20 bases in length, in good yield, high purity and in a relatively short time. Suitably protected nucleotides are linked with one another by the phosphodiester method (12), or the even more efficient phosphotriester method (13) or phosphite triester method (14). Simplification of the synthesis of the oligonucleotides and polynucleotides is made possible by the solid phase method, in which the nucleotide chains are bound to a suitable polymer. Itakura et at. (15) use trinucleotides linked by the phosphotriester method in the solid phase synthesis, instead of individual nucleotides, and these can thus be condensed, in a short time and with good yields, for example, to give a polynucleotide with 31 bases. The actual double-stranded DNA can be built up enzymatically from chemically prepared short segments. For this, Khorana et at. (16) use overlapping polynucleotide sequences from both DNA strands, which are held together in the correct arrangement by base-pairing and are then chemically linked by the enzyme DNA-ligase. Another possibility comprises incubating in each case one polynucleotide sequence from the two DNA strands with a short overlapping segment in the presence of the four required deoxynucleoside triphosphates with a DNA-polymerase, for example DNA-polymerase I, a Klenow fragment of polymerase I or $T_4$ DNA-polymerase, or with AMV (avian myeloblastosis virus) reverse transcriptase. The two polynucleotide sequences are thereby held together in the correct arrangement by base-pairing and are supplemented with the required nucleotides by the enzyme to give a complete double-stranded DNA (17). Itakura et al. (18) describe how, on the basis of this principle, a segment 132 base pairs long of the human leucocyte interferon $\alpha_2$-gene can be built up in the presence of DNA-polymerase I (Klenow fragment) from 4 chemically synthesised fragments 39 to 42 bases in length, a 40% saving in chemical synthesis in comparison with the method which uses only ligase being achieved.

The present invention particularly relates to a process for the preparation of DNAs which code eglins or modified eglins which are suitable for expression in host cells and the ends of which enable incorporation into vectors, and of fragments thereof, which comprises a) bonding a suitably protected deoxynucleoside to a solid carrier, b) preparing suitably protected di-, tri- or tetra-nucleotides by the phosphotriester or phosphite method, c) linking a deoxynucleoside or oligodeoxynucleotide bound to the carrier with suitably protected mononucleotides or di-, tri- or tetranucleotides (the latter prepared according to b)) by the phosphotriester or phosphite method, d) detaching carrier-bound oligodeoxynucleotides between about 20 and about 70 bases in length obtainable according to c) from the carrier, if appropriate purifying them, freeing them from protective groups and phosphorylating the free 5'-terminal hydroxyl groups, el) fusing 2 oligodeoxynucleotides each of about 20 to about 70 bases in length from the coding and the complementary strand and with at least 3, preferably 8 to 15, overlapping base pairs and supplementing them with a DNA-polymerase in the presence of the four deoxynucleoside triphosphates to give double-stranded DNA segments (fragments of the eglin or modified eglin gene), and, if appropriate, linking 2 double-stranded DNA segments with suitable ends phosphorylated according to d), with a ligase to give the structure gene of the eglin or of the modified eglin, or subcloning into suitable vectors 2 obtainable double-stranded DNA segments, and then phosphorytating according to d) and linking with a ligase to give the structure gene of the eglin or modified eglin, or e2) alternatively fusing in each case 2 oligodeoxynucleotides from the coding and complementary strand of, for example, 20 to 70 bases in length and with in each case at least 3, preferably 8 to 15, overlapping base pairs, making up with a DNA polymerase in the presence of the four deoxynucleoside triphosphates and linking with ligase to give the structure gene of the eglin or the modified eglin.

The process according to the invention is known per se, but makes the preparation of eglin-coding DNAs possible only by suitable combination of the conditions and improvements essential to the invention.

A large number of solid carrier materials, such as polystyrene crosslinked in various ways and with various swelling capacities, polyacrylamides, polyacrylamide copolymers polyamides absorbed onto inorganic material, such as kiesilguhr, silica get or alox, or functionalised silanes, can be used in step a). In a preferred embodiment of the invention, crosslinked polystyrenes which are linked via "spacers", such as alkylene groups with 2 to 12 C atoms interrupted by 1 to 5 polar divalent functional groups, such as imino, oxo, thio, oxocarbonyl or amidocarbonyl, with the 5'-OH group of suitably protected deoxynucleosides in a manner which is known per se are used as the solid carrier materials. The reaction of nucleosides of the formula V which are protected in the 5'-position and, if appropriate, in the base part and in which $R^1$ is a protective group which can be detached by acid, such as a triarylmethyl protective group, for example a 4-methoxytrityl or 4,4'-dimethoxytrityl group, or a tri-lower alkyl-silyl protective group, for example a tert.-butyldimethylsilyl group, and in which B is a protected or unprotected base chosen from thymyl, cytosyl, adenyl or guanyl, with succinic anhydride, in the presence or absence of bases, such as pyridine, triethylamine or dimethylaminopyridine, followed by reaction with aminomethylated polystyrene, crosslinked by 0.5 to 2% of divinylbenzene, with the aid of reagents which activate the carboxylic acid radical, preferably N-hydroxysuccinimide, or p-nitrophenol and dehydrating agents, such as carbodiimides, for example dicyclohexylcarbodiimide, is particularly preferred (equation 1).

The reaction is carried out in an inert, non-protic solvent, for example pyridine, tetrahydrofuran, dioxane, ethyl acetate, chloroform, methylene chloride, dimethylformamide or diethylacetamide, or in mixtures thereof, at room temperature or slightly elevated or reduced temperature, for example in a temperature range from about $-10°$ C. to about $50°$ C., preferably at room temperature, the reaction in the presence of the dehydrating agent also being carried out at lower temperatures, for example at about $0°$ C.

Equation 1

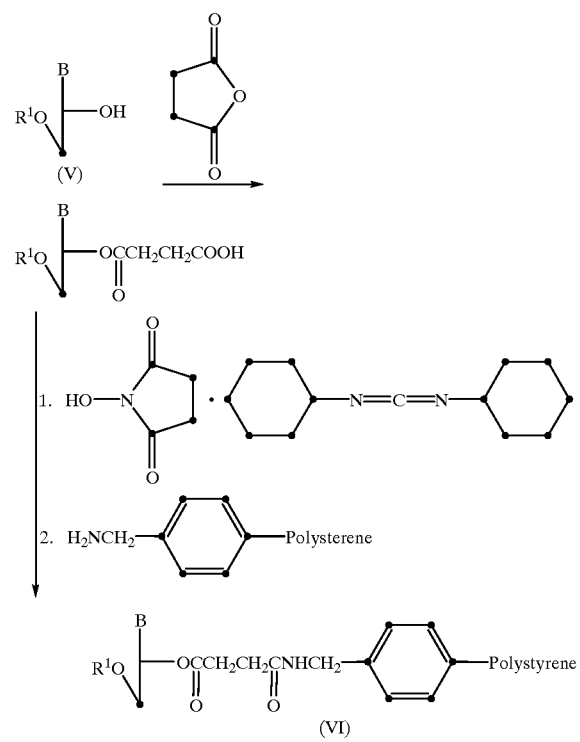

In the preparation, according to the invention, of di-, tri- or tetra-nucleotides in step b), nucleosides of the formula V which are protected in the 5'-position and, if appropriate, in the base part and in which $R^1$ and B are as defined above are reacted with activated phosphorus esters of the formula VII, in which $X^1$ and $X^2$ independently of one another are hydroxyl or salts derived therefrom, halogen, imidazolyl, 1,2,4-triazol-1-yl, tetrazolyl or 1-benzotriazolyloxy, and $X^2$ additionally can also be 2-cyanoethoxy, 2-trihalogenoethoxy, 2-arylsulfonylethoxy, 2-lower alkylthioethoxy, 2-arylthioethoxy or 2-(4-nitrophenyl)-ethoxy and $R^2$ is a protective group which can be detached by a base or nucleophiles, such as ammonium hydroxide, thiophenolate or an arylaldoximate, such as phenyl which is unsubstituted or substituted by halogen, nitro and/or lower alkyl, methyl or benzyl which is unsubstituted or substituted by nitro, or a protective group which can be detached by metal ions, such as 8-quinolyl or 5-chloro-8-quinolyl, in the presence or absence of dehydrating agents or in the presence or absence of bases.

A compound of the formula VIII formed in this manner, in which $R^1$, $X^2$ and $R^2$ are as defined above, is subsequently first reacted, if appropriate, with a 2-substituted ethanol which converts the radical $X^2$ into a group $OR^3$, in which $R^3$ is cyanoethyl, 2-trihalogenoethyl, 2-arylsulfonylethyl, 2-lower alkylthioethyl, 2-arylthioethyl or 2-(4-nitrophenyl)-ethyl, the protective group $R^1$ is then detached and the compound of the formula IX prepared in this manner is reacted with another compound of the formula VIII in the presence or absence of dehydrating agents or in the presence or absence of bases, to give a dinucleotide X (equation 2). If appropriate, a compound of the formula VIII is converted into another compound of the formula VIII, in which $X^2$ is hydroxyl or salts derived therefrom, by reaction with bases and water.

The reactions are carried out in one of the abovementioned inert solvents at room temperature or slightly elevated or reduced temperature, for example at room temperature.

The protective group $R^1$ is detached, for example, with the aid of acids, such as mineral acids, for example hydrochloric acid or sulfuric acid, carboxylic acids, for example acetic acid, trichloroacetic acid or formic acid, sulfonic acids, for example methanesulfonic or p-toluenesulfonic acid, or, in particular, Lewis acids, for example zinc chloride, zinc bromide, aluminium chloride, dialkylaluminium halides, for example dibutyl- or diethyl-aluminium chloride, or boron trifluoride, at $10°$ C. to $50°$ C., in particular at room temperature. If a dialkylaluminium halide is used, the detachment is carried out in a lipophilic solvent, in particular in toluene, and if one of the other Lewis acids mentioned is used, in a solvent mixture, consisting of a halogenohydrocarbon, for example methylene chloride, and a lower alkanol, for example ethanol or isopropanol.

Equation 2

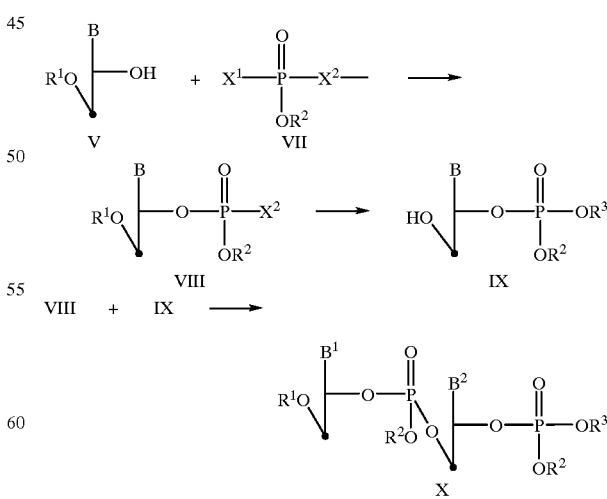

The preparation, according to the invention, of dinucleotides of the formula X also comprises the reaction of nucleosides of the formula V, in which $R^1$ and B are as defined above, with phosphites of the formula VIIA, in which $X^1$ is halogen, in particular chlorine, $X^2$ is halogen, in particular chlorine, di-lower alkylamino, in particular dimethylamino or diisopropylamino, or morpholino, piperidino or pyrrolidino, and $R^2$ is as defined above for VII, and is, in particular, methyl, in the presence or absence of a suitable base. The compounds of the formula VIIIA obtainable according to the invention are reacted, on the one hand, with a 2-substituted ethanol, which converts the radical $X^2$ into a group $OR^3$, in which $R^3$ is as defined above, and are then oxidized with an oxidizing agent, for example iodine, in the presence of a base to give the phosphate, and the protective group $R^1$ is detached, a compound of the formula IX being formed, or, on the other hand, are reacted with a compound of the formula IX and are then oxidized with an oxidizing agent, for example iodine in the presence of a base, to give a compound of the formula X (equation 3).

Equation 3

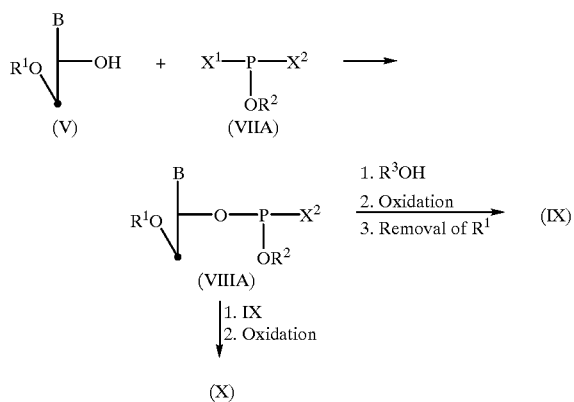

To prepare, according to the invention, trinucleotides, the protective group $R^1$ is detached from dinucleotides of the formula X, in which $R^1$, $R^2$ and $R^3$ are as defined above and in which $B^1$ and $B^2$ independently of one another are thymyl, costosyl, adenyl or guanyl, and the resulting compound is reacted with a compound of the formula VIII, in the presence or absence of dehydrating agents or in the presence or absence of bases, or with a compound of the formula VIIIA, with subsequent oxidation, a compound of the formula XI being formed (equation 4). The detachment of the protective group $R^1$ and the condensation to give the trinucleotides of the formula XI are carried out in the same manner as that described for the preparation of the dinucleotides of the formula X.

Equation 4

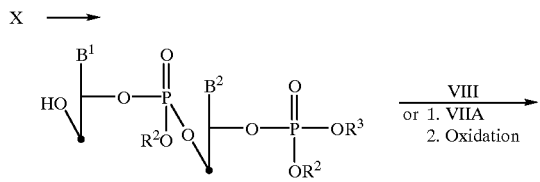

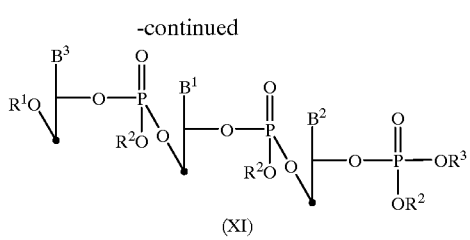

To prepare, according to the invention, tetranucleotides, trinucleotides of the formula XI are reacted as described above for dinucleotides of the formula X.

In a preferred embodiment of the invention, the 4-methoxytrityl group is used as the protective group $R^1$, a phenyl group substituted by chlorine, in particular 2-chlorophenyl, is used as the protective group $R^2$ and the 2-cyanoethyl group is used as the protective group $R^3$. The 1-benzotriazolyloxy radical is the preferred radical $X^1$ and $X^2$ in the compound of the formula VII.

Trinucleotides of the formula XI are preferably prepared by detaching the protective group $R^1$ from dinucleotides of the formula X and reacting the resulting compound with compounds of the formula VIII, in which $X^2$ is hydroxyl or salts derived therefrom, in the presence of a dehydrating agent (equation 4). Examples of dehydrating agents according to the invention are 2,4,6-trimethyl- or -triisopropyl-benzenesulfonyl chloride, -imidazolide, -tetrazolide or -1,2,4-triazolide, unsubstituted or substituted by nitro. 2,4,6-Trimethylbenzenesulfonyl-3-nitro-1,2,4-triazolide of the formula XII

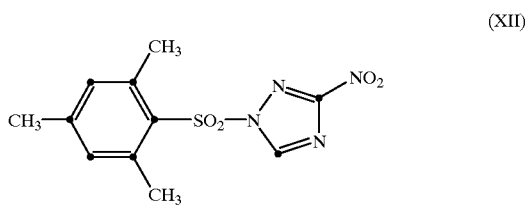

is the preferred dehydrating agent.

Nucleosides in which the free amino group in the base part is protected are preferably used. Preferred protective groups are benzoyl for adenine, benzoyl or 4-methoxybenzoyl for cytosine, and isobutyryl or diphenylacetyl for guanine. Thymine is preferably used without a protective group.

An apparatus which is known per se and has a semi-automatic or fully automatic, microprocessor-controlled feed system for solvents and reagents is used in the preparation, according to the invention, of oligonucleotides in step c). The protective group $R^1$ is detached, as described above, from a compound of the formula VI prepared according to step a), and the product is then reacted either with a compound of the formula VIII, or with a compound of the formula VIIIA, or with a compound of the formula X or XI, in which the protective group $R^3$ has been detached beforehand with bases (a 2-cyanoethyl group $R_3$ is detached, for example, with a tri-lower alkylamine, for example triethylamine, in one of the abovementioned inert solvents or solvent mixtures at 10° C. to 40° C., in particular at room temperature), in the presence or absence of a dehydrating agent or in the presence or absence of a base. The invention also relates to reactions in which a tetranucleotide prepared according to step b) is used instead of a dinucleotide of the formula X or a trinucleotide of the formula XI. If a phosphite of the formula VIIIA is used, after-treatment is subsequently carried out with an oxidising agent, for example iodine in the presence of a base. The compound of the formula XIII prepared in this manner, in which $R^1$, $R^2$ and B are as defined above and n is an integer from 1 to 4, is subjected to the reaction steps described for the compound of the formula VI (detachment of $R^1{}_1$ reaction with VIII, VIIIA, X, XI or the corresponding tetranucleotide, if appropriate with oxidative after-treatment) as frequently as necessary until a compound of the formula XIII is formed, in which n is any selected number between about 19 and about 69.

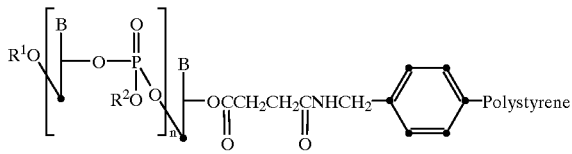

XIII

In a preferred embodiment of the invention, 4-methoxytrityl is used as the protective group $R^1$ and the detachment is carried out with zinc bromide in the presence of a CH- or NH-acid compound, in particular 1,2,4-triazole or tetrazole. The use of, for example, 1,2,4-triazole in the detachment of the 4-methoxytrityl protective group is novel and, surprisingly, leads to the detachment-proceeding rapidly, with high yields and without side reactions. It is particularly preferable to use zinc bromide and 1,2,4-triazole in a molar ratio of between 20:1 and 100:1 in a solvent mixture consisting of an aprotic solvent and an alcohol, for example methylene chloride and 2-propanol.

In a preferred embodiment of the invention, a compound of the formula VI or of the formula XIII, in which the lprotective group $R^1$ has been detached, is reacted with a trinucleotide of the formula XI, in which the protective group $R^3$ has been detached, in the presence of a dehydrating agent, for example 2,4,6-trimethyl- or -triisopropyl-benzene-sulfonyl chloride, -imidazolide, -tetrazolide or -1,2,4-triazolide, unsubstituted or substituted by nitro. 2,4,6-Trimethylbenzenesulfonyl-3-nitro-1,2,4-triazolide of the formula XII is particularly preferred.

The particularly preferred combination, which comprises using the 4-methoxytrityl group as the protective group $R^1$, using zinc bromide in the presence of 1,2,4-triazole for the detachment of $R^1$ and using the triazolide of the formula XII as the dehydrating agent for the reaction of the de-protected oligonucleotide/polystyrene resin of the formula XIII with a de-protected trinucleotide of the formula XI makes it possible, surprisingly, for long nucleotide chains with about 40 to about 70 bases also to be prepared in a short time, in high yields and in high purity.

Processes which are known per se are used for the detachment, according to the invention, of the oligodeoxynucleotides from the carrier and for the removal of the protective groups in step d). An arylaldoximate, for example 1,1,3,3-tetramethylguanidinium 2-nitrobenzaldoximate, is the particularly preferred reagent for detachment from the carrier and for removal of the preferred 2-chlorophenyl protective group. The reaction is carried out in one of the abovementioned inert solvents, to which a little water has been added, for example in 95% pyridine, at room temperature. The product is then reacted with aqueous ammonia at room temperature or elevated temperature, for example at 20° C. to 70° C., in particular at 50° C.

For ligation of the oligodeoxynucleotides according to the invention, a phosphate radical is introduced at the 5'-terminal hydroxyl group. The introduction of the phosphate radical (phosphorylation) is carried out in a manner which is known per se, with the aid of $T_4$ polynucleotide kinase in the presence of ATP.

Oligodeoxynucleotides, prepared according to the invention, from the coding and the complementary DNA strand contain overlapping sequences consisting of at least 3, preferably 8 to 15, overlapping base pairs. Such oligodeoxynucleotide pairs are held together by hydrogen bridge bonding during mixing. The overhanging, single-stranded ends serve, in step e1) and e2), as the matrix (template) for the build-up of the second (complementary) strand by a DNA-polymerase, for example DNA-polymerase I, the Klenow fragment of DNA-polymerase I or $T_4$ DNA-polymerase, or with AMV reverse transcriptase, in the presence of the four deoxynucleoside triphosphates (dATp, dCTp, dGTp and TTP). The duplex-DNAs formed during complementing, which are, in particular, fragments of the (modified) eglin gene (process e1) or the complete (modified) eglin gene (process e2) have flat ends.

The fragments of the (modified) eglin gene which are obtainable by process step e1) contain, on their ends, nucleotide sequences which can be recognised and cleaved by restriction endonucleases. Depending on the choice of nucleotide sequences and accordingly the restriction endonucleases, completely base-paired (flat) ends ("blunt ends") or ends with an overhanging DNA strand ("staggered ends") are formed during cleavage. The restriction recognition sequences are chosen so that the ligation of the DNA fragments which have been treated with a restriction endonuclease which forms blunt ends, or the base-pairing of the cohesive ends and the subsequent ligation of DNA fragments with staggered DNA strands produces the complete (modified) eglin structure gene. The ligation of two double-stranded DNA fragments requires a 5'-terminal phosphate group on the donor fragment and a free 3'-terminal hydroxyl group on the acceptor fragment. The DNA fragments obtained are already 5'-terminally phosphorylated and are linked with a ligase, in particular $T_4$ DNA-ligase, in a manner which is known per se.

In a preferred embodiment of the present invention, two fragments of the eglin C or B gene, in the case of the eglin C gene in particular the fragments $F_1(C)$ and $F_2$ according to formula IIIa or IV, and in the case of the eglin B gene in particular fragments $F_1(B)$ and $F_2$ according to formula IIIb or IV, are prepared in the manner described. The fragments, which can be subcloned in a suitable vector if necessary, preferably contain in each case the recognition sequence for a restriction endonuclease, in particular HpaII, at the linking ends, which is why, after cleavage with the said restriction enzyme and ligation of the two fragments, the correctly coding eglin DNA sequence is formed. In addition, the fragment 1 before the translation start signal (ATG) and the fragment 2 after the translation stop signal (for example TAG) also contain "terminal" restriction sites which allow incorporation of the (modified) eglin gene or the (modified) eglin gene fragments into a suitable vector.

The invention particularly relates to the preparation of the eglin C gene in two fragments $F_1(C)$ and $F_2$ of the formula IIIa and IV, which produce the correct eglin C DNA sequence after cleavage with the restriction enzyme HpaII and ligation, and in which $F_1(C)$ has an EcoRI restriction site before the translation start signal and $F_2$ has a BamHI restriction site after the translation stop signal.

In another embodiment (step e2), in each case two oligodeoxynucleotides, which originate alternatively from the coding and the complementary strand, are fused by means of at least 3, preferably 8 to 15, complementary bases, made up with a DNA-polymerase, for example one of those mentioned above, and ligated with $T_4$ DNA-ligase to give the (modified) eglin structure gene.

Preparation of Expression Vectors Containing an Eglin Gene

The invention furthermore relates to expression vectors which contain a DNA sequence which codes an eglin or a modified eglin and which is regulated by an expression control sequence such that polypeptides with eglin activity are expressed in a host transformed with these expression vectors.

The expression vectors according to the present invention contain a sequence which codes eglin B, modified eglin B, modified eglin C or, in particular, eglin C.

The expression vectors of the present invention are prepared, for example, by inserting a DNA sequence which codes an eglin or a modified eglin into a vector-DNA, which contains an expression control sequence, such that the expression control sequence regulates the said DNA sequence.

A suitable vector is chosen from the host cells envisaged for transformation. Examples of suitable hosts are microorganisms, such as yeasts, for example *Saccharomyces cerevisiae,* and, in particular, strains of bacteria which do not have restriction enzymes or modification enzymes, in particular strains of *Escherichia coli,* for example *E. coli* X1776, *E. coli* HB101, *E. coli* W3110, *E. coli* HB101/ LM1035, *E. coli* JA221(37) or *E. coli* K12 strain 294, *Bacillus subtilis, Bacillus stearothermophilus,* Pseudomonas, Haemophilus, Streptococcus and others, and furthermore cells of higher organisms, in particular established human or animal cell lines. The above strains of *E. coli,* for example *E. coli* HB101 and *E. coli* JA221, and furthermore *Saccharomyces cerevisiae* are preferred as the host microorganism.

In principle, all vectors which replicate and express the DNA sequences according to the invention in the chosen host are suitable.

Examples of vectors which are suitable for the expression of an eglin or modified eglin gene in an *E. coli* strain are bacteriophages, for example derivatives of λ bacteriophages, or plasmids, such as, in particular, the plasmid co1E1 and its derivatives, for example pM89, pSF2124, pBR317 or pBR322. The preferred vectors of the present invention are derived from plasmid pBR322. Suitable vectors contain a complete repticon and a labelling gene, which makes it possible to select and identify the hosts transformed with the expression plasmids on the basis of a phenotypical characteristic. Suitable labelling genes impart to the host, for example, resistance towards heavy metals, antibiotics and the like. Furthermore, preferred vectors of the present invention contain, outside the replicon and labelling gene regions, recognition sequences for restriction endonucleases, so that the eglin gene and, if appropriate, the expression control sequence can be inserted at these sites. The preferred vector, the plasmid pBR322, contains an intact replicon, labelling genes which impart resistance towards tetracycline and ampicillin ($tet^R$ and $amp^R$) and a number of recognition sequences, occurring only once, for restriction endonucleases, for example PstI (cleaves in the $amp^R$ gene, the $tet^R$ gene remains intact), BamHI, HindIII and SaLI (all cleave in the $tet^R$ gene, the $amp^R$ gene remains intact), NruI and EcoRI.

Several expression control sequences can be used for regulation of the gene expression. In particular, expression control sequences of highly expressed genes of the host to be transformed are used. In the case of pBR322 as the hybrid vector and *E. coli* as the host microorganism, for example, the expression control sequences (which contain, inter alia, the promoter and the ribosomal bonding site) of the lactose operon, tryptophan operon, arabinose operon and the like, the β-lactamase gene, the corresponding sequences of the phage λN gene or the phage fd-stratified protein gene and others, are suitable. Whilst the plasmid peR322 already contains the promoter of the β-lactamase gene (β-lac-gene), the other expression control sequences must be introduced into the plasmid. The preferred expression control sequence in the present invention is that of the tryptophan operon (trp po).

Vectors which are suitable for replication and expression in yeast contain a yeast replication start and a selective genetic marker for yeast. Hybrid vectors which contain a yeast replication start, for example chromosomal autonomously replicating segment (ars), are retained extrachromosomally within the yeast cell after the transformation and are replicated autonomously during mitosis. Furthermore, hybrid vectors which contain sequences homologous to the yeast-2µ-plasmid-DNA can be used. Such hybrid vectors are incorporated by recombination within the cell of already existing 2µ-plasmids, or replicate autonomously. 2-sequences are particularly suitable for plasmids with a high transformation frequency and permit a high number of copies. Suitable labelling genes for yeasts are, in particular, those which impart antibiotic resistance to the host or, in the case of auxotrophic yeast mutants, genes which complement host defects. Corresponding genes impart, for example, resistance towards the antibiotic cycloheximide or ensure prototrophy in an auxotrophic yeast mutant, for example the URA3, LEU2, HIS3 or, in particular, TRP1 gene. Yeast hybrid vectors furthermore preferably contain a replication start and a labelling gene for a bacterial host, in particular *E. coli,* so that the construction and cloning of the hybrid vectors and their intermediates can take place in a bacterial host. Expression control sequences which are suitable for expression in yeast are, for example, those of the TRP1, ADHI, ADHII, PH03 or PH05 gene, and furthermore promoters involved in glycolytic degradation, for example the PGK and the GAPDH promoter.

The invention particularly relates to expression vectors which are capable of replication and phenotypical selection and which contain an expression control sequence and a DNA sequence which codes an eglin or a modified eglin, the said DNA sequence together with the transcription start signal and termination signal and the translation start signal and stop signal being arranged in the said expression plasmid under regulation of the said expression control sequence such that polypeptides with eglin activity are expressed in a host transformed with the said expression plasmid.

In order to achieve effective expression, the structure gene must be arranged correctly (in "phase") with the expression control sequence. It is advantageous for the expression control sequence to be linked with the eglin (or modified eglin) gene, which preferably contributes its own translation start signal (ATG) and translation stop signal (for example TAG), in the region between the main mRNA start and the ATG of the gene-coding sequence, which is of course linked with the expression control sequence (for example the β-lac-coding sequence when the β-lac promoter is used). Effective transcription and translation are thereby ensured.

For example, a vector, in particular pBR322, is cleaved with a restriction endonuclease and, if appropriate after modification of the linearised vector thus formed, an expression control sequence provided with corresponding restriction ends is introduced. The expression control sequence contains the recognition sequence of a restriction endonuclease at the 3'-end (in the translation direction), so that the vector already containing the expression control sequence can be digested with the said restriction enzyme and the eglin (or modified eglin) structure gene provided with appropriate ends can be inserted. A mixture of two hybrid plasmids containing the gene in correct and incorrect orientation is thereby formed. It is advantageous also to cleave the vector already containing the expression control sequence with a second restriction endonuclease within the vector-DNA and to insert the structure gene provided with correct ends in the resulting vector fragment. All the operations on the vector are preferably carried out such that the function of the replicon and at least one labelling gene is not impaired.

In a preferred embodiment of the present invention, a vector derived from pBR322, which contains an expression control sequence, in particular that of tryptophan operon (trp po), which carries at the 3'-end (between the main mRNA start and the first ATG), the recognition sequence for a restriction endonuclease, which preferably forms cohesive ends, for example EcoRI, is digested with the restriction endonuclease mentioned and, in the vector-DNA part, with a second restriction endonuclease which forms blunt or, preferably, cohesive ends, for example BamHI, after which the vector thus linearised links with the eglin (or modified eglin) gene containing the appropriate ends (for example with an EcoRI end before the ATG start and a BamHI end after the translation stop codon). Linking is effected in the known manner, by pairing of the complementary (cohesive) ends and ligation, for example with $T_4$-DNA-ligase.

The eglin (or modified eglin) gene obtained via the mRNA route, from genomic DNA or synthetically and provided with corresponding cohesive (in particular EcoRI and BamHI) ends can also be cloned in a vector, for example pBR322, before introduction into an expression plasmid, in order to obtain larger amounts of structure gene, for example for sequence analysis. The cLones containing the hybrid plasmid are isolated, for example, with an eglin-specific, radio-actively labelled oligodeoxynucleotide probe (see above). The eglin (or modified eglin) gene is characterised, for example, by the method of Maxam and Gilbert (3).

In a preferred embodiment of the invention, two fragments of an eglin or modified eglin gene, for example two fragments of the eglin C gene, are synthesised. Fragment 1, which includes the 1st part of the gene, contains, before the ATG and at the end, in each case the recognition sequence for restriction endonucleases which form cohesive ends, for example EcoRI before the ATG and HpaII at the end. Fragment 2, which includes the rear part of the gene, has corresponding recognition sequences, for example HpaII at the start, and BamHI after the translation stop signal (for example TAG). The fragments are cleaved at the outer recognition sequences (fragment 1, for example, with EcoRI and fragment 2 correspondingly with BamHI) and are subcloned in a correspondingly cleaved vector (for example pBR322). The identification of the clones containing the fragments and the characterisation of the fragments are carried out as described above. The fragments are then excised from the hybrid vectors with the corresponding restriction endonucleases (fragment 1, for example, with EcoRI and HpaII and fragment 2, for example, with HpaII and BamHI) and are Ligated via their cohesive ends, in particular their HpaU ends, whereupon the complete eglin (or modified eglin) gene is formed, this gene being inserted, as described, into a vector-DNA.

Transformation of the Host Cells

The invention also reLates to a process for the preparation of a transformed host, which comprises transforming a host with an expression plasmid containing a DNA sequence which is regulated by an expression control sequence and codes an eglin or a modified eglin.

Examples of suitable hosts are the abovementioned microorganisms, such as strains of *Saccharomyces cerevisiae, Bacillus subtilis* and, in particular, *Escherichia coli*. The transformation with the expression plasmids according to the invention is carried out, for example, as described in the literature, thus for *S. cerevisiae* (4), *B. subtilis* (5) and *E. coli* (6). The transformed host is advantageously isolated from a selective nutrient medium, to which the biocide against which the labelling gene contained in the expression plasmid imparts resistance is added. If, as preferred, the expression plasmids contain the $amp^R$ gene, ampicillin is accordingly added to the nutrient medium. Cells which do not contain the expression plasmid are destroyed in such a medium.

The invention also relates to the transformed host obtainable by the route described.

Culture of the Transformed Host and Production of Eglins

The transformed host can be used for the preparation of eglins and modified eglins. The process for the preparation of eglins and modified eglins comprises culturing the transformed host and releasing the product from the host cells and isolating it.

Surprisingly, it has now been found that the transformed hosts according to the invention produce mixtures of polypeptides with eglin activity. Natural eglins, methionyl-eglins and N-terminally acetylated or shortened eglins can be isolated from the mixtures in varying ratios, depending on the host microorganism used and the cultivation conditions applied. Thus, one important product which can be isolated from transformed *E. coli* strains and from transformed yeast differ from the natural eglins B and C by an N-acetyl radical on the N-terminal aminoacid threonine. The production of $N^\alpha$-acetylated products is particularly surprising. In particular, the production of such polypeptides by means of genetic engineering methods has not yet hitherto been observed. Thus, even α-thymosin, which is naturally N-terminally acetylated, is expressed in the non-acetylated form by corresponding genetically modified hosts (35).

The production of N-terminally acetylated eglins is of great advantage, because such compounds have an increased stability towards the aminopeptidases present in the host cells, which means that (partial) proteolytic degradation starting from the N-terminus is prevented and as a result the yield is increased. Furthermore, the purification process is thereby considerably simplified, because the desired products are not contaminated with fragments formed by proteolytic degradation.

The present invention thus furthermore relates to a process for the preparation of eglin compounds of the formula (Met)$_r$-B-ProGluValValGlyLysThrVal-
AspGlnAlaArgGluTyrPheThrLeu-
HisTyrProGlnTyrAspValWPheLeu-
ProGluGlySerProValThrLeuAspLeuArgTyrAsnArg
ValArgValPheTyrAsnProGlyThrAsnValValAsn-B' 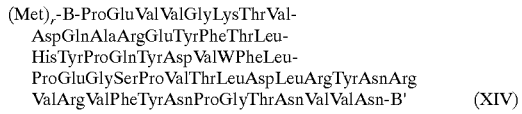 (XIV)

in which B is a direct bond or a peptide radical comprising 1–10 aminoacid units from the N-terminus of the natural eglins, for example such a radical chosen from the group comprising SerPhe, LeuLysSerPhe, SerGluLeuLysSerPhe, PheGlySerGluLeuLysSerPhe and ThrGluPheGlySerGLuLeuLysSerPhe, and B' is not a peptide radical or is a peptide radical which comprises 1–6 aminoacid units from the C-terminus of the naturat eglins, for example such a radical chosen from the group comprising HisVal, HisValProHis or HisValProHisValGly, W is Tyr or His and r is 0 or 1, and in which, in compounds of the formula XIV in which r is 0, the N-terminal aminoacid is free or N-acetylated, and of salts of such compounds, which comprises culturing a host transformed with an expression plasmid containing an eglin-coding DNA sequence regulated by an expression control sequence, in a liquid nutrient medium containing assimilatable sources of carbon and nitrogen, releasing the product from the host cells and isolating it, or, for the preparation of compounds of the formula XIV, in which r is 0 and the N-terminal aminoacid is N-acetylated, acetylating a compound of the formula XIV with a free N-terminal amino group and, if desired, converting an eglin compound of the formula XIV, which can be obtained, into another eglin compound of the formula XIV, and, if necessary, separating a mixture, obtainable according to the process, of compounds of the formula XIV into the individual components, and/or, if desired, converting a resulting salt into the free polypeptide and converting a resulting polypeptide into a salt thereof.

The invention preferably relates to a process for the preparation of eglin compounds of the formula

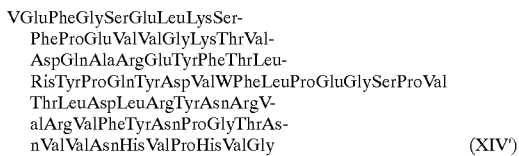

VGluPheGlySerGluLeuLysSer-
PheProGluValValGlyLysThrVal-
AspGlnAlaArgGluTyrPheThrLeu-
RisTyrProGlnTyrAspValWPheLeuProGluGlySerProVal
ThrLeuAspLeuArgTyrAsnArgV-
alArgValPheTyrAsnProGlyThrAs-
nValValAsnHisValProHisValGly (XIV')

in which V is Thr, N-acetyl-Thr or Met-Thr and W is Tyr or His, and of salts of such compounds, which comprises culturing a host microorganism transformed with an expression plasmid containing an eglin-coding DNA sequence regulated by an expression control sequence, in a liquid nutrient medium containing assimitatable sources of carbon and nitrogen, releasing the eglin from the microorganism cells and isolating it, and, if desired, converting an eglin which can be obtained, in which V is N-acetyl-Thr or Met-Thr and W has the above meaning, into an eglin in which V is Thr, and, if necessary, separating a mixture, obtainable according to the process, of compounds of the formula XIV into the individual components, and/or, if desired, converting a resulting salt into the free polypeptide or a resulting polypeptide into a salt thereof.

The invention particularly relates to a process for the preparation of eglin C compounds of the formula XIV, in which B is a peptide radical selected from the group comprising LeuLysSerphe, SerGluLeuLysSerPhe, PheGlySerGluLeuLysSerPhe and ThrGLuPheGlySerGluLeuLysSerPhe, B' is the radical -HisValProHisVatGly, W is Tyr and r is 0 or 1, and furthermore also a process for the preparation of eglin B compounds of the formula XIV, in which B is the peptide radical ThrGluPheGlySerGLuLeuLysSerPhe, B' is the peptide radical -HisValProHisValGly, W is His and r is 0 or 1, the N-terminal aminoacid in compounds of the formula XIV in which r is 0 being free or N-acetylated, and of salts of such compounds.

In the compounds of the formula XIV, W is preferably Tyr (eglin C compounds).

The invention particularly relates to a process for the preparation of eglin C compounds of the formula XIV, in which B is the PheGlySerGluLeuLysSerPhe, ThrGLuPheGlySerGluLeuLysSerPhe or N-acetyl-ThrGluPheGlySerGluLeuLysSerphe radical, B' is theHisValProHisValGly radical, W is Tyr and r is 0, and of salts of such compounds.

The invention especially relates to a process for the preparation of eglin C, N-methionyl-eglin C, N-acetyl-eglin C, the modified eglin C compound Des-eglin C, and the modified eglin C compound eglin C' and eglin C".

Various sources of carbon can be used for culture of the transformed hosts according to the invention. Examples of preferred sources of carbon are assimilatable carbohydrates, such as glucose, maltose, mannitol or lactose, or an acetate, which can be used either by itself or in suitable mixtures. Examples of suitable sources of nitrogen are aminoacids, such as casaminoacids, peptides and proteins and their degradation products, such as tryptone, peptone or meat extracts; and furthermore yeast extracts, malt extract and also ammonium salts, for example ammonium chloride, sulfate or nitrate, which can be used either by themselves or in suitable mixtures. Inorganic salts which can also be used are, for example, sulfates, chlorides, phosphates and carbonates of sodium, potassium, magnesium and calcium.

The medium furthermore contains, for example, growth-promoting substances, such as trace elements, for example iron, zinc, manganese and the like, and preferably substances which exert a selection pressure and prevent the growth of ceLls which have lost the expression plasmid. Thus, for example, ampicillin is added to the medium if the expression plasmid contains an amp$^R$ gene. Such an addition of antibiotic substances also has the effect that contaminating antibiotic-sensitive microorganisms are destroyed.

Culture is effected by processes which are known per se. The culture conditions, such as temperature, pH value of the medium and fermentation time, are chosen so that a maximum eglin titre is obtained. Thus, an E. coli strain is preferably cultured under aerobic conditions by submerse culture with shaking or stirring at a temperature of about 20 to 40° C., preferably about 30° C., and a pH value of 4 to 9, preferably at pH 7, for about 4 to 20 hours, preferably 8 to 12 hours. The expression product (eglin) thereby accumulates intracellularly.

When the cell density has reached a sufficient value, the culture is interrupted and the eglin is released from the cells of the host. For this purpose, the cells are destroyed, for example by treatment with a detergent, such as SDS or triton, or Lysed with lysozyme or a similarly acting enzyme. Alternatively or additionally, mechanical forces, such as shearing forces (for example X-press, French press, Dyno mill) or shaking with glass beads or aluminium oxide, or alternating freezing, for example in liquid nitrogen, and thawing, for example to 30° to 40° C., as well as ultra-sound can be used to break the cells. The resulting mixture, which contains proteins, nucleic acids and other cell constituents, is enriched in proteins, including eglin, in a manner which is known per se, after centrifugation. Thus, for example, most of the non-protein constituents are removed by polyethyleneimine treatment and the proteins, including eglin, are precipitated, for example, by saturation of the solution with ammonium sulfate or with other salts. Bacterial proteins can also be precipitated by acidification with acetic acid (for example 0.1%, pH 4–5). Further enrichment of eglin can be achieved by extraction of the acetic acid supernatant liquor with n-butanol. Further purification steps include, for example, gel electrophoresis, chromatographic processes, such as ion exchange chromatography, size exclusion chromatography, HPLC, reverse phase HPLC and the like, separation of the constituents of the mixture according to molecular size by means of a suitable Sephadex column, dialysis, affinity chromatography, for example antibody, especially monoclonal antibody, affinity chromatography or affinity chromatography on an anhydrochymotrypsin column, and other known processes, especially those known from the literature.

Isolation of the expressed eglins comprises, for example, the following stages: removal of the cells from the culture solution by means of centrifugation; preparation of a crude extract by destruction of the cells, for example by treatment with a lysing enzyme and/or alternating freezing and rethawing; removal of the insoluble constituents by centrifugation; precipitation of the DNA by addition of polyethyleneimine; precipitation of the proteins, including eglin, by ammonium sulfate; affinity chromatography of the dissolved precipitate on a monoclonal anti-eglin antibody column or an anhydrochymotrypsin column; demineralisation of the resulting solution by means of dialysis or chromatography on Sephadex G25.

Alternatively, after the DNA has been separated off, the bacterial proteins can be precipitated with 0.1% acetic acid and the eglin can be extracted from the acid supernatant liquor with n-butanol or the acid supernatant liquor can be subjected directly to ion exchange chromatography (for example on carboxymethylcellulose). Further purification steps include gel filtration on Sephadex G50 (or G75) and reverse phase HPLC. Demineralisation is again carried out on Sephadex G25.

The test with anti-eglin antibodies (for example monoclonal antibodies obtainable from rabbits or from hybridoma cells) or the inhibition of the proteases human leucocyte elastase (HLE) or cathepsin G (cat G) (1) by eglin can be used to detect the eglin activity.

The conversion of a compound of the formula XIV, in which r is 0 and the N-terminal amino group is in the free form, into a corresponding compound of the formula XIV, in which the N-terminal aminoacid is N-acetylated, is effected, in particular, by an enzymatic route. Thus, the introduction of the acetyl group can be carried out, for example, with the aid of an Nα-acetyl-transferase (in the pure form, as an extract or lysate of a suitable microorganism or as an organ extract), for example from E. coli, from rabbit reticulocytes or wheat seedlings (8), in the presence of acetyl-coenzyme A.

Compounds of the formula XIV obtainable according to the process can be converted into other compounds of the formula XIV in a manner which is known per se.

Thus, methionine or the acetyl radical can be detached from compounds of the formula XIV, which can be obtained, with methionine as the N-terminal aminoacid or with an N-terminably acetylated amino group. For example, eglin compounds obtainable according to the invention with an N-terminal methionyl radical can be converted into eglins without such a radical by detaching the terminal methionyl radical by means of cyanogen bromide in the usual manner. The reaction with cyanogen bromide is carried out, for example, in an aqueous-acid medium, for example in very dilute hydrochloric acid, for example in 0.1–0.3 N hydrochloric acid, or in a strong organic acid, for example in 50–70% formic acid, at room temperature or slightly elevated or reduced temperature, for example at about 15° to about 25° C., over a period of about 24 hours. The acetyl radical can correspondingly be detached from compounds of the formula XIV, obtainable according to the process, with an N-terminally acetylated amino group. The detachment of the acetyl radical can be carried out, for example, enzymatically, such as with suitable acylases, for example from pigs' kidneys or from suitable microorganisms, or with suitable acetyl-transferases in the presence of coenzyme A, it also being possible to use extracts or lysates from microorganisms or organ extracts containing such enzymes instead of pure enzyme products (for example an E. coli HB101 lysate when E. coli HB101 is used as the strain producing Nα-acetyl-eglin B or C).

A mixture, obtainable according to the process, of compounds of the formula XIV, for example consisting of compounds of the formula XIV, in which V is either Thr or acetyl-Thr, can be separated into the individual components in a manner which is known per se.

Examples of suitable separation methods are chromatographic processes, for example adsorption chromatography, ion exchange chromatography, HPLC or reversed phase HPLC, and furthermore multiplicative distribution or electrophoretic methods, for example electrophoresis on cellulose acetate or gel electrophoresis, in particular polyacrylamide gel electrophoresis ("PAGE").

The invention also relates to the novel peptides with eglin activity, which are obtainable by the process according to the invention, mixtures of such peptides and salts of such compounds.

The invention furthermore relates to the novel compounds of the formula

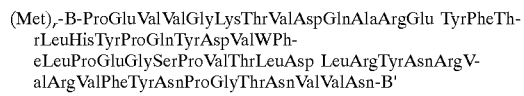
(Met),-B-ProGluValValGlyLysThrValAspGlnAlaArgGlu TyrPheTh-
rLeuHisTyrProGlnTyrAspValWPh-
eLeuProGluGlySerProValThrLeuAsp LeuArgTyrAsnArgV-
alArgValPheTyrAsnProGlyThrAsnValValAsn-B' in which r is 1, B is a direct bond or a peptide radical comprising 1–10 aminoacid units from the N-terminus of the natural eglins, for example a radical selected from the group comprising SerPhe, LeuLysSerPhe, SerGluLeuLysSerPhe, PheGlySerGluLeuLysSerPhe and ThrGluPheGlySerGluLeuLysSerPhe, and B' is not a peptide radical or is a peptide radical comprising 1–6 aminoacid units from the C-terminus of the natural eglins, for example such a radical selected from the group comprising -HisVal, -HisValProHis and -HisVaLProHisValGly, and W is Tyr or His, or in which r is 0, B is PheGlySerGLuLeuLysSerPhe or an N-terminally acetylated peptide radical, for example selected from the group comprising N-acetyl-SerPhe, N-acetyl-LeuLysSerPhe, N-acetyl-SerGluLeuLysSerPhe, N-acetyl-PheGLySerGluLeuLysSerPhe and N-acetyl-ThrGLuPheGLySerGLuLeuLysSerPhe, B' is as defined and W is Tyr or His, and salts of such compounds.

The invention particularly relates to compounds of the formula XIV, in which r is 0, B is the peptide radical PheGlySerGLuLeuLysSerPhe or N-acetyl-ThrGluPheGLySerGluLeuLysSerPhe, B' is the peptide radical-HisValProHisVaLGly and W is Tyr, and salts of such compounds.

The invention preferably relates to eglin compounds of the formula

VGluPheGlySerGluLeuLysSer-
PheProGluValValGlyLysThrValAspGlnAlaArgGlu TyrPheThr-
LeuHisTyrProGlnTyrAspValWPh-
eLeuProGluGlySerProValThrLeuAsp
LeuArgTyrAsnArgValArgValPheT-
yrAsnProGlyThrAsnValValAsnHisvalProHis ValGly (XIV'), in which V is N-acetyl-Thr or Met-Thr and W is Tyr or His, and salts of such compounds.

The invention particularly relates to Nα-acetyl-eglin C and salts thereof.

The compounds which can be prepared according to the invention and the novel compounds of the formula XIV can be not only in the free form, but also in the form of their salts, in particular their pharmaceutically acceptable salts. Since they contain several aminoacid radicals with free amino groups or guanidino groups, the compounds according to the invention can be, for example, in the form of acid addition salts. Possible acid addition salts are, in particular, physiologically acceptable salts with the usual therapeutically useful acids; inorganic acids are the hydrogen halide acids (such as hydrochloric acid), and also sulfuric acid and phosphoric or pyrophosphoric acid; suitable organic acids are, in particular, sulfonic acids (such as benzene- or p-toluene-sulfonic acid or lower alkanesulfonic acids, such as methane-sulfonic acid) and carboxylic acids, such as acetic acid, lactic acid, palmitic and stearic acid, malic acid, tartaric acid, ascorbic acid and citric acid. Since the eglin compounds also contain aminoacid radicals with free carboxyl groups which impart acid character to the entire peptide, they can also be in the form of a metal salt, in particular an alkali metal or alkaline earth metal salt, for example a sodium, potassium, calcium or magnesium salt, or an ammonium salt, derived from ammonia or a physiologically acceptable organic nitrogen-containing base. However, since they contain free carboxyl groups and free amino (and amidino) groups at the same time, they can also be in the form of an inner salt.

Depending on the procedure, the compounds according to the invention are obtained in the free form or in the form of acid addition salts, inner salts or salts with bases. The free compounds can be obtained from the acid addition salts in a manner which is known per se. Therapeutically acceptable acid addition salts or metal salts can in turn be obtained from the tatter by reaction with acids or bases, for example with those which form the abovementioned salts, and evaporation or lyophitisation. The inner salts can be obtained by adjusting the pH to a suitable neutral point.

Monoclonal Antibodies Against Eglins and Test Kits Containing Such Antibodies

The property of antibodies of binding specific antigens finds practical application outside the body in the quantitative determination (immunoassay) and in the purification of antigens (immunoaffinity chromatography). Serum from immunised animals usually contains a large number of various antibodies which react with the same antigen at various binding sites with various affinities, but in addition also antibodies against other antigens which reflect the earlier experiences of the individual. The successful use of antibodies for the determination and purification of antigens, however, requires high specificity and reproducibility.

Homogeneous antibodies which fulfill these requirements have been made accessible by the hybridoma technique described by Köhler and Milstein (26). In principle, the technique comprises fusing antibody-secreting B lymphocytes, for example from the spleen, of immunised animals with tumour cells. The hybridoma cells formed combine the ability to multiply by division without limitation with the ability to form and secrete a homogeneous type of antibody. By culture in a selective medium in which non-fused tumour cells die but hybridoma cells multiply, and by suitable manipulation, it is possible to obtain and culture clones, i.e. cell populations, which are derived from a single hybridoma cell and are genetically identical, and to isolate the monoclonal antibodies produced by the cells.

The present invention relates to monoclonal antibodies against eglins or modified eglins, hybridoma cells which produce such antibodies, and processes for their preparation. Hybridoma cell lines and the monoclonal antibodies secreted from these which react specifically with eglin B or eglin C or derivatives thereof, for example $N^\alpha$-acetyl-eglin C or B or $N^\alpha$-methionyl-eglin C or B, are preferred. The process for the preparation of monoctonal anti-eglin antibodies comprises immunising mice with an eglin or modified eglin, fusing B lymphocytes from animals immunised in this manner with myeloma cells, cloning the hybridoma cells formed, then culturing the clones in vitro or by injection into mice and isolating antibodies from the cultures.

The invention furthermore relates to immunoaffinity chromatography columns and test kits for immunoassays containing these antibodies.

In the process according to the invention, mice, for example Balb/c mice, are immunised in a manner which is known per se but which is specific. Surprisingly, the immunisation is successful, even though eglins are relatively small protein molecules. In a preferred embodiment, a solution of 50 to 500 $\mu$g, preferably 100 $\mu$g, of eglin B or C, in particular in complete and incomplete Freund's adjuvant and in buffered salt solution, is injected subcutaneously approximately every week or also at longer intervals over several weeks, for example 5 to 12 weeks, until a sufficient number of antibody-producing B lymphocytes has formed.

Organs containing B lymphocytes, for example spleen cells, are removed from the immunised mice and fused with those myeloma cells which, because of mutation, do not grow in a selective culture medium. Such myeloma cells are known and are, for example, those with the designation X63-Ag8, X63-Ag8.6.5.3, MPC-11, NS1-Ag4/1, MOPC-21 NS/1 or, in particular, SP 2/0. In a preferred embodiment, spleen cells from immunised mice are fused with myeloma cells of the cell line SP 2/0.

The fusion is carried out by processes known per se, by mixing the B lymphocytes and the myeloma cells, with the addition of a cell fusion agent, such as polyethylene glycol, Sendai virus, calcium chloride or lysolecithin. Fusion is preferably effected in the presence of polyethylene glycol, for example with a molecular weight of 500. After the fusion, the hybrids formed are cultured by a process which is known per se, in a selective culture medium complemented by hypoxanthine, aminopterin and thymidine (HAT medium). Non-fused myeloma cells cannot grow in this medium and die, as do normal lymphocytes.

The supernatant liquors from the hybridoma cultures can be tested for their content of specific antibodies by processes which are known per se, for example by radioimmunoassay or by agglutination. It is found here, surprisingly, that hybridoma cells which secrete antibodies specificalLy against eglin B or eglin C can be obtained by the process described. These antibodies also react with N$\alpha$-acetyl-eglin C and B and N$\alpha$-methionyl-eglin C and B.

The hybridoma cells which produce antibodies of the desired specificity are selected out, by cloning, from the mixture of the most diverse hybridoma cells resulting from the fusion. For this, cultures are started from a single growing cell by a process which is known per se, called "limiting dilution".

The three hybridoma cell lines deposited at the Pasteur Institute, Paris, France under the designation 299S18-20, 299S22-1 and 299S22-10 can be obtained in this manner.

For mass production, the hybridoma cell clones which produce antibodies of the desired specificity are either cultured in vitro in media which are known per se or are injected into mice, for multiplication. In a preferred embodiment, hybridoma cells are injected into mice pretreated with pristane, ascites fluid is withdrawn and antibodies are isolated therefrom by precipitation with ammonium sulfate solution.

The monoclonal antibodies obtained with the aid of these hybridoma cells can be used in a manner which is known per se for the preparation of immunoaffinity chromatography columns. In a preferred embodiment of the invention, an antibody solution is added to a suitable carrier material (suspended in a buffer solution), non-bound constituents are then washed out and unoccupied sites of the carrier material are blocked.

The monoclonal antibodies obtained with the aid of the hybridoma cells can be used in a manner which is known per se for the preparation of test kits. These test kits can be based on various methods, for example on radioimmuno-diffusion, latex agglutination, spot tests, competitive or sandwich radioimmunoassay, enzyme immunoassay, immunofluorescence or immunochemical enzyme tests, for example ELISA or tandem ELISA. Besides the usual antibodies of various origins, such kits can contain antibody conjugates with enzymes or fluorescence carriers, and in addition an eglin or modified eglin, for example eglin B, eglin C or Nα-acetyl-eglin C, Labelled with radioactive isotopes, such as $I^{125}$, or conjugated with enzymes, for example with horseradish peroxidase or alkaline phosphatase, and furthermore enzyme substrates, suitable buffers, gels, latex, polystyrene or other filling materials and carriers.

The serological tests can be carried out, for example, as follows: Besides competitive RIA, a direct bonding test can be utilised to establish anti-eglin C antibody activity. For this purpose, eglin C is fixed in depressions in microtitre plates (200 ng/depression) by incubation overnight and then incubated with hybridoma culture fluid and rendered visible with goat anti-mouse Ig antibodies either radioactively labelled with $^{125}I$ (solid phase RIA) or labelled by alkaline phosphatase (solid phase ELISA).

The three monoclonal antibodies selected are suitable for non-radioactive tandem ELISA, with the aid of which eglins can be determined quantitatively in body fluids.

The suitable pairs of antibodies were selected as follows, by means of competitive RIA: The monoclonal antibodies 299S18-20, 299S22-1 and 299S22-10 (200–300 ng/depression, obtained by ammonium sulfate precipitation from ascites fluid) and a polyclonal rabbit anti-eglin C antibody (200–300 ng/depression, obtained from serum) are fixed in depressions of microtitre plates. Inhibition of the bonding of $^{125}I$-labelled eglin C was investigated crosswise.

The experiments showed that the monoclonal antibodies 299S18-20 and 299S22-10 inhibit one another in bonding to eglin C, from which it can be concluded that they both bond to the same epitopes on the eglin C molecule.

The monoclonal antibodies 299S18-20 and 299S22-1 do not inhibit one another. This means that they bond to different epitopes of the eglin C molecule.

The relative bonding capacity, determined by the amount of fixed radioactively labelled eglin C bonded by the fixed antibodies, is highest with 299S22-10 and lowest with 299S18-20.

On the basis of tandem ELISA experiments, in which the monoclonal antibodies were tested in pairs, one antibody always being fixed as the solid phase on microtitre plates and the other being labelled, as the liquid phase, with an enzyme, for example alkaline phosphatase, it was found that the pairs 299S18-20/299S22-1 and 299S22-1/299S22-10, which are not cross-reactive, are most suitable for such quantitative assay, it being necessary for in each case the first of the monoclonal antibody pairs mentioned, which bonds weakly to eglin C, to be used as the solid phase.

The monoclonal antibodies according to the invention, as the solid phase, can also be used for the quantitative determination of eglin C together with a polyclonal anti-eglin C antibody, for example from sheep, as the liquid phase.

The sensitivity of the tandem ELISA is about 1–10 ng of eglin C/ml of a sample.

Pharmaceutical Products

The known (for example eglin B and eglin C) and novel (for exampLe Nα-acetyl-eglin B and -eglin C and methionyl-eglin C and -eglin B) eglins and modified eglins obtainable according to the present invention have useful pharmacological properties and, like the eglins extracted from leeches (cf. German Offenlegungsschrift 2,808,396), can be used prophylacticalty or, in particular, therapeuticalLy.

The novel eglin compounds according to the invention, such as $N^α$-acetyl-eglin B and $N^α$-acetyl-eglin C, are distinguished by a very potent and specific inhibition of human Leucocyte elastase (HLE), teucocyte cathepsin G (H.cat.G) and chymotrypsin. The association rate constants ($k_{ass}$) and the equilibrium constants ($K_i$) of the enzyme-inhibitor complexes formed for the reactions of $N^α$-acetyl-eglin C and two naturally occurring protease inhibitors, $α_1$-proteinase inhibitor ($^α_1$PI, previously called $^α_1$-antitrypsin) and $^α_2$-macroglobulin ($^α_2$M), with HLE and H.cat.G are summarised in the following table:

TABLE

Kinetic parameters of the interaction of selected proteinases with the inhibitors Nα-acetyl-eglin C, α, PI and $α_2$M

| Proteins | Inhibitor | $k_{ass}[M^{-1} × second^{-1}]$ | $K_i$ [M] |
|---|---|---|---|
| HLE | $α_1$PI | $1.5 × 10^7$ | irreversible |
|  | $α_2$M | $1.0 × 10^7$ | irreversible |
|  | $N^α$-Acetyl-eglin C | $1.4 × 10^7$ | $8 × 10^{-11}$ |
| H.Cat.G | $α_1$PI | $1.0 × 10^6$ | irreversible |
|  | $α_2$M | $3.5 × 10^6$ | irreversible |
|  | $N^{6α}$-Acetyl-eglin C | $2.0 × 10^6$ | $5 × 10^{-11}$ |

Conditions: The association rate constants were determined by the method of Bieth et at. (36). The $k_i$ values for the interaction of $N^α$-acetyl-eglin C with HLE and H.cat.G were catculated from "steady state" reaction rates, on the assumption that these interactions are reversible. All the values were determined at 37° C. and pH 7.4.

The data show that the association rate constants for the reaction of $N^α$-acetyl-eglin C and the natural inhibitors $α_1$PI and $α_2$M with HLE or H.cat.G are of the same order of magnitude. The high stability of the $N^α$-acetyl-eglin/enzyme complexes ($k_i$ values!), the proven extremely tow toxicity of the eglins and their specificity (no significant interactions are observed with other mammalian proteases, in particular with those of the blood coagulation, fibrinolysis and complement systems), their increased stability towards proteolytic degradation by aminopeptidases due to the N-terminal acetyl group and the easy accessibility of relatively large amounts, in comparison with the endogenous factors $^α_1$PI and $^α_2$M, with the aid of the process according to the invention recommend these compounds for pharmacological evaluation for clinical pictures characterised by tissue destruction caused by HLE.

The activity of the compounds according to the invention manifests itself, for example, in the experimental emphysema model. One hour before induction of emphysema by intratracheal administration of 0.3 mg of HLE in hamsters, 0.5 mg or 2 mg of Nα-acetyl-eglin C (to 8 animals in each case) were also administered intratracheally. In the unprotected animaLs (those which had not been pretreated with $N_α$-acetyl-eglin CO the pulmonary function tests and histological examinations carried out after two months showed severe putmonary obstructions and emphysema. In contrast, all the animals pretreated with Nα-acetyl-eglin C showed normal pulmonary functions. Histological examination of the lungs showed merely mild, local emphysematic changes in two of the eight animals from the tow dose group (0.5 mg of Nα-acetyl-eglin C); the other animals showed no changes, which demonstrates the protective action of intratracheally administered Nα-acetyl-eglin C and at the same time its low toxicity.

The novel eglin compounds according to the invention, in particular the Nα-acetyl-eglin compounds, can accordingly be used for the prophylaxis and for the therapeutic treatment of pulmonary diseases, for example pulmonary diseases caused by leucocyte elastase, such as pulmonary ephysema and ARDS ("acute respiratory distress syndrome") and mucoviscidosis, and furthermore in cases of septic shock and as antiphlogistics and antiinflammatories. The present invention also relates to the use of the novel eglin compounds according to the invention and of their pharmaceutically acceptable salts in the prophylactic and therapeutic treatment of the clinical pictures mentioned.

The invention also relates to pharmaceutical compositions containing at least one of the compounds according to the invention or pharmaceutically acceptable salts thereof, if appropriate together with a pharmaceutically acceptable excipient and/or auxiliaries.

These compositions can be used, in particular, for the abovementioned indications, where, for example, they are administered parenterally (such as intravenously or intrapulmonarily) or applied topically. The dosage depends, in particular, on the specific processing form and on the aim of the therapy or prophylaxis.

Administration is by intravenous injection or intrapulmonarily, by inhalation, for example using a Bird apparatus. Pharmaceutical products for parenteral administration in individual-dose form accordingly contain about 10 to 50 mg of the compounds according to the invention per dose, depending on the mode of administration. Besides the active ingredient, these pharmaceutical compositions usually also contain sodium chloride, mannitol or sorbitol, to establish isotonicity. They can be in freeze-dried or dissolved form, and solutions can advantageously contain an antibacterial preservative, for example 0.2 to 0.3% of methyl or ethyl 4-hydroxybenzoate.

A product for topical application can be in the form of an aqueous solution, lotion or jelly, an oily solution or suspension, or a fat-containing or, in particular, emulsion ointment. A product in the form of an aqueous solution is obtained, for example, by dissolving the active ingredients according to the invention, or a therapeutically acceptable salt thereof, in an aqueous buffer solution of pH 4 to 7.5 and, if desired, adding a further active ingredient, for example an antiinflammatory agent, and/or a polymeric adhesive, for example polyvinylpyrrolidone, and/or a preservative. The concentration of the active ingredient is about 0.1 to about 5 mg, preferably 0.25 to 1.0 mg, in 10 ml of a solution or 10 g of a jelly.

An oily administration form for topical application is obtained, for example, by suspending the active ingredients according to the invention, or a therapeutically acceptable salt thereof, in an oil, if appropriate with the addition of swelling agents, such as aluminium stearate, and/or surface-active agents (surfactants), the HLB value ("hydrophilic-lipophilic balance") of which is less than 10, such as fatty acid monoesters of polyhydric alcohols, for example glycerol monostearate, sorbitan monolaurate, sorbitan monostearate or sorbitan monooleate. A fat-containing ointment is obtained, for example, by suspending the active ingredients according to the invention, or salts thereof, in a spreadable fat base, if appropriate with the addition of a surfactant with an HLB value of below 10. An emulsion ointment is obtained by triturating an aqueous solution of the active ingredients according to the invention, or of salts thereof, in a soft, spreadable fat base with the addition of a surfactant, the HLB value of which is below 10. All these topical forms of application can also contain preservatives. The concentration of the active ingredient is about 0.1 to about 5 mg, preferably 0.25 to 1.0 mg, in about 10 g of the base.

Inhalation products for the treatment of the respiratory tract by intrapumonary administration are, for example, aerosols or sprays which can distribute the pharmacological active ingredient in the form of drops of a solution or suspension. Products in which the pharmacological active ingredient is in solution contain, in addition to this ingredient, a suitable propellant, and furthermore, if necessary, an additional solvent and/or a stabiliser. Instead of the propellant gas, it is also possible to use compressed air, in which case this can be produced as required by means of a suitable compression and expansion device.

Bird respirators which have been introduced into medicine and are known are particularly suitable for the administration; a solution of the active ingredient is here introduced into the apparatus, misted with a slight increased pressure and introduced into the lung of the respirated patient.

Depending on the age, individual condition and type of disease, the dosage for a warm-blooded organism (humans or animals) weighing about 70 kg is about 10 to about 30 mg per inhalation (once or twice daily) for intrapulmonary administration, and about 10 to about 1,000 mg per day for intravenous administration, for example also by continuous infusion.

Therapeutically active sputum and plasma concentrations which can be determined by means of immunological processes, such as ELISA, are between 10 and 100 $\mu$g/ml (about 1 to 10 $\mu$mol/l).

The invention particularly relates to the DNA sequences which are described in the examples and code an eglin or modified eglin, expression plasmids containing such DNA sequences, microorganisms transformed with such expression plasmids, monoclonal antibodies against eglins, hybridoma cells which produce such antibodies, and test kits for immunoassay containing such antibodies, the processes described in the examples for their preparation and the process described in the examples for the preparation of eglins with the aid of the transformed microorganisms, and the novel eglin compounds mentioned in the examples.

Some embodiments of the present invention which are described in the following experimental section are illustrated with the aid of the accompanying drawings.

Figure 1:
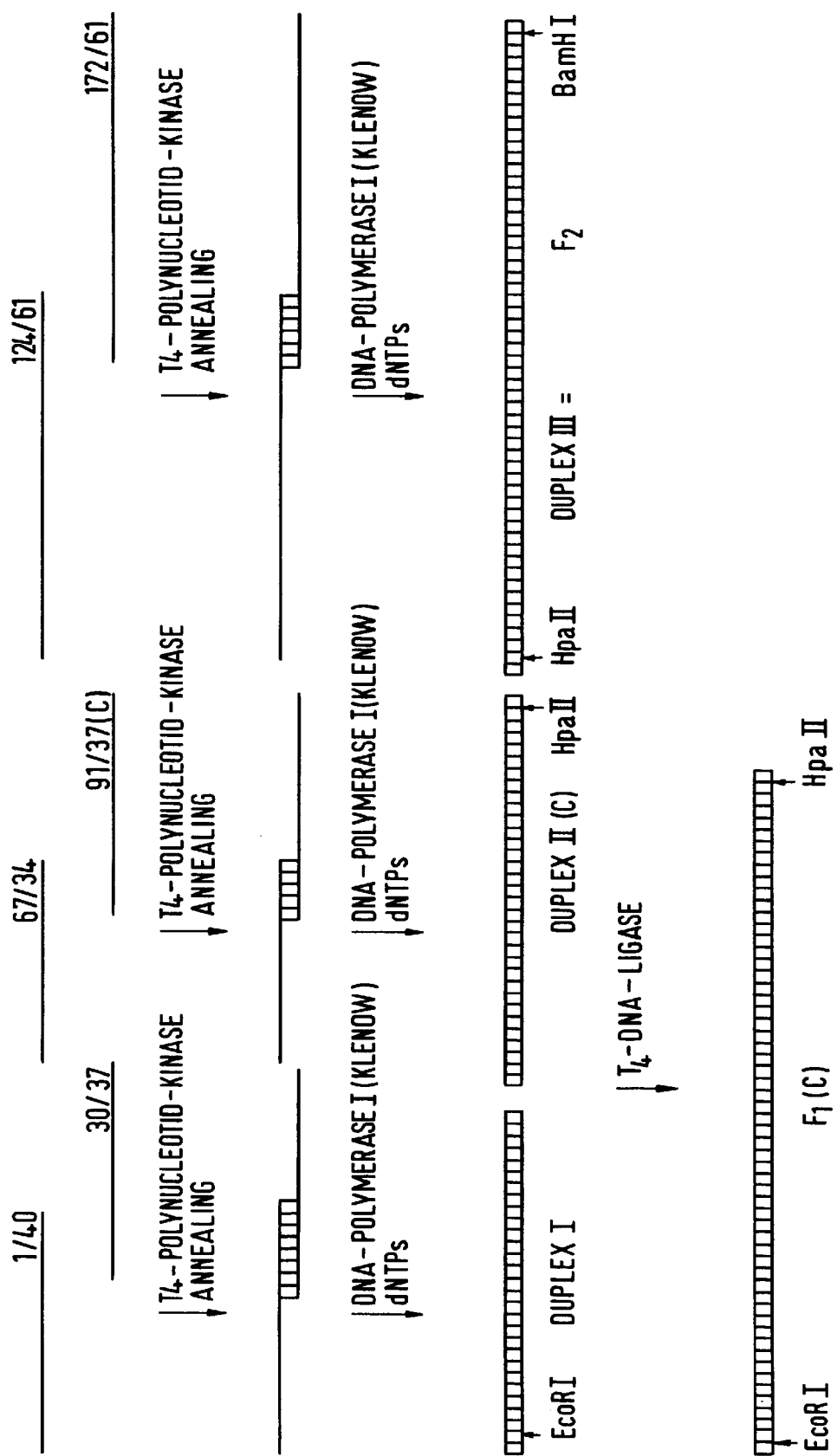
FIG. 1 represents, schematically, the synthesis of the fragments $F_1(C)$ and $F_2$ of the eglin C gene.

The following examples serve to illustrate the invention and are in no way intended to restrict it.

EXPERIMENTAL SECTION

The abbreviations used in the examples have the following meanings:

TNE Solution containing 100 mM NaCl, 50 mM tris.HCl, pH 7.5, and 5 mM EDTA
SDS Sodium dodecyl-sulfate
EDTA Ethylenediaminetetraacetic acid
DTT 1,4-Dithiothreitol (1,4-Dimercapto-2,3-butanediol)
BSA Bovine serum albumin
EtBr Ethidium bromide
Tris Tris-(hydroxymethyl)-aminomethane
Tris.HCl Monohydrochloride of tris

Example 1

Preparation of the Protected Nucleoside-polystyrene Resin

750 mg of succinic anhydride and 910 mg of 4-dimethylaminopyridine are added to 3.1 g (5 mmol) of 5'-(4-methoxytrityl)-N-benzoyl-deoxycylidine in 20 ml of absolute pyridine and the mixture is left to stand at room temperature for 16 hours. After the pyridine solution has been concentrated, the residue is taken up in 200 ml of ethyl acetate, the mixture is extracted by shaking twice with in each case 200 ml of 0.1 M phosphate buffer, with the addition of 10 ml of saturated sodium chloride solution, the extract is washed again with saturated sodium chloride solution, dried and concentrated and hexane is added dropwise to the residue. The product precipitated is separated off, triturated twice with ether and then dissolved in 300 ml of ethyl acetate and the solution is extracted by shaking at 0° C. with 180 ml of 0.1 M potassium bisulfate of pH 2.5. After washing twice with water, the ethyl acetate solution is dried with sodium sulfate and filtered, 0.5 ml of pyridine is added, the mixture is concentrated and the residue is diluted dropwise with hexane. The succinic acid derivative precipitated is filtered off.

1.17 g of this compound are dissolved in 4 ml of ethyl acetate and 2 ml of dimethylformamide, together with 190 mg of N-hydroxysuccinimide, and 370 mg of N,N'-dicyclohexylcarbodiimide are added at 0° C. After the mixture has been left to stand overnight in a refrigerator, the N,N'-dicyclohexylurea precipitated is filtered off, the filtrate is diluted with ethyl acetate and extracted with cold 0.1 M sodium bicarbonate and water and the extract is dried and evaporated to dryness in vacuo. The residue is chromatographed with ethyl acetate on silica gel. Thin layer chromatography: $R_f$=0.58 in methylene chloride/methanol (9:1).

88 mg of this N-succininidoyl-succinic acid ester are stirred with 1 g of aminomethyl-polystyrene (amine content: 110 umol/g) in 2 ml of methylene chloride and 4 ml of dimethylformamide for 20 hours. The polymer resin is filtered off and washed out with dimethylformamide, methanol, methylene chloride and methanol. After drying, the unreacted amino groups are acetylated by stirring the resin in 6 ml of pyridine with 1 ml of acetic anhydride and 100 mg of 4-dimethylaminopyridine for 30 minutes. The polymer resin is washed out with methylene chloride, dimethylformamide, methanol and methylene chloride and dried to constant weight. Determination of methoxytrityl (MMT) by spectroscopy shows a loading of 85 umol/g.

Example 2

The following protected nucteoside-polystyrene resins are prepared analogously to Example 1:

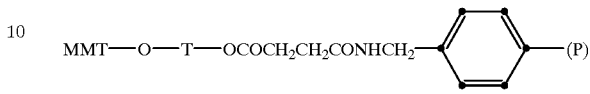

from 5'-(4-methoxytrityl)-thymidine, loading: 92 μmol/g.

from 5'-(4-methoxytrityl)-N-isobutyryl-deoxyguanosine, loading: 75 μmol/g.

Example 3

Synthesis of the Trinucleotide

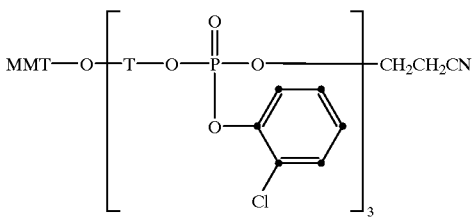

a) Synthesis of the Dinucleotide 7.73 g (15 mmol) of 5'-(4-methoxytrityl)-thymidine (MMT-O-T-OH) are evaporated twice with absolute pyridine. The residue is dissolved in 20 ml of absolute tetrahydrofuran, the solution is added dropwise to 80 ml of a 0.2 M solution of 2-chlorophenyl di-(1-benzotriazolyl) phosphate in tetrahydrofuran, with stirring and exclusion of moisture, and the reaction mixture is stirred at room temperature for 1 hour. The resulting solution of the 2-chlorophenyl 1-benzotriazotyl 5'-(4-methoxytrityl)-thymidine 3'-phosphate is divided into three.

α) Hydrolysis to triethylammonium 2-chlorophenyl 5'-(4-methoxytrityl)-thymidine 3'-phosphate 100 ml of 0.5 M triethylammonium bicarbonate are added to one-third of the above solution of 2-chlorophenyl 1-benzotriazolyl 5'-(4-methoxytrityl)-thymidine 3'-phosphate, with cooling. After 15 minutes, the mixture is extracted with methylene chloride. The methylene chloride solution is washed with water and concentrated and petroleum ether is added dropwise to the residue. The resulting precipitate is filtered off with suction, washed out with ether/petroleum ether 1:1 and dried in vacuo. Thin layer chromatography: $R_f$=0.35 in methylene chloride/methanol/water (75:22:3).

β) Esterification to 2-cyanoethyl 2-chlorophenyl 5'-(4-methoxytrityl)-thymidine 3'-phosphate and Detachment of the 4-methoxytrityl Protective Group 1.3 ml of 2-cyanoethanol and 2 ml of pyridine are added to one-third of the solution of 2-chlorophenyl 1-benzotriazolyl 5'-(4-methoxytrityl)-thymidine phosphate.

The mixture is left to stand overnight at room temperature. The solvents are distilled off in vacuo, the residue is dissolved in ethyl acetate and the solution is extracted by shaking several times with 0.1 M phosphate buffer, pH 7, and water. The organic phase is dried and concentrated and the residue is added dropwise to hexane. The precipitate is filtered off and dissolved in 50 ml of methylene chloride/methanol 7:3, and a solution of 3.8 g of p-toluenesulfonic acid monohydrate in 75 ml of methylene chloride/methanol 7:3 is added at 0° C. After 2 hours, the reaction solution is diluted with methylene chloride and extracted by shaking with a cold sodium bicarbonate solution. The organic phase is concentrated and hexane is added to the residue. The 2-cyanoethyl 2-chlorophenyl thymidine 3'-phosphate precipitated is chromatographed on silica gel with methylene chloride/methanol 96:4. Thin layer chromatography: $R_f$ of 0.45 in methylene chloride/methanol (9:1).

γ) Condensation to the 5'-(4-methoxytrityl)-3'-(2-cyanoethyl)bis-thymidine Dinucleotide 2.2 g of 2-cyanoethyl 2-chlorophenyl thymidine 3'-phosphate are dehydrated twice by evaporation with absolute pyridine, the residue is dissolved in 20 ml of absolute tetrahydrofuran and the solution is added to the remaining third of the solution of 2-chlorophenyl 1-benzotriazolyl 5'-(4-methoxytrityl)-thymidine 3'-phosphate. After 18 hours at room temperature, 10 ml of water and 200 ml of ethyl acetate are added to the reaction solution, while cooling with ice. The organic phase is washed several times with sodium bicarbonate and water, dried over sodium sulfate and concentrated to a small volume. The dinucleotide protected in the phosphate part and on the 5'- and 3'-end is precipitated by dropwise addition to ether/hexane 1:1. Thin layer chromatography: $R_f$=0.48 in methylene chloride/methanol (9:1).

b) Synthesis of the Trinucleotide 1.17 g (1 mmol) of the fully protected dinucleotide described above are dissolved in 30 ml of methylene chloride/methanol 7:3, and a solution of 1.9 g of p-toluenesulfonic acid monohydrate in 20 ml of methylene chloride/methanol 7:3 is added, while cooling with ice. After 2 hours, ice-cold sodium bicarbonate solution is added and the mixture is extracted with methylene chloride. The organic phase is dried and concentrated and the residue is added dropwise to hexane. The crude dinucleotide precipitated, with a free 5'-hydroxyl group, is chromatographed on silica gel with a gradient of 2–8% of methanol in methylene chloride. Thin layer chromatography: $R_f$=0.33 in methylene chloride/methanol (9:1). 850 mg of this 5'-hydroxy-dinucleotide and 1.06 9 of triethylammonium 2-chlorophenyl 5'-(4-methoxytrityl)-thymidine 3'-phosphate [c.f. Section a)α)] are evaporated twice with pyridine, the residue is then dissolved in 10 ml of absolute pyridine and 560 mg of mesitylenesulfonyl-3-nitro-1,2,4-triazolide (MSNT) are added. After 2 hours, 2 ml of ice-cold water are added and, after a further hour, the mixture is extracted with methylene chloride. The organic phase is washed with saturated sodium bicarbonate solution and water, dried and concentrated and ether is added to the residue. The trinucleotide precipitated is purified by chromatography on silica gel. $R_f$=0.45 in methylene chloride/methanol (9:1).

Example 4

The following protected trinucleotides of the general formula

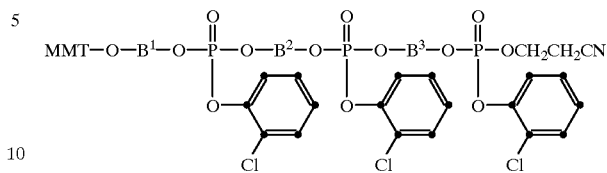

abbreviated to $B^1B^2B^3$, are prepared analogously to Example 3. The following abbreviations are used for the nucleosides $B^1B^2B^3$:
A=N-benzoyl-deoxyadenosine
C=N-benzoyl-deoxycytidine
G=N-isobutyryl-deoxyguanosine
T=thymidine

| Compound | $R_f$ [a] | Compound | $R_f$ [a] |
|---|---|---|---|
| TTT | 0.45 | ATG | 0.48 |
| TTC | 0.55 | ACT | 0.53 |
| TCT | 0.46 | ACC | 0.48 |
| TAC | 0.56 | AAT | 0.49 |
| TAA | 0.53 | AAC | 0.46 |
| TAG | 0.60 | AAA | 0.51 |
| TGT | 0.42 | AGT | 0.45 |
| TGG | 0.43 | AGA | 0.49 |
| CTG | 0.46 | GTT | 0.45 |
| CCT | 0.45 | GCT | 0.55 |
| CCG | 0.47 | GCA | 0.49 |
| CAT | 0.55 | GCG | 0.48 |
| CAA | 0.52 | GAT | 0.44 |
| CAG | 0.44 | GAC | 0.48 |
| CGT | 0.49 | GAA | 0.50 |
| GGA | 0.44 | GGT | 0.46 |

[a] Thin Layer Chromatogram on Silica Gel in Methylene Chloride/methanol 9:1

Example 5

Synthesis of the DNA Fragment 61 Bases in Length from Base No. 172 to Base No. 232 of the Complementary DNA Strand (172/61 Complementary)

a) Detachment of the 2-cyanoethyl Protective Group from the Trinucleotides

15 μmol of the trinucleotides from Example 3 or 4 are dissolved in 60 μl of pyridine/acetonitrile/triethylamine 1:1:1, with exclusion of moisture. After 1 hour at room temperature, 0.7 ml of peroxide-free ether is added dropwise and the precipitate is centrifuged off. The crude triethylammonium salt is dissolved in 50 μl of pyridine, precipitated again with 0.5 ml of ether, centrifuged off and dried under a high vacuum for 15 hours.

b) Coupling of the Partly Protected Trinucleotides with the Oligonucleotide Chain Bound to the Polystyrene Resin All the operations are carried out with the exclusion of moisture in a reaction vessel of 280 μl capacity and with microprocessor-controlled addition of solvent and reagent. 17.6 mg (1.5 μmol) of the cytidine-polystyrene resin (Example 1) are introduced into the reaction vessel and subjected to the following operations:
1. Methylene chloride, 2 ml/minute, 5 minutes.
2. Methylene chloride/isopropanol (85:15), 2 ml/minute, 2 minutes.
3. 1 M zinc bromide and 0.02 M 1,2,4-triazole in methylene chloride/isopropanol (7:3), 1 ml/minute, 2–3.5 minutes.

4. Methylene chloride/isopropanot (85:15), 2 ml/minute, 3 minutes.
5. 0.5 M triethylammonium acetate in dimethylformamide, 2 ml/minute, 10 minutes.
6. Pyridine dried by molecular sieve, 2 ml/minute, 5 minutes.
7. Tetrahydrofuran (peroxide-free, dried by molecular sieve), 2 ml/minute, 5 minutes.
8. Stream of nitrogen, 10 minutes.
9. Injection of 15 μmol of trinucleotide AAA (trimethylammonium salt from Section a)) and 13.3 mg (45 μmol) of mesitylenesulfonyl-3-nitro-1,2,4-triazotide (MSNT), dissolved in 160 μl of pyridine.
10. 40° C., 30 minutes.
11. Pyridine, 2 ml/minute, 5 minutes.
12. 5% acetic anhydride and 2.5% 4-dimethylaminopyridine in pyridine, 2 ml/minute, 5 minutes.
13. Pyridine, 2 ml/minute, 5 minutes.
14. Pyridinelisopropanol (1:1), 2 ml/minute, 3 minutes.

All the 14 operations are repeated 19 times, in each case the following trinucleotides being used in the form of their triethylammonium salts (Section a)) in the 9th operation instead of AAA: AGA, TGT, GGT, CTG, TAC, TAG, CGT, CAA, TAA, GGT, CAT, GAA, GCG, CAT, CAA, AAC, CCT, GAT, CAG. The average coupling yield is 96%. The end product has the following structure:
MMT-CAGGATCCTAACCAACATGCGGAACATGGTTAAC AACGTTAGTACCTGGGTTGTAGAAAAC-polystyrene.

c) Detachment of the DNA Fragment from the Carrier and Detachment of the Protective Groups 40.2 mg (about 0.66 μmol) of DNA synthesis resin/172/61 complementary are kept at 50° C. for 3 hours and at room temperature for 12 hours with 66 mg (0.40 mmol) of o-nitrobenzaldoxime and 50 μl (0.40 mmol) of 1,1,3,3-tetramethylguanidine in 400 μl of 95% pyridine. After the pyridine has been blown off with nitrogen, 1.6 ml of aqueous ammonia (33%) are added to the residue and the mixture is kept in a closed vessel at 50° C. for 24 hours.

The liquid phase separated off is freed from the ammonia in vacuo and washed 3 times with 3 ml of peroxide-free diethyl ether each time. After the low molecular weight constituents have been removed on a Biogel P6 column (100–200 mesh, 3×66 cm, 0.01 molar trimethylammonium bicarbonate, pH 7.5, 1.5 ml/minute), 285 ODs (260 nm) of DNA are isolated.

A total of 60 ODs are separated on a HPLC column (PRP-1/Hamitton, 250×4.6 mm). Gradient (solution A: 0.05 M triethylammonium acetate, pH 7.0; solution B: solution A/acetonitrile 1:1): 30% of B in A→60% of B in A in 20 minutes at 50° C. and 2 ml/minute. The main lipophilic peak (retention time about 14 minutes) is collected, concentrated on a DE52-cellulose (Whatman) column, eluted and precipitated with ethanol. To detach the 4-methoxytrityl protective group, the precipitate is dissolved in 50 μl of acetic acid/H$_2$O (4:1) and the solution is kept at room temperature for 45 minutes. The reaction product is lyophitised, precipitated with ethanol and, for purification, separated electrophoretically on an 8% polyacrylamide gel (7 M urea). The band corresponding to the expected DNA size is cut out and the product electroetuted and concentrated on DE52-cellulose, and the DNA having the structure 5'-CAGGATCCTAACCAACATGCGGAACATGGTTAA CAACGTTAGTACCTGGGTTGTAGAAAAC-3' is precipitated with ethanol.

Example 6

The following DNA fragments (5'-3') are prepared analogously to Example 5:
1/40
CTGGAATTCATGACTGAATTTGGTTCT-GAACTGAAATCTT
30/37 complementary
AACAGTTTTACCAACAACTTCTGGGAAA-GATTTCAGT
67/34
GACCAGGCTCGTGAATACTTCACTCTGCATTACC
91/37 complementary (C)
CCGGCAGGAAGTAAACGTCGTACT-GCGGGTAATGCAG
91/37 complementary (B)
CCGGCAGGAAATGAACGTCGTACT-GCGGGTAATGCAG
124/61
CCGGAAGGTTCTCCTGTTACTCTGGAC-CTGCGTTACAACCGTGTTCGTGTTTTCTACAACC The following shortened fragments are also prepared:

1/40 (Δ12) (C')
CTGGAATTCATGTCTGAACTGAAATCTT

1/40 (Δ18) (C")
CTGGAATTCATGCTGAAATCTT

Example 7

Phosphorylation of the Fragments 30/37, 67/34, 124/61 and 172/61

The phosphorylation and the radioactive labelling on the 5'-ends are carried out with [-$^{32}$P]ATP and T$_4$ polynucleotide kinase (Boehringer) as described (19).

Example 8

Polymerisation to the Duplex III (Fragment F$_2$ of the Eglin C and Eglin B Gene)

In each case 50 mol of fragment 124/61/kinased and fragment 172/61/kinased are dissolved in 24 μl of water and the solution is warmed at 90° C. for 3 minutes and cooled to 12° C. in the course of 5 minutes. After addition of 4 1 of Endo-R buffer (0.1 molar tris.HCl, pH 7.5, 66 mM MgCl$_2$, 66 mM-mercaptoethanot and 0.6 M NaCl), 10 μl of deoxynucleoside triphosphate mixture (dATp, dCTp, dGTp and TTP, in each case 2×10$^{-3}$ molar, brought to pH 7.0 with NH$_3$) and 2 μl (10 units) of DNA-potymerase I, Klenow fragment (Boehringer), the mixture is incubated at 12° C. for 30 minutes. The reaction is stopped by heating the mixture at 90° C. for 3 minutes and the mixture is kept at −80° C. until further processing.

Fragments 1/40 and 30/37, 67/34 and 91/37 (C) or 67/34 and 91/37 (B) are polymerised analogousty to give the duplexes I, II(C) and II (B).

Duplexes I–III have the following structures:
Duplex I

CTGGAATTCATGACTGAATTTGGTTCT-
GAACTGAAATCTTTCCCAGAAGTTGTTG-
GTAAAACTGTTGACCTTAAGTACTGACT-
TAAACCAAGACTTGACTTTAGAAAGGGTCTTCAACA
ACCATTTTGACAA

Duplex II(C)

```
GACCAGGCTCGTGAATACTTCACTCTG-
   CATTACCCGCAGTACGACGTTTACTTC-
   CTGCCGGCTGGTCCGAGCACTTAT-
   GAAGTGAGACGTAATGGGCGTCATGCTGCAAATG
   AAGGACGGCC
```

Duplex II (B)

```
GACCAGGCTCGTGAATACTTCACTCTG-
   CATTACCCGCAGTACGACGTTCATTTC-
   CTGCCGGCTGGTCCGAGCACTTAT-
   GAAGTGAGACGTAATGGGCGTCATGCTGCAAGTAAA
   GGACGGCC
```

Duplex III (fragment $F_2$ of the eglin C and eglin B gene)

```
CCGGAAGGTTCTCCTGTTACTCTGGAC-
   CTGCGTTACAACCGTGTTCGTGTTTTC-
   TACAACCCAGGTACGGCCTTCCAAGAG-
   GACAATGAGACCTGGACGCAATGTTGGCACAAGC
   ACAAAAGATGTTGGGTCCATG TAACGTTGTTAACCAT-
   GTTCCGCATGTTGGTTAGATCCTGATTG-
   CAACAATTGGTACAAGGCGTACAACCAATCCTAGGAC
```

Fragments 1/40 (Δ12) (C") and 30/37 and fragments 1/40 (Δ18) (C") and 30/37 are polymerised in the same manner to give the duplexes I (C') and I (C").
Duplexes I (C') and I (C") have the following structures:
Duplex I (C')

```
CTGGAATTCATGTCTGAMCT-
   GAAATCTTTCCCAGAAGTTGTTGG-
   TAAAACTGTTGACCTTMGTACAGACT-
   TGACTTTAGAAAGGGTCTTCAACAACCATTTTGACAA
```

Duplex I (C")

```
CTGGAATTCATGCTGAAATCTTTCCCA-
   GAAGTTGTTGGTAAAACTGTTGACCTT-
   MGTACGACTTTAGAAAGCGTCTTCAA-
   CAACCATTTTGACA
```

Example 9

Ligation of Duplex I with Duplex II (C),
Preparation of the Fragment $F_1$ (C) of the Eglin C Gene In each case 60 pmol of duplex I and duplex II (C) (cf. Example 8; only kinased on the A and G 5'-ends) are dissolved in 54 ul of ligase buffer (66 mM tris.HCl, pH 7.5, 6.6 mM MgCl$_2$, 10 mM dithiothreitol and 5 mM ATP), 6 μl (=6 units) of $T_4$-DNA-ligase (Boehringer) are added and the mixture is incubated at 20° C. for 21 hours. The reaction is stopped by heating at 70° C. for 5 minutes and the DNA is isolated by ethanol precipitation, after phenol/chloroform extraction.

After the mixture has been separated by electrophoresis on an 8% polyacrylamide gel (natural), the ligation products with 122–132 base pairs are electroetuted, concentrated on a DE52-cellutose column and, after elution, isolated by ethanot precipitation.

Fragment $F_1$ (C) of the eglin C gene has the following structure:

```
CTGGAATTCATGACTGAATTTGGTTCT-
   GAACTGAAATCTTTCCCAGAAGTTGTTG-
   GTAAAACTGTTGACCTTAAGTACTGACT-
   TAAACCAAGACTTGACTTTAGAAAGGGTCTTCA
   ACAACCATTTTGACAA GACCAGGCTCGTGAATACT-
   TCACTCTGCATTACCCGCAGTAC-
   GACGTTTACTTCCTGCCGGCTGGTC-
   CGAGCACTTATGAAGTGAGACGTAATGGGCGTC
   ATGCTGCAA
   ATGAAGGACGGCC
```

In each case 60 pmol of duplex I (C') or I (C") and duplex II are linked in an analogous manner to give the fragments $F_1$ (C') and $F_1$ (C") of the shortened eglin C gene.

The fragments $F_1$ (C') and $F_1$ (C") have the following structures:

```
CTGGAATTCATGTCTGAACT-
   GAAATCTTTCCCAGAAGTTGTTGG-
   TAAAACTGTTGACCTTAAGTACAGACT-
   TGACTTTAGAAAGGGTCTTCAACAACCATTTTG
   ACAAGACCAGGCTCGTGAATACT-
   TCACTCTGCATTACCCGCAGTAC-
   GACGTTTACTTCCTGCCGGCTGGTC-
   CGAGCACTTATGAAGTGAGACGTAATGGGC
   GTCATGCTGCAAATGAAGGACGGCC             $F_1$(C')
CTGGAATTCATGCTGAAATCTTTCCCA-
   GAAGTTGTTGGTAAAACTGTTGACCT-
   TAAGTACGACTTTAGAAAGGGTCTTCA-
   CAACCATTTTGACAAGACCAGGCTCGTGAATAC
   TTCACTCTGCATTACCCGCAGTAC-
   GACGTTTACTTCCTGCCGGCTGGTC-
   CGAGCACTTATGAAGTGAGACG-
   TAATGGGCGTCATGCTGCAAATGAAGGACGGCC   $F_1$(C")
```

Example 10

Ligation of Duplex I with Duplex II (B),
Preparation of the Fragment $F_1$ (B) of the Eglin B Gene In each case 60 pmol of duplex I and duplex II (B) are ligated with one another in a manner analogous to that described in Example 9.

Fragment $F_1$ (B) of the eglin (B) gene has the following structure:

```
CTGGAATTCATGACTGAATTTGGTTCT-
   GAACTGAAATCTTTCCCAGAAGTTGTTG-
   GTAAAACTGTTGACCTTAAGTACTGACT-
   TAAACCAAGACTTGACTTTAGAAAGGGTCTT
   CAACAACCATTTTGACAA GACCAGGCTCGTGAATACT-
   TCACTCTGCATTACCCGCAGTACGACGT-
   TCATTTCCTGCCGGCTGGTCCGAGCACT-
   TATGAAGTGAGACGTAATGGGCGTCATGCTGCAAG
   TAAAGGACGGCC
```

Example 11

Figure 2:
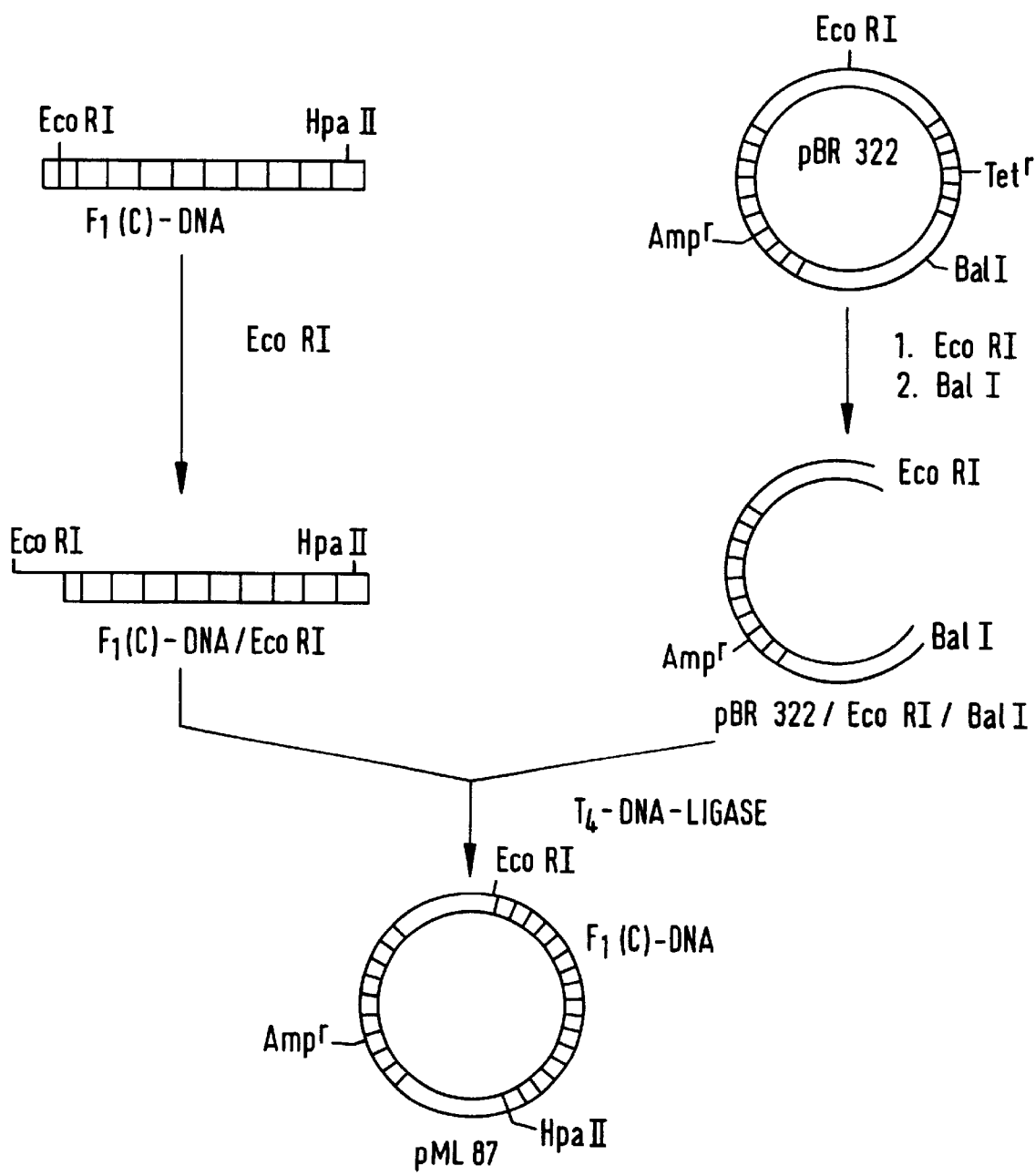
FIG. 2 shows the preparation of the plasmid pML 87, the cloning vector for the fragment $F_1(C)$ of the eglin C gene.

Preparation of the Plasmid pML87, Containing the $F_1$ (C)-DNA of the Eglin C Gene (FIG. 2)

a) Preparation of the Linearised Vector pBR322/EcoRI/BalI
30 μg of pBR322 plasmid-DNA are digested with 5 units of BalI restriction endonuclease (Biolabs) in 200 ml of a solution of 100 μg/ml of gelatine at 37° C. for 5 hours. This solution is then brought to 100 mM tris.HCl (pH 7.5) and 50 mM NaCl, and the DNA is digested with 30 units of EcoRI restriction endonuclease (Biolabs) for 2 hours at 37° C. The solution is then brought to TNE and extracted with 1 volume of phenol and chloroform, and the digested DNA is precipitated with 2 volumes of alcohol at −20° C. overnight.

The vector excised from the pBR322 DNA (pBR322/ecoRI/BalI, 2,916 base pairs) is separated off from the small DNA fragment (1,445 base pairs) by density gradient centrifugation in sucrose (5–23%) in 50 mM tris.HCl (pH 8) and 1 mM EDTA. The centrifugation is carried out at 36,000 rpm in a TST 41 rotor (Kontron AG) at 15° C. for 16 hours. 0.2 ml fractions of the centrifuged solution are then obtained with a ISCO gradient collector. Those fractions which contain the large DNA fragment (2,916 base pairs) are combined and the DNA is precipitated with alcohol. The precipitate is dissolved in 100 μl of 10 mM tris.HCl (pH 8) and 0.1 mM EDTA and kept at −20° C. until used as a cloning vector. 5.1 μg (=10.5 pmol of ends) of DNA are obtained.

b) Preparation of $F_1$ (C)-DNA/EcoRI
16 ng (=0.84 pmol of ends) of the chemically synthesised $F_1$ (C)-DNA (cf. Example 9) are digested with 5 units of EcoRI restriction endonuclease (Biolabs) in 50 μl of 100 mM tris.HCl (pH 7.5), 50 mM NaCl and 10 μg/ml of gelatine at 37° C. for 1 hour. 0.5 μg (=1 pmol of ends) of the linearised vector pBR322/EcoRI/BalI (Example 11a) is then added to the solution. The enzyme is then inactivated by heating at 65° C., after 10 minutes, and the solution is brought to TNE and extracted with phenol/chloroform. The DNA is precipitated with alcohol. The DNA precipitated is kept under alcohol at −20° C. until further processing.

c) Ligation of the pBR322/EcoRI/SalI vector-DNA with $F_1$(C)-DNA/EcoRI and Construction of the Plasmid pML87.

The DNA precipitate obtained in Example 11b), which contains the two DNA fragments mentioned, is dissolved in 30 μl of a solution of 50 mM tris.HCl (pH 7.8), 10 mM $MgCl_2$, 10 mM DTT, 0.5 mM ATP and 100 μg/ml of gelatine and the solution is treated with 15 units/μl of $T_4$ DNA-ligase (Biolabs) at 15° C. for 16 hours. The recombinant plasmid pML87 containing the $F_1$ (C)-DNA is formed in the solution in this manner.

d) Transformation of E. coli HB101 with the Plasmid pML87

The E. coli HB101 cells pretreated with calcium which are required for the transformation are prepared as described by Mandel et at. (6).

The solution obtained under c), which contains the recombinant plasmid pML87, is heated at 65° C. for 10 minutes in order to inactivate the $T_4$-DNA-ligase, and is then cooled to 37° C. 10 μl of this reaction mixture are added to 150 μl of calcium-treated E. coli HB101 celts in 10 mM $MgCl_2$ and 10 mM tris.HCl (pH 7.5) in a total volume of 200 μl.

This mixture is then cooled in ice for 30 minutes, warmed at 42° C. for 2 minutes and then left to stand in 1 ml of L medium (cf. Example 21) at 37° C. for 50 minutes. The mixture is then brushed in aliquot portions of 0.2 ml onto 5 agar plates (McConkey agar, Difco), containing 60 μg/ml of ampicillin (Serva). The agar ptates are then kept at 37° C. for 16–18 hours. 470 ampicillin-resistant colonies of the transformed E. coli HB101 are obtained.

e) Screening of the Colonies Containing $F_1$ (C)-DNA 470 transformed colonies (Example 11d) are transferred onto nitrocellulose filters B85(Schleicher and Schüll). By the method of Grunstein and Hogness (24), the colonies are lysed and their denatured DNA is fixed on the filter. The filters are then prehybridised in 20 ml (per filter) of 4×SET, [=solution of 30 mM tris.HCl (pH 8), 150 mM NaCl and 1 mM EDTA], 0.1% (g/v) of Ficoll 400 (Pharmacia), 0.5% of SDS and 50 μg/ml of denatured calf thymus-DNA at 64° C. for 4 hours. The nitrocellulose fitters are then treated in 20 ml (per filter) of 5×SET . . . (g/v) of Ficoll 400, 0.2% of SDS and 50 μg/ml of denatured calf thymus-DNA at 64° C. for 16 hours with the $^{32}$P-radioactively labelled probe (about $10^3$–$10^4$ Cerencov cpm per filter). The oligonucleotide 93/37 complementary (C) (cf. Example 6) is used as the probe.

The filters are then washed twice in 2×SET and 0.2% of SDS at room temperature, and then twice in 2×SET and 0.5% of SDS at 60° C. (first for 30 minutes and then for 60 minutes). The fitters are then dried between 3 MM paper (Whatman) and placed on an X-ray film (Fuji) with an intensifying screen (Ilford) at −80° C. for 1–2 days.

The resulting autoradiogram shows 71 positive colonies (clones), which can be used for further processing; one of these has the designation pML 87.

In an analogous manner, the chemically synthesised $F_1$ (C')-DNA or $F_1$ (C")-DNA (cf. Example 9) is digested with EcoRI and ligated with the linearised vector pBR322/EcoRI/ BalI, the plasmid pML87 (C'), containing the $F_1$ (C)-DNA, or the plasmid pML87 (C"), containing the $F_1$ (C")-DNA, being formed. E. coli HB101 cells are transformed with the plasmid pML87 (C') or pML87 (C") and cultured on agar plates containing ampicillin. 95 or, respectively, 120 ampicillin-resistant colonies are obtained. Screening of the transformed colonies with the oligonucleotide 91/37 complementary (C) Leads to identification of 37 colonies containing the $F_1$ (C')-DNA, or 58 colonies containing the $F_1$(C")-DNA.

Example 12

Preparation of the Plasmid pML90, Containing the $F_1$(B)-DNA of the Eglin B Gene In a manner analogous to that described in Example 11b), 16 μg of the chemically synthesised $F_1$ (B)-DNA are digested with 5 units of EcoRI restriction endonuclease and mixed with the linearised vector pBR322/EcoRI/BalI. The enzyme is inactivated and the DNA is precipitated with alcohol. The DNA precipitate is treated with $T_4$ DNA-ligase according to Example 11c), a plasmid containing the $F_1$ (B)-DNA being formed.

The solution containing recombinant plasmids is used in accordance with Example 11d) for the transformation of calcium-treated E. coli HB101 cells. 310 ampicillin-resistant colonies of the transformed E. coli HB101 are obtained.

Analogously to Example 11e), the 310 colonies are tested for the presence of $F_1$ (B)-DNA, the oligonucleotide 91137 complementary (B) being used as the probe. 55 positive clones which can be used for further processing are recognisable in the resulting autoradiogram. One of these was given the designation pML90.

Example 13

Figure 3:
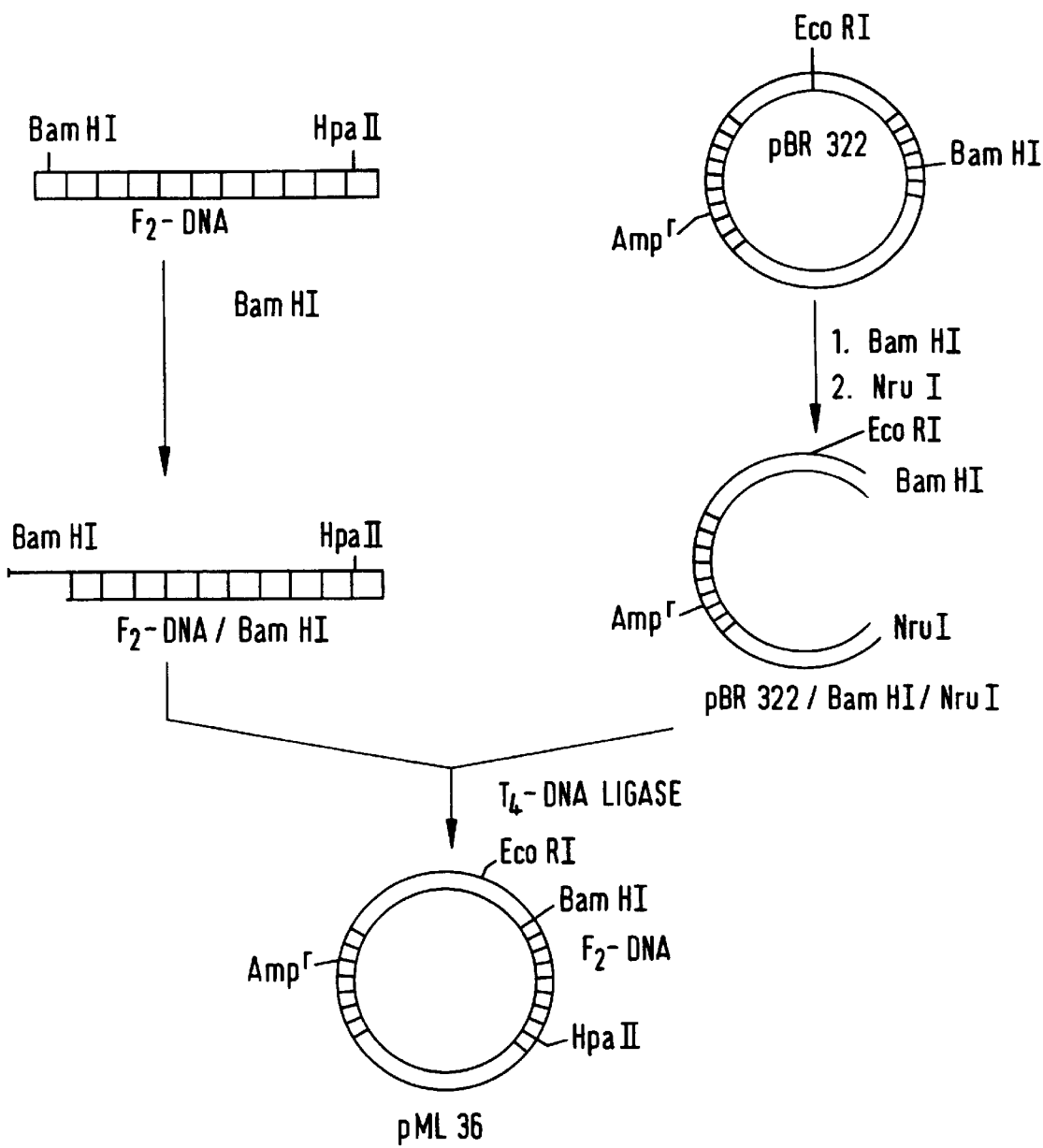
FIG. 3 correspondingly shows the preparation of the plasmid pML136, the cloning vector for the fragment $F_2$ of the eglin C or eglin B gene.

Preparation of the Plasmid pML136 Containing the $F_2$-DNA (FIG. 3)

a) Preparation of the Linearised Vector pBR322/BamHI/ NruI 15 ug of pBR322 plasmid-DNA are digested with 30 units of BamHI restriction endonuclease for 30 minutes at 37° C. in a solution of 100 mM NaCl, 6 mM tris.HCl (pH 7.9), 6 mM $MgCl_2$ and 100 μg/ml of gelatine. 15 units of NruI restriction endonuclease are then added to the solution and digestion is carried out for 2 hours at 37° C.

The reaction mixture is warmed at 70° C. for 10 minutes in order to inactivate the enzymes. Thereafter, the two DNA fragments are separated from one another by get electrophoresis on a 1% low-melting agarose in tris-acetate EDTA buffer, pH 8. After the DNA in the agarose gel has been stained with EtBr, the site of the gel containing the DNA band of the pBR322/BamHI/NruI vector (=3,766 base pairs) is cut out of the gel and liquefied at 65° C. for 10 minutes. 2 volumes of 100 ml tris.HCl (pH 8.7) are then added to the liquefied piece of agarose gel and the mixture is cooled to 37° C. This DNA mixture is digested with 0.5 unit of alkaline phosphatase from the calf intestine (Boehringer) for 30 minutes at 37° C. The enzyme is inactivated by heating the solution at 65° C. for 60 minutes.

20 volumes of TNE are added to this phosphatase-treated DNA solution and the DNA is purified, in accordance with the method of Mueller et al. (23), by DE-52 chromatography and extracted with phenol/chloroform, and the DNA is precipitated with alcohol at −20° C. overnight. The DNA precipitate is dissolved in 50 μl of 0.01 M tris.HCl (pH 8) and 0.1 mM EDTA and is kept at −20° C. until used. 1.5 μg (=2.4 pmol of ends) of DNA are obtained.

b) Preparation of the $F_2$-DNA/BamHI 1.6 µg (=90 pmol of ends) of the chemically synthesised $F_2$-DNA (Example 8) are digested with 16 units of BamHI restriction endonuclease (Biolabs) in 20 µl of 150 mM NaCl, 6 mM tris.HCl (pH 7.9), 6 mM $MgCl_2$ and 100 µg/ml of gelatine at 37° C. for 30 minutes. 60 ng (=96 nmol of ends) of the linearised vector pBR322/BamHI/NruI (Example 13a) are then added to the solution, the entire solution is brought to TNE and extracted with phenol/chloroform and the DNA is precipitated with 2 volumes of alcohol. The DNA precipitated is kept under alcohol at −20° C. until further processing.

c) Ligation of the pBR3221BamHI/NruI Vector-DNA with the $F_2$-DNA/BamHI and Construction of the Plasmid pML136

The DNA precipitate obtained under Example 13b), which contains the two DNA fragments mentioned, is dissolved in 20 µl of a solution of 50 mM tris.HCl (pH 7.8), 10 mM $MgCl_2$, 10 mM DTT, 0.5 mM ATP and 100 µg/ml of gelatine and the solution is treated with 15 units/µl of $T_4$ DNA-ligase (Biolabs) at 15° C. for 3 hours. The recombinant plasmid pML136 containing the $F_2$-DNA is formed in the solution in this manner.

d) Transformation of E. coli HB101 with the Plasmid pML136

Transformation of the calcium-treated E. coli HB101 cells is carried out as described in Example 11d). 10 µl of the reaction mixture obtained in Example 13c) are used. 65 ampicillin-resistant colonies are obtained.

e) Screening of the Colonies Containing the $F_2$-DNA 65 transformed colonies (Example 13d) are tested for $F_2$-DNA as described in Example 11e). The oligonucleotide 172/61 complementary (cf. Example 5) is used as the radioactive probe. 2 positive colonies are obtained in the autoradiogram, one of which has the designation pML136.

Example 14

Characterisation of the Clones pML87, pML90 and pML136

The DNAs of the recombinant plasmids pML87, pML90 and pML136 are isotated by the Ish-Horowitz method (25). The nucleotide sequences of the $F_1$(C)-DNA, $F_1$(B)-DNA and $F_2$-DNA inserts are determined by the method of Maxam and Gilbert (3). For this purpose, in each case 10 µg of plasmid-DNA of pML87 and pML 90 are cleaved with EcoRI restriction endonuclease and 10 µg of plasmid-DNA from pML136 are cleaved with BamHI restriction endonuclease, and the linearised DNAs are isolated by get elution from agarose get [cf. Examples 11a) and 13a)]. The isolated DNAs are then digested with alkaline phosphatase and chromatographed over DE-52 (cf. Example 13a). Thereafter, the DNAs are radioactively labelled on the 5'-ends with [α-$^{32}$P]ATP (specific activity>5,000 Ci/mmol, Amersham) and $T_4$-polynucleotide kinase (P-L-Biochemicals).

The radioactively labelled DNAs are then cleaved with a second restriction endonuclease (PvuII). The DNA fragments formed are isolated by get elution from agarose. In the case of pML87 and pML90, the nucleotide sequence of the F1 (C)-or $F_1$(B)-DNA of the PvuII-EcoRI* fragment (about 2,190 base pairs) and in the case of pML136 the nucleotide sequence of the $F_2$-DNA in the PvuII-BamHI* fragment (about 1,815 base pairs) is then determined. (* indicates the DNA end which is radioactively labelled).

The nucleotide sequences determined for the $F_1$ (C)-DNA, $F_1$ (B)-DNA and $F_2$-DNA are identical to those shown in Examples 8–10.

Example 15

Figure 4:
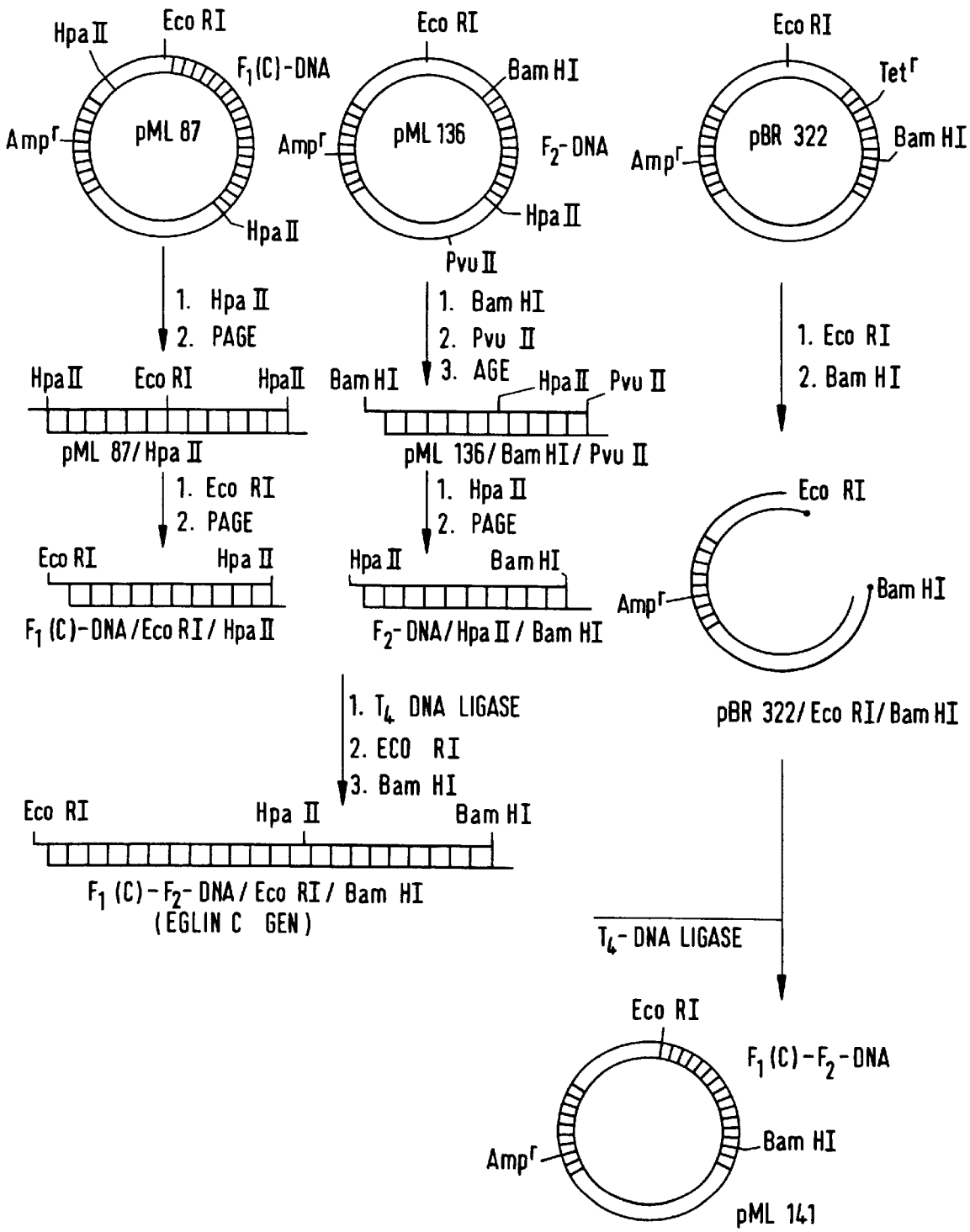
FIG. 4 illustrates the construction of the cloning vector pML141, which contains the $F_1(C)$-$F_2$-DNA.

Preparation of the Plasmid pML141 Containing the $F_1$ (C)-$F_2$-DNA (FIG. 4)

a) Preparation of the Linearised Vector pBR322/EcoRI/BamHI

10 µg of pBR322 plasmid-DNA are digested with in each case 10 units of EcoRI and BamHI restriction endonuclease (Biolabs) in 100 µl of a solution of 50 mM tris.HCl (pH 7.5), 50 mM NaCl, 6 mM $MgCl_2$ and 100 µg/ml of gelatine at 37° C. for 1 hour. This solution is then brought to TNE and extracted with 1 volume of phenol and chloroform, and the DNA is precipitated with 2 volumes of alcohol at −20° C. overnight.

The vector (pBR322/EcoRI/BaII, 3,986 base pairs) excised from the pBR322-DNA is separated off from the smaller DNA fragment (376 base pairs) by density gradient centrifugation in sucrose (5–23%) in 50 mM tris.HCl (pH 8) and 1 mM EDTA. The centrifugation is carried out at 30,000 rpm in a TST 41 rotor (Kontron AG) at 15° C. for 15 hours. 0.2 ml fractions are then obtained from the centrifuged solution with a ISCO gradient collector. Those fractions which contain the large DNA fragment (3,986 base pairs) are combined and the DNA is precipitated with alcohot. The precipitate is digested in 100 µl of 50 mM tris.HCl (pH 8) with 0.3 unit of alkaline phosphatase from the calf intestine (Boehringer) at 37° C. for 30 minutes. The enzyme is inactivated by heating the solution to 65° C. for 1 hour. The solution is then extracted with phenol/$CHCl_3$ and the DNA is precipitated with alcohol overnight at −20° C. The precipitate is dissolved in 50 µl of 10 mM tris.HCl (pH 8) and 0.1 mM EDTA and kept at −20° C. unit used as a cloning vector. 3.75 µg of DNA (=5.7 pmol of ends) are obtained.

b) Preparation of the $F_1$ (C)-DNA/EcoRI/HpaII and the $F_2$-DNA/BamHI/HpaII

I. Preparation of the $F_1$ (C)-DNA/EcoRI/HpaII 10 ug of plasmid-DNA of pML87 are first digested with 20 units of HpaII restriction endonuclease in 100 µl of a solution of 10 mM tris.HCl (pH 7.4), 6 mM KCl, 10 mM $MgCl_2$, 1 mM DTT and 100 µg/ml of gelatine. Phenol/chloroform extraction of the solution and precipitation of the resulting DNA fragments with alcohol at −20° C. follow.

The DNA fragment mixture is then separated by electrophoresis on a 6% polyacrylamide get in tris-acetate/EDTA buffer, pH 8. The largest DNA fragment (=586 base pairs) is isolated by get elution and then cleaved with EcoRI restriction endonuclease (cf. Example 11a). The DNA fragment mixture formed is again subjected to electrophoresis on 8% polyacrylamide. 40 ng of $F_1$(C)-DNA/EcoRI/HpaII (127 base pairs) are isolated.

II) Preparation of the $F_2$-DNA/BamHI/HpaII

20 µg of plasmid-DNA from pML136 are cleaved with 20 units of BamHI restriction endonuclease. An aliquot portion (1 µg) of this linearised plasmid-DNA/BamHI is isolated by gel elution from an agarose gel (cf. Example 13a) and radioactively labelled with [α-$^{32}$P]ATP (cf. Example 14). Most of the plasmid-DNA/BamHI is then mixed with this radioactively labelled DNA, digestion is carried out with PvuII restriction endonuclease and the PvuII-BamHI*-DNA fragment (1,203 base pairs) is isolated after gel electrophoresis on 1% agarose. 14 µg of the PvuI-BamHI* fragment are digested with HpaII restriction endonuclease (see above), the DNA mixture is then separated by electrophoresis on 8% polyacrylamide get and 150 ng of the $F_2$-DNA/BamHI*/HpaII (109 base pairs) are isolated by gel elution.

c) Ligation of the $F_1$ (C)-DNA with the $F_2$-DNA and Construction of the Plasmid pML141

10 ng (=473 nmol of ends) of $F_1$(C)-DNA/EcoRI/HpaII and 9 ng (=495 nmol of ends) of $F_2$-DNA/BamHI/HpaII are treated in a volume of 20 μl with $T_4$-DNA-ligase, as already described under Example 13c). The mixture is then extracted with phenol/chloroform and the DNA is precipitated with alcohol. The DNA precipitate is then dissolved as described in Example 13a) and digested with EcoRI and BamHI restriction endonuclease. The solution is subsequently brought to TNE, and 30 ng (=50 nmol of ends) of the vector-DNA pBR322/EcoRI/BamHI (cf. Example 15a) are added. The solution is then again extracted with phenol/chloroform and the DNA is precipitated with alcohol. The DNA mixture precipitated is treated with $T_4$-DNA-ligase (Biolabs) as described in Example 13c). Recombinant plasmids containing the $F_1$ (C)-$F_2$-DNA (eglin C gene) as an insert are formed in the solution in this manner.

d) Transformation of *E. coli* HB101 with the Plasmid pML141

Calcium-treated *E. coli* H8101 cells are transformed as described in Example 11d). 10 μl of the reaction mixture obtained in Example 15c) are used. 2,586 ampicillin-resistant colonies are obtained.

e) Screening of the Colonies Containing $F_1$ (C)-$F_2$-DNA 18 transformed colonies (Example 15d) are tested for their $F_1$ (C)-$F_2$-DNA content as described in Example 11e). A mixture of the oligonucleotides described in Examples 5 and 6 is used as the radioactive probe. 13 positive colonies are obtained in the autoradiogram, four of which have the designation pML141, pML143, pML144 and pML145.

In an analogous manner, the plasmid pML87 (C') or pML87 (C") is cleaved with the restriction endonucleases HpaII and EcoRI, the $F_1$ (C')-DNA/EcoRI/HpaII or $F_1$(C")-DNA/EcoRI/HpaII formed are ligated with the $F_2$-DNA/BamHI/HpaII and the $F_1$ (C')-Fz-DNA/EcoRI/BamHI or $F_1$ (C")-F2-DNA/EcoRI/BamHI formed are ligated with the linearised vector pBR322/EcoRI/BamHI. The resulting plasmids, which contain the $F_1$ (C')-$F_2$-DNA or the $F_1$(C")-$F_2$-DNA, are used for transformation of calcium-treated *E. coli* HB101 cells. Culture of the transformed cells gives 850 or, respectively, 585 ampicillin-resistant colonies. The transformed colonies are tested with the oligonucleotide 91/37 complementary (C) for the presence of $F_1$ (C')-$F_2$-DNA or $F_1$ (C")-$F_2$-DNA. 18 colonies containing $F_1$(C')-$F_2$-DNA and 31 colonies containing $F_1$ (C")-$F_2$-DNA are identified. In each case one colony is selected and has the designation pML141 (C') or pML141 (C").

Example 16

Preparation of the Plasmid pML 160 Containing the $F_1$ (B)-$F_2$-DNA a. Preparation of the $F_1$(B)-DNA/EcoRI/HpaII In an analogous manner as that described for the $F_1$ (C)-DNA/EcoRI/HpaII (Example 15bI), 10 μg of plasmid-DNA from pML90 are cleaved first with HpaII and then with EcoRI. The fragment mixture is purified by PAGE, as described.

b. Ligation of the $F_1$ (B)-DNA with the $F_2$-DNA and Construction of a Recombinant Plasmid The ligation is carried out as described in Example 15c, starting from 10 μg of $F_1$ (B)-DNA/EcoRI/HpaII (see above) and 9 μg of $F_2$-DNA/BamHI/HpaII (Example 15bII). The $F_1$ (B)-$F_2$-DNA/EcoRIIBamHI formed is ligated with 30 μg of the vector-DNA pBR322/EcoRI/BamHI (cf. Example 15a) as described.

The resulting solution containing recombinant plasmids is used for transformation of calcium-treated *E. coli* HB101 cells. 15 transformed clones are tested for their $F_1$ (B)-$F_2$-DNA content, as described in Example 11e). A mixture of the oligonucleotides described in examples 5 and 6 is again used as the radioactive probe. 6 positive colonies are obtained in the autoradiogram, one of which has the designation pML160.

Example 17

Characterisation of the Clones pML141 and pML160

In each case 10 μg of the plasmid-DNAs of pML141 and pML160 are digested with in each case EcoRI or BamHI restriction endonuclease (cf. Example 11a or 13a). The characterisation of the pML141 and pML160 is carried out as already described in Example 14.

The nucleotide sequences determined for the $F_1$ (C)-$F_2$-DNA and $F_1$ (B)-$F_2$-DNA are identical to those of the synthetic eglin C and eglin B genes shown above.

Example 18

Figure 5:
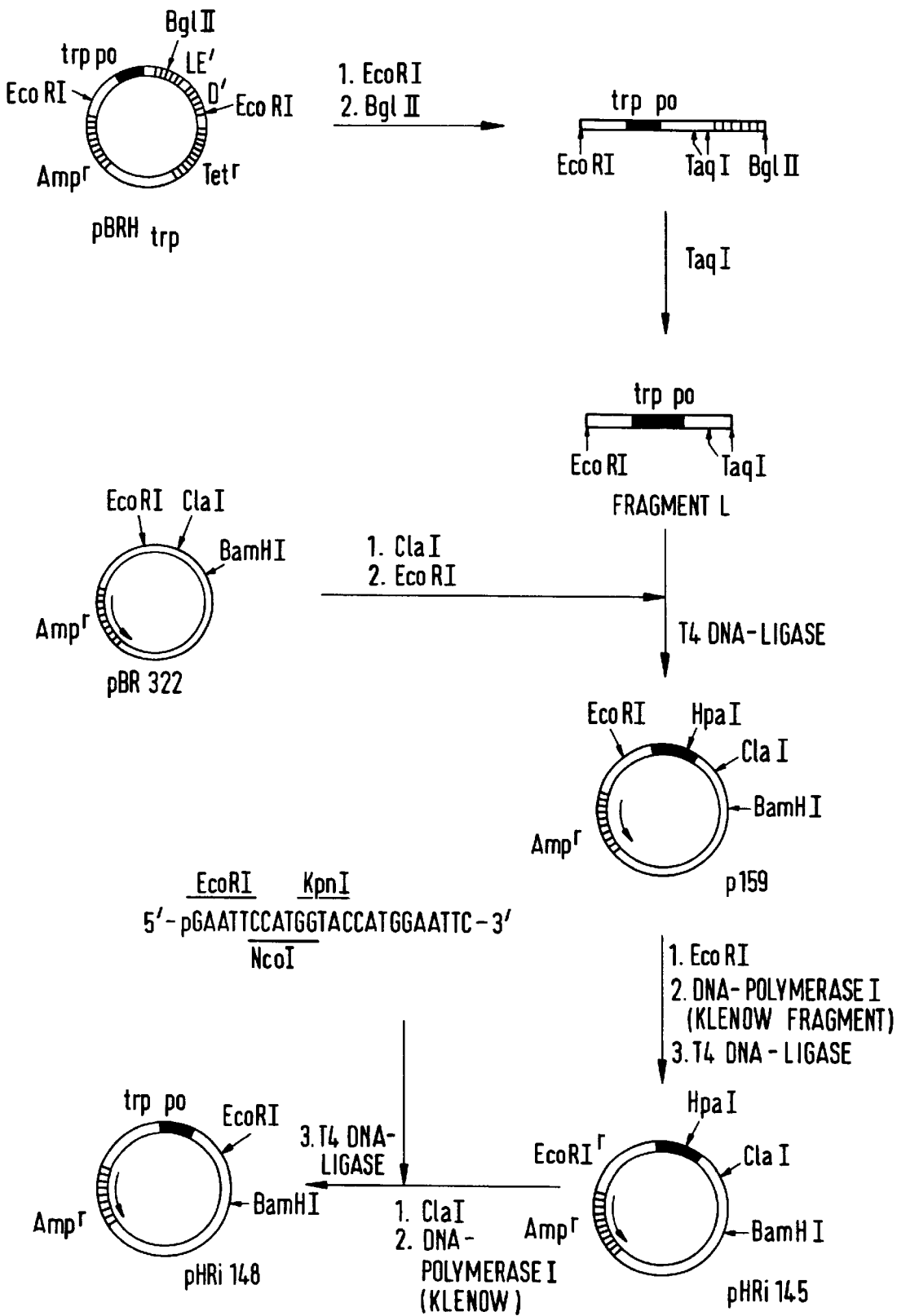
FIG. 5 represents, schematically, the preparation of the vector pHRi148, which contains the trp promoter.
Figure 6:
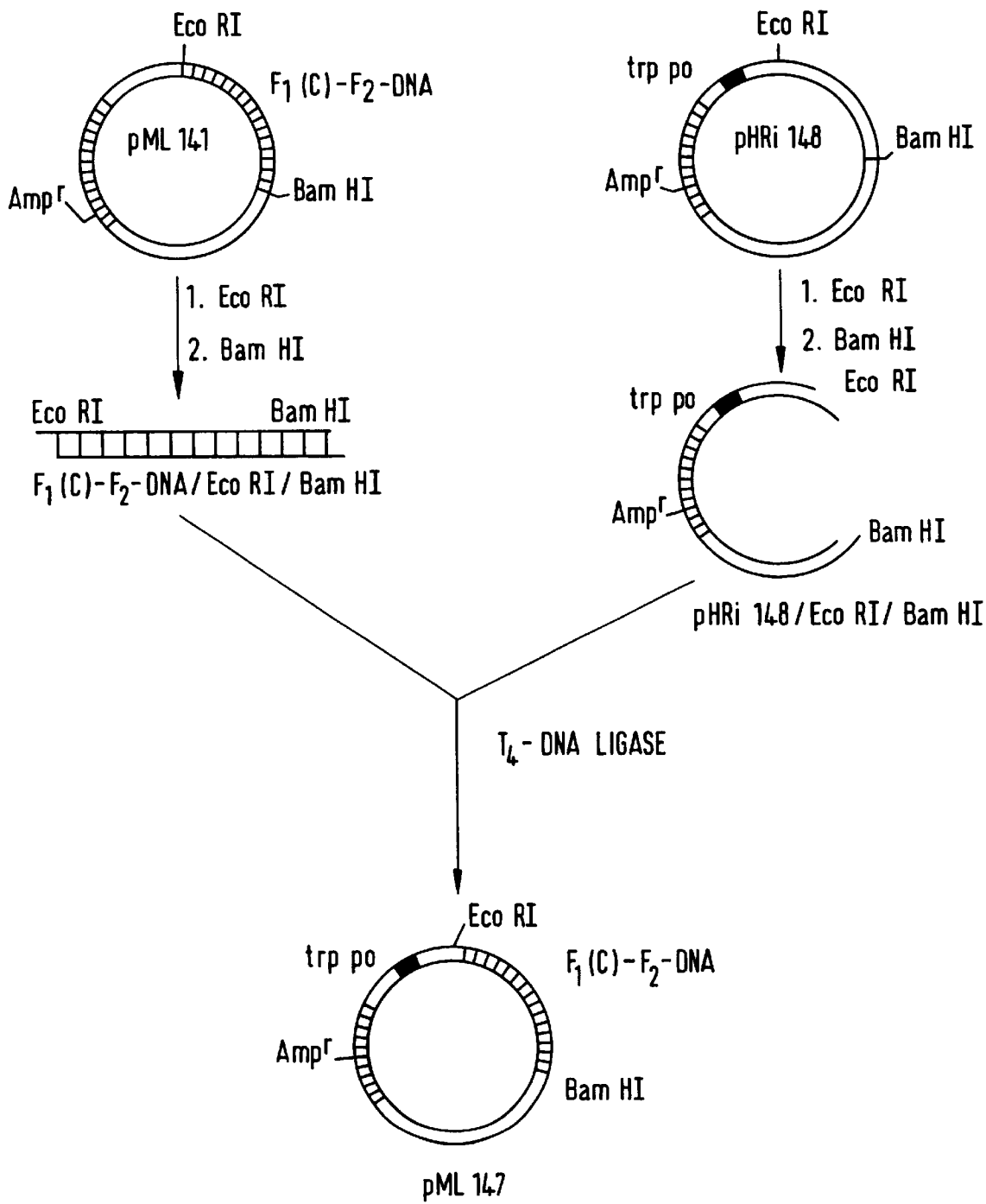
FIG. 6 shows, schematically, the preparation of the expression plasmid pML147, which contains the eglin C gene [$F_1(C)$-$F_2$-DNA], under the control of the trp promoter.

Preparation of the Expression Plasmid pML147 a) Construction of the Linearised Vector pHRi148/EcoRII/BamHI, Containing the trp Promoter Operator (FIG. 5 and FIG. 6)

A. Construction of the Plasmid p159

10 μg of plasmid pBRH$_{trp}$ (21) are cleaved with 50 units of EcoRI (Biolabs) at 37° C. for 60 minutes and the digestion mixture is fractionated, after phenol extraction, by a sucrose density gradient (5–23%) in 50 mM tris.HCl (pH 8.0) and 1 mM EDTA in a TST41(Kontron AG) rotor. The centrifugation lasts 14 hours at 40,000 rpm and 15° C. 0.3 ml fractions are collected with an ISCO gradient collector at 1 ml/minute. The fractions containing the smaller fragment are combined and the solution is brought to TNE and precipitated with 2 volumes of ethanol at −20° C. After centrifugation in an Eppendorf centrifuge, the DNA is dissolved in 100 μl of 10 mM tris.HCt, pH 7.5, and 0.5 mM EDTA. 5 μg of this DNA fragment are cleaved with 5 units of BglII (Biolabs) at 37° C. for 60 minutes. The reaction mixture is extracted with phenol and chloroform and the DNA is incubated with 2 volumes of ethanol at −80° C. for 10 minutes, collected by centrifugation and dissolved again in 50 μl of 50 mM tris.HCl (pH 8.0). 2 μl of this solution are removed (0.2 μg of DNA) and incubated at a DNA concentration of 10 ng/μl in 50 mM tris.HCl (pH 8.0) with 1 unit of intestinal alkaline calf phosphatase (Boehringer) at 37° C. for 30 minutes. The enzyme is inactivated by heating the solution at 65° C. for 60 minutes. 0.04 μg DNA of removed and incubated $_5$'-terminally with 10 μCi [α-$^{32}$P]-ATP (>5,000 Ci/mmol, Amersham) and 5 units of $T_4$ polynucleotide kinase (P-L Biochemicals) in 20 μl of reaction volume in 50 mM tris.HCl (pH 9.5), 10 mM MgCl$_2$ and 5 mM DTT at 37° C. for 30 minutes. The radioactive probe is mixed with the non-labeled probe (see above) and the DNA fragments are fractionated by a 5–23% sucrose density gradient in 50 mM tris.HCl (pH 8.0) and 1 mM EDTA in a TST60 rotor. Centrifugation is carried out at 60,000 rpm and 15° C. for 5 hours. 0.2 ml fractions are collected. The radioactivity of each fraction is determined by measuring the Cerenkov radiation and the fragments are thus identified. The desired fractions containing the small DNA fragment are combined, and the DNA is precipitated with 2 volumes of ethanol and, after centrifugation, dissolved again in 20 μl of 10 mM tris.HCl, pH 7.5, and 0.5 mM EDTA.

The $^{32}$P-tabelted EcoRI-BglII DNA fragment is partially cleaved with 0.2 unit of TaqI (Biolabs) in a volume of 50 µl at 37° C. for 10 minutes. The reaction mixture is brought to 0.2% SDS, 10% glycerol, 10 mM EDTA and 0.05% bromophenol blue and the DNA fragments are separated on a 6% polyacrylamide gel in tris-borate-EDTA (22). The band containing the desired EcoRI-TaqI (the targest part fragment) is identified on the autoradiogram. This fragment (L, cf. FIG. 5) is extracted from the gel and purified (23), and dissolved in 10 µl of 10 mM tris.HCl, pH 7.5, and 1 mM EDTA.

pBR322 cleaved with ClaI and EcoRI is used as the acceptor plasmid: 2 µg of pBR322 are digested with 4 units of ClaI (Biolabs) in a reaction volume of 20 µl at 37° C. for 60 minutes. The protein is extracted with phenol and the DNA is then precipitated with 2 volumes of ethanol at −80° C. for 10 minutes. The DNA is collected by centrifugation and then digested with 10 units of EcoRI (Biotabs) in a reaction volume of 20 µl at 37° C. for 30 minutes. 2 volumes of 0.1 M tris.HCl (pH 8.7) are subsequently added to the solution and the mixture is incubated with 1 unit of alkaline calf phosphatase (Boehringer) at 37° C. for 30 minutes. The phosphatase is then inactivated by incubation at 65° C. for 60 minutes.

100 ng of the acceptor plasmid are incubated with 5 µl of fragment L-DNA in a reaction volume of 15 µl in 10 mM $MgCl_2$, 20 mM tris.HCl (pH 7.8), 10 mM DTT and 0.5 mM ATP with 30 units per µl of reaction volume of $T_4$-DNA-ligase (Biolabs) for 2 hours.

5 µl of this solution are added to a mixture containing 150 ml of *E. coli* HB101 cells treated with calcium chloride (6) in 10 mM $MgCl_2$, 10 mM $CaCl_2$ and 10 mM tris. HCl (pH 7.5) in a total volume of 200 µl. The mixture is cooled in ice for 20 minutes, heated at 42° C. for 1 minute and incubated at 20° C. for 10 minutes. 1 ml of tryptone medium [tryptone medium contains 10 g of Bacto-tryptone (Difco); 1 g of yeast extract (Difco); 1 g of glucose; 8 g of NaCl and 294 mg of $CaCl_2.2H_2O$ in 1 l of distilled water] is added and the mixture is incubated at 37° C. for 30 minutes, while shaking at 300 revolutions/minute. The mixture is plated on two agar plates (McConkey agar, Difco; 0.6 ml/plate), supplemented with 50 µg/ml of ampicillin (Sigma). The plates are incubated at 37° C. for 12 to 17 hours.

The plasmid-DNA from 10 different colonies is isolated as follows:

The colonies are used for inoculation of 10 ml of tryptone medium, supplemented with 50 µg/ml of ampicillin, as above, in a 25 ml conical flask. The cultures are shaken at 37° C. and 300 revolutions/minute for 15 to 18 hours. The cells are harvested by centrifugation (Sorval, HS-4 rotor, 10 minutes at 4,000 revolutions/minute, 4° C.). About 0.1 g of cells is obtained, and these are resuspended in 1 ml of 50 mM tris.HCl (pH 8.0). 0.25 ml of lysosyme solution [10 mg/ml in 50 mM tris.HCl (pH 8.0); lysosyme is marketed by Sigma] is added and, after incubation at 0° C. for 10 minutes, 0.15 ml of 0.5 mM EDTA (pH 7.5) is added. After a further 10 minutes at 0° C., 60 µl of 2% Triton X-100 (Merck) are added. After 30 minutes at 0° C., the probe is centrifuged for 30 minutes at 15,000 revolutions/minute and 4° C. in a Sorval SA-600 rotor. The supernatant liquor is deproteinated with 1 volume of phenol (saturated with TNE). The phases are separated by centrifugation (Sorval HB-4 rotor) for 10 minutes at 5,000 revolutions/minute and 4° C. The upper phase is extracted twice with 1 volume of chloroform. Pancreatic RNAase A (Sigma; 10 mg/ml in TNE, preheated at 85° C. for 10 minutes) is added up to a final concentration of 25 µg/ml and the mixture is incubated at 37° C. for 40 minutes. The solution is then brought to 1M NaCl and 10% polyethylene glycol 6000 (Fluka, treated for 20 minutes at 120° C. in an autoclave) and is incubated at −10° C. for 2 hours. The precipitate is collected in a Sorval HB-4 rotor (20 minutes at 10,000 revolutions/minute, 0° C.) and dissolved again in 100 µl of TNE. The DNA solution is extracted with 1 volume of phenol and the DNA is precipitated with 2 volumes of ethanol at −80° C. for 10 minutes. The precipitate is collected by centrifugation in an Eppendorf centrifuge and the DNA is again dissolved in 20 µl of 10 mM tris.HCl (pH 7.5) and 0.5 mM EDTA. 8 to 10 µg of plasmid-DNA are obtained from a 10 ml culture.

After digestion with the following restriction enzymes, the plasmid-DNAs are analysed:

In each case 0.5 µg of plasmid-DNA is cleaved with HpaI (Biolabs) and with HpaI (Biolabs) and EcoRI (Biolabs) with ClaI (Biolabs) following standard instructions, in accordance with the statements of the enzyme manufacturer. The DNAs are fractionated on a 1% agarose gel in 40 mM tris. acetate (pH 7.8), 1 mM EDTA and 0.5 µg/ml of ethidium bromide. The desired plasmids contain an HpaI site and, after 3-fold digestion, besides the large DNA fragment, give 2 smaller fragments which are larger than the small EcoRI-ClaI fragment of pBR322. One of these plasmids is designated p159(cf. FIG. 5).

B. Construction of the Plasmid pHRi145

2 µg of p159-DNA are digested with 10 units of EcoRI (Biolabs) at 3° C. for 30 minutes. The DNA is extracted with phenol, precipitated with ethanol and, after centrifugation, dissolved in 10 µl of 10 mM tris.HCl (pH 7.5) and 0.5 mM EDTA. The DNA digested with EcoRI is furthermore treated with 5 units of DNA-polymerase (Klenow fragment) (Boehringer) in 10 mM $MgCl_2$, 10 mMp -mercaptoethanol, 50 mM NaCl, 0.1 mM dATp (P&L Biochemicals) and 0.1 mM dTTp (P&L Biochemicals) at 12° C. for 15 minutes. The polymerase is then inactivated by incubation at 85° C. for 5 minutes. The reaction mixture is diluted 10-fold in 20 mM tris.HCl (pH 7.8), 10 mM $MgCl_2$, 10 mM DTT and 0.5 mM ATP (Sigma) and incubated with 30 units of $T_4$-DNA-ligase per µl of reaction mixture at 15° C. for 1 hour.

50 ng of the DNA are transformed in *E. coli* (as described above) and plated out onto McConkey agar plates supplemented with 50 µg/ml of ampicillin.

The plasmid-DNAs of 10 different colonies are isolated as described above. The plasmid-DNAs are analysed by digestion with EcoRI. The desired plasmids are EcoRI-resistant. The analysis is carried out as described above. One of the desired plasmids is designated HRi145 (FIG. 5).

C. Construction of the Plasmid pHRi148

2 µg of pHRi145-DNA are treated with 5 units of ClaI (Boehringer) at 37° C. for 60 minutes and are then deproteinated by means of phenol extraction. The DNA is precipitated with ethanol and then dissolved in 20 µl of 10 mM tris.HCl (pH 7.5) and 0.5 mM EDTA. The staggered ends are made up with DNA-polymerase I (Klenow fragment), as described above, with the modification that the dATp and dTTp are replaced by dCTp (P&L Biochemicals) and dGTp (P&L Biochemicals). The polymerase is inactivated by incubation at 85° C. for 5 minutes. 2 volumes of 0.1 M tris.HCl (pH 8.7) are added to the reaction mixture and the mixture is incubated with 0.5 unit of calf phosphatase (Boehringer) at 37° C. for 30 minutes. The reaction mixture is deproteinated by phenol extraction. The DNA is precipitated with ethanol and dissolved in 8 µl of 10 mM tris.HCl (pH 7.5) and 0.5 mM EDTA.

A chemically synthesised DNA-linker of the formula

5'-GAATTCCATGGTACCATGGAAMTTC-3' is phosphorylated on the 5'-end by incubating 8 pmol of the linker with 5 µCi of [γ-$^{32}$P]-ATP (5,500 Ci.mmol$^{-1}$, Amersham) in a reaction volume of 8 µl, containing 0.1 mM rATp (Sigma), 50 mM tris.HCl (pH 9.5), 10 mM MgCl$_2$, 5 mM DTT and 2 units of T$_4$-polynucleotide kinase (P&L Biochemicals), at 37° C. for 30 minutes. The reaction is stopped by freezing at −80° C.

The radioactively labelled linker is then treated with 1 µg of ClaI and phosphatase and ligated with pHRi145-DNA (see above) in a reaction volume of 20 µl, containing 0.5 mM rATp (Sigma), 10 mM DTT (Calbiochem), 20 mM tris.HCl (pH 7.8), 1 mM MgCl$_2$ and 800 units of T$_4$-DNA-ligase (Biolabs). Incubation is carried out at 15° C. for 2 hours. The ligase is inactivated by incubation at 85° C. for 10 minutes. 2 volumes of water are then added, the sodium chloride concentration is brought to 10 mM and 20 units of KpnI (Biolabs) are added at 37° C. in the course of 30 minutes. After extraction with phenol and chloroform, the mixture is fraction-fractionated by a 0.9% low-melting agarose get (Biorad) in 40 mM tris.acetate (pH 7.8), 1 mM EDTA and 0.5 µg/ml of ethidium bromide. The band, visible by UV radiation, which shows the same mobility as a marker-DNA of the same size, is excised with a scalpel. The piece of get is melted at 65° C. for 5 minutes and then cooled to 37° C. A volume of about 20 µl is obtained. 5 µl of this solution are removed and incubated with 400 units of T$_4$-ligase (Biolabs) in a reaction volume of 10 µl, which is brought to 0.5 mM ATP, 10 mM DTT, 10 mM MgCl$_2$ and 20 mM tris.HCl (pH 7.8), at 15° C. for 12 hours. ¹⁄₁₀ of the volume of a solution with 100 mM tris.HCl (pH 7.5), 100 mM CaCl$_2$ and 100 mM MgCl$_2$ is added to the ligase mixture (solidified at 15° C.) and incubated at 65° C. for 5 minutes. The solution is then used to transform calcium-treated *E. coli* HB101 cells, as described above. It is plated out onto McConkey agar plates, supplemented with 50 ug/ml of ampicillin.

The plasmid DNAs of 10 different colonies are isolated, as described above, and the DNA is subjected to the following restriction enzyme analysis: In each case 0.5 µg of plasmid DNA is cleaved in succession with KpnI (Biolabs), NcoI (Biolabs) and EcoRI (Biolabs) in accordance with the instructions of the enzyme manufacturer. The cleavage products are fractionated on 1% agarose gels in 40 mM tris. acetate (pH 7.8), 1 mM EDTA and 0.5 µg/ml of ethidium bromide. All the plasmids each show one of these enzyme cleavage sites, as desired. One is designated HRi148.

The plasmid HRi148 contains a tryptophan promoter operator and a ribosomal bonding site up to and with ATG. Eglin C and also other heterologous genes can be coupled directly via the EcoRI, NcoI and KpnI sites occurring singly in the plasmid. Furthermore, this construction permits direct coupling and expression of heterotogous genes, without the ATG necessary for initiation of the translation having to be present on the corresponding gene. This can easily be achieved by cleavage with NcoI and making up of the staggered ends with DNA-polymerase I, as described, or by cleavage with KpnI and removal of the staggered ends by nuclease Si. The plasmid HRi148 is thus a widely applicable expression plasmid.

D. Preparation of the Linearised Vector pHRi148/EcoRI/BamHI

5 µl of plasmid-DNA of pHRi148 are digested with the restriction endonucleases EcoRI and BamHI, as described in Example 15a. The vector pHRi148/EcoRI/BamHI excised is isolated by means of density gradient centrifugation (cf. Example 15a).

b) Preparation of the F$_1$ (C)-F$_2$-DNA/EcoRI/BamHI (FIG. 6)

5 µg of plasmid-DNA of pML141 are digested with EcoRI and BamHI restriction endonuclease as described in Examples 11a) and 13a). After phenol/chloroform extraction and precipitation with alcohol, the F$_1$ (C)-F$_2$-DNA/EcoRI/SamHI of the plasmid (pBR322/EcoRI/BamHI) is separated off by get electrophoresis on 1% low-melting agarose (Biorad) (Example 13a) and rendered visible with EtBr. The site of the gel containing the DNA band of the F$_1$ (C)-F$_2$-DNA (=236 base pairs) is then cut out of the gel and liquefied at 65° C. for 10 minutes.

c) Ligation of the pHRi148/EcoRI/BamHI Vector-DNA with the F1 (C)-F$_2$-DNA/EcoRI/BamHI and Construction of the Plasmid pML147 (FIG. 6)

100 ng (about 100 nmol of ends) of the plasmid-DNA of pHRi148/EcoRI/BamHI and 28 ng (713 nmol of ends) of the F$_1$ (C)-F$_2$-DNA/EcoRI/BamHI (dissolved in 10 µl of the liquid get obtained in Example 18b)) are mixed with one another in a volume of 20 µl at 37° C. and are treated with T$_4$-DNA-ligase at 15° C. for 16 hours, as described in Example 13c). The expression plasmid pML147 containing the eglin C gene (F$_1$ (C)-F$_2$-DNA) is formed in this mixture in this manner.

d) Transformation of *E. coli* HB101 with the Plasmid pML147

10 µl of the mixture containing the plasmid pML147 (Example 18c) are liquefied at 65° C. for 10 minutes and used for the transformation of calcium-treated *E. coli* HB101 cells. About 6,000 ampicillin-resistant colonies are obtained.

e) Screening of the Colonies Containing F$_1$ (C)-F$_2$-DNA

Transformed colonies (Example 18d) are tested for the presence of F$_1$ (C)-F$_2$-DNA, as described in Example 15e).

Seven positive colonies, which have the designation pML147–pML153, are obtained.

The F$_1$ (C')-F$_2$-DNA/EcoRI/BamHI or F$_1$ (C")-F$_2$-DNA/EcoRI/BamHI prepared from the plasmids pML147 (C') or pML147 (C") are ligated with the pHRi148/EcoRI/amHI in an analogous manner. Plasmids which contain the eglin C' gene [F$_1$ (C')-F$_2$-DNA] or the eglin C" gene [F$_1$ (C")-F$_2$-DNA] are formed in this manner. The plasmids are used for the transformation of calcium-treated *E. coli* HB101 cells. Culture of the transformed cells gives 940 or, respectively, 1,080 ampicillin-resistant colonies. The colonies are tested with the oligonucleotide 91/37 complementary (C) for the presence of F$_1$ (C')-F2-D4A or F$_1$ (C")-F$_2$-DNA. 9 colonies containing the F$_1$ (C')-F2-DNA (eglin C' gene) and 17 colonies containing the F$_1$ (C")-F$_2$-DNA (eglin C" gene) are identified. In each case one colony is selected and has the designation pML147 (C') or pML147 (C").

Example 19

Preparation of the Expression Plasmid pML 199 a. Preparation of the F$_1$ (B)-F$_2$-DNA/EcoRI/BamHI

Analogously to Example 13b), 5 µg of plasmid-DNA of pML160 are digested with the restriction endonucleases EcoRI and BamHI. The F$_1$ (B)-F$_2$-DNA/EcoRI/BamHI is separated off by means of get electrophoresis, as described.

b. Ligation of the pHRi148/EcoRI/BamHI Vector-DNA with the F$_1$ (B)-F$_2$-DNA/EcoRI/BamHI and Construction of Recombinant Plasmids 100 µg of plasmid-DNA of pHRi148/EcoRI/BamHI (cf. Example 18aD) are ligated with 28 µg of F$_1$ (B)-F$_2$-DNA/EcoRI/BamHI according to Example 18c). The resulting solution, which contains recombinant plasmids, is used to transform calcium-treated *E. coli* HB101 cells. Transformed colonies are tested for the presence of $F_1$ (B)-$F_2$-DNA, as described in Example 15e).

Six positive colonies are obtained, which have the designation pML199–204.

Example 20

Characterisation of the Clones pML147 and pML199

The $F_1$ (C)-$F_2$-DNA or $F_1$ (B)-$F_2$-DNA sequences in recombinant plasmids pML147 and pML199 are characterised by sequencing the $F_1$ (C)-$F_2$- or $F_1$ (B)-$F_2$-DNA by the method of Maxam and Gilbert (3), as described om Example 17. 10 μg of plasmid-DNA are tested. The nucleotide sequence of the $F_1$ (C)-$F_2$-DNA is identical to that described for the synthetic eglin C gene, and that of the $F_1$ (B)-$F_2$-DNA is identical to that described for the synthetic eglin B gene.

Example 21

Synthesis of Polypeptides with Eglin Activity By *E. coli* Cells Containging Plasmids with Recombinant Eglin Genes a. Synthesis of Polypeptides with Eglin C Activity Each of the 7 clones containing the recombinanat eglin C gene, that is to say *E. coli* HB101 pML 147, *E. coli* HB101 pML 148, *E. coli* HB101 pML 149, *E. coli* HB101 pML 150, *E. coli* HB101 pML 151, *E. coli* HB101 pML 152, *E. coli* HB101 pML 153, *E. coli* HB101 pML 147 (C') and *E. coli* HB101 pML 147 (C"), is tested for the formation of eglin C activity.

For this purpose, the abovementioned clones are cultures in 5 ml of L medium overnight (16 hours) at 37° C. and 250 rpm. L medium has the following composition: 10 g of Bacto tryptone, 5 g of Bacto yeast extract, 5 g of Nacl, 5 g of glucose and 0.1 g of ampicillin.

1 ml g of this overnight culture is transferred to 25 ml of M9 medium on the following day. M9 medium has the following composition: 13.25 g of $Na_2HPO_4.7H_2O$, 3.0 g of $KH_2PO_4$, 0.5 g of NaCl, 1.0 g of $NH_4Cl$, 0.015 g of $CaCl_2.2H_2O$, 0.25 g of $MgSO_4.7H_2O$, 2.5 g of casaminoacids, 0.0099 g of vitamin $B_1$, 5.0 g of glucose and 0.1 g of ampicillin.

Culture is carried out at 37° C. and 250 rpm until the bacteria suspension has reached an optical density ($OD_{623}$) of about 0.9–1.0. The cells (5 ml of the growing culture) are then harvested and the bacteria are resuspended in 0.5 ml of a solution of 50 mM tris.HCl (pH 8) and 30 mM NaCl. The suspension is then brought to 1 mg/ml of lysosyme (Boehringer) and is placed in ice for 30 minutes. By alternating freezing of the suspension in liquid nitrogen and thawing at 37° C., the bacteria are destroyed. This operation is repeated 5 times and the mixture is then centrifuged at 16,000 rpm at 4° C. for 30 minutes. The supernatant liquors are investigated for eglin C activity by measuring the inhibition of human Leucocyte elastase (1).

The following activities are obtained:

| Bacteria extract | Eglin C activity μg/ml of culture |
|---|---|
| *E. coli* HB101 pML 147 | 3.3 |
| *E. coli* HB101 pML 148 | 3.3 |

-continued

| Bacteria extract | Eglin C activity μg/ml of culture |
|---|---|
| *E. coli* HB101 pML 149 | 3.4 |
| *E. coli* HB101 pML 150 | 3.3 |
| *E. coli* HB101 pML 151 | 3.3 |
| *E. coli* HB101 pML 152 | 3.5 |
| *E. coli* HB101 pML 153 | 3.3 |
| *E. coli* HB101 pML 147 (C') | 3.0 |
| *E. coli* HB101 pML 147 (C") | 3.1 | b. Synthesis of Polypeptides with Eglin B Activity

Each of the 6 clones containing the recombinant eglin B gene, that is to say *E. coli* HB101 pML 199, *E. coli* HB101 pML 200, *E. coli* HB101 pML 201, *E. coli* HB101 pML 202, *E. coli* HB101 pML 203 and *E. coli* HB101 pML 204, are tested for the formation of eglin B activity in an analogous manner to that described in Example 21a).

As described, the clones mentioned are cultured in L medium and then transferred to M9 medium. When an optical density ($OD_{623}$) of about 0.9–1.0 has been reached, the cells are harvested, lysed and destroyed by alternating freezing and thawing. The mixtures are centrifuged and the supernatant liquors are tested for eglin B activity by measurement of the inhibition of human leucocyte elastase (1).

The following activities are obtained:

| Bacteria extract | Eglin B activity μg/ml of culture |
|---|---|
| *E. coli* HB101 pML 199 | 3.2 |
| *E. coli* HB101 pML 200 | 3.1 |
| *E. coli* HB101 pML 201 | 3.8 |
| *E. coli* HB101 pML 202 | 3.5 |
| *E. coli* HB101 pML 203 | 3.3 |
| *E. coli* HB101 pML 204 | 3.3 |

Example 22

Culture of the Strain *E. coli* H101 pML147

20 ml of L medium (cf. ExampLe 21) are inoculated with the *E. coli* HB101 pML147 cells of a well-grown agar plate and are shaken in shaking flasks on a rotary shaker at 150 rpm at 37° C. for 12 hours. 5 ml of this preculture are transferred to 120 ml of M9 nutrient medium. This culture is shaken at 250 rpm and 37° C. After about 8–10 hours, the culture has reached the maximum titre of polypeptides with eglin C activity and is harvested.

Example 23

Detection of the Eglin C Activity

About 5–10 μl of a sample containing polypeptides with eglin C activity (cf. Examples 21 and 22) are dropped onto 1 $cm^2$ of nitrocellulose paper (NZ) (BIORAD) and the paper is dried at room temperature for 30 minutes. The NZ is then incubated for 1 hour at 37° C. in a solution of 3% of serum albumin in 0.01 M tris.HCL (pH 8) and 0.9% NaCl.

The NZ is then washed in a solution of 0.01 M tris. HCl (pH 8) and 0.9% NaCl for 30 minutes. The solution is thereby changed 5 times. The washed NZ is then treated for 2 hours at 25° C. in a solution of 3% serum albumin in 0.01 M tris.HCl (pH 8) and 0.9% NaCl, containing 2 μg/ml of antibodies (prepared from rabbits, or monoclonal antibodies) against eglin C. The NZ is then washed, as described above.

The NZ is subsequently treated for 2–3 hours at 25° C. with a solution of 3% serum albumin in 0.01 M tris.HCl (pH 8) and 0.9% NaCl containing 0.2 μCi/mL of $^{125I}$-protein A (specific activity 89.8 μCi/mg) (NEN). The NZ is then again washed, as described above, and dried, and the radioactivity bonded is determined in a γ-counter (Multi Gamma 1260 gamma counter, LKB, Wallace), this being a measure of the polypeptide with eglin C activity present on the NZ.

In an alternative process, the above probe is subjected to SDS/polyacrylamide gel electrophoresis (PAGE) [cf. (7)]. The PAGE electropherogram is transferred to the NZ by electro-blotting. The NZ is then treated as described above and/or autoradiographed overnight together with an X-ray film (Fuji). Sites on the NZ which contain polypeptides with eglin C activity appear as black spots on the film.

Example 24

Isolation and Purification of Nα-acetyl-eglin C with the Aid of a Monoclonal Antibody Column a. Preparation of the Polypeptide Solution for the Monoclonal Antibody Column 150 ml of culture broth (obtained according to Example 22) are cooled to 4° C. and the cells are separated off by centrifugation (5,000 rpm, 15 minutes, Sorvall RC 3B). The clear supernatant liquor contains no eglin C activity.

The cells are then suspended in 12 ml of lysis buffer (50 mM tris.HCl, pH 8, and 30 mM NaCl). 15 mg of lysosyme (Boehringer) are added to this mixture, and the mixture is then kept at 4° C. for 30 minutes. The cells are subsequently destroyed by freezing in liquid nitrogen, with subsequent thawing at 37° C., 4 times.

The mixture is then centrifuged at 16,000 rpm and 4° C. for 30 minutes. The supernatant liquor contains the Nα-acetyl-eglin C activity. 7.7 g of solid ammonium sulfate are then dissolved in the supernatant liquor (15 ml). The turbid mixture is left to stand at 4° C. for 30 minutes and is then centrifuged (see above). The wet sediment is dissolved in 1 ml of 0.05 mM tris.HCl buffer, pH 8, to give the desired polypeptide solution.

b. Purification of Nα-acetyl-eglin C on a Monoclonal Antibody Column

The monoclonal antibody column 1K-F299-22-10 (bed volume 0.8 ml, see below) is equilibrated with 0.05 M tris.HCl (pH 8). 0.5 ml portions of the polypeptide solution obtained above are discharged onto the column at 4° C. at a flow rate of 7 ml/hour. The column is then washed with 10 ml of 0.05 M tris.HCl, pH 8. The first fractions contain the non-adsorbed polypeptides, which are discarded. The column is then washed with 5 ml of 5 M sodium thiocyanate (Merck) in 0.05 M tris.HCl (pH 8) and the resulting fractions are tested for Nα-acetyl-eglin C activity by the HLE test (1). The fractions containing the polypeptides are determined by measurement of the $OD_{280}$ nm. Fractions 19 and 20 contain the $N^α$-acetyl-eglin C activity; they are kept at −20° C., or in an ice-bath until further processing. The Nα-acetyl-eglin C activity in fraction 19 is 61 ug/ml and in fraction 20 is 49 ug/ml. The fractions are then dialysed or demineralised over Sephadex-G25 (Pharmacia). The SDS-polyacrylamide gel electrophoresis (7) shows a molecular weight of Nα-acetyl-eglin C of about 8,100 Daltons.

Nα-Acetyl-eglin B, eglin C and eglin 8 can be purified in an analogous manner by means of the monoclonal anti-body column 1K-F299-22-10.

c. Preparation of the Monoclonal Antibody Column 1K-F299-22-10

A) Immunisation of Mice

Pure natural eglin C (6 mg) in lyophilised form is dissolved in a little 0.1% acetic acid and is then made up with phosphate-buffered sodium chloride solution and brought to pH 7.2, so that the final concentration is 2 mg/ml. Portions of this antigen solution are mixed with equal amounts of complete Freund's adjuvant, incomplete Freund's adjuvant or phosphate-buffered salt solution and the mixtures are emulsified.

Female Balb/c mice (8–14 weeks old, obtained from animal farm at Sisseln, Switzerland) are immunised by injection of such an emulsion, containing 100 ug of eglin, into the paw of the foot. During the following six weeks, a further 100 μg of eglin, emulsified as before but in incomplete Freund's adjuvant, are injected subcutaneously each week, and finally 200 μg of eglin in phosphate-buffered salt solution are injected intravenously. Four days later, the spleen is removed for fusion.

B) Preparation of the Hybridoma and Antibody Test

The hybridoma cells are prepared by fusing the resulting splenocytes with the myeloma cell line SP 2/0. $10^8$ splenocytes and $10^7$ myeloma cells are used here. The fusion is carried out as described (9, 26).

The anti-eglin C activity in the hybridoma supernatant liquors is determined with the aid of competitive radioimmunoassays [RIA, (10)].

For this purpose, eglin C is labelled with radioactive $^{125}$iodine by the usual chloramine T method (30,000 cpm). By overnight incubation, a polyclonal rabbit anti-eglin C antibody is fixed in the depressions of a polystyrene microtitre plate. About 50–70% of the radioactive eglin C are bonded to these solid phase antibodies. Of 45 hybridoma cultures obtained, 32 supernatant liquors significantly inhibited this bonding to the extent of more than 50%. Two of the greatly inhibiting supernatant liquors, or their hybridoma cells, are designated 299S18 and 299S22 and are selected for further characterisation. They are first cloned by the limiting dilution method, 299S18 giving four positive clones and 299S22 giving nine positive clones, of which clones 299S18-20, 299S22-1 and 299S22-10 are chosen and characterised more closely. The hybridoma cell Lines mentioned produce monoclonal antibodies (with the same designation) of the subtype $Ig_1$cappa.

C) Isotation and Purification of the Anti-eglin C Antibodies from Ascites

Balb/c mice are pretreated intraperitoneally with 0.4 ml of pristane (Carl Roth). After one week, 2 to 5×10$^6$ cloned hybridoma cells are injected intraperitoneally. Ascitic fluid is repeatedly taken from each mouse and frozen at −80° C. The fluid collected is thawed and centrifuged at 4° C. at 16,000 rpm for 30 minutes. The fat is sucked off and 0.9 volume equivalent of a saturated ammonium sulfate solution is slowly added dropwise to the remaining debris-free supernatant liquor at 0° C., with stirring. The resulting crude immunoglobulin fraction is passed through Sephacryl G 200 (Pharmacia), using 0.1 M tris.HCl (pH 8.2), in accordance with the instructions of the manufacturer. Active fractions are combined and concentrated with an Amicon XM50 filter (Amicon). The monoclonal anti-eglin C antibodies 299S18-20, 299S22-1 and 299S22-10 are obtained in this manner.

D) Preparation of the Antibody Column 1K-F299-22-10

Affi gel 10 (Bio-Rad) is washed with cold distilled water and coupling buffer, pH 8.0 (0.1 M $NaHCO_3$ solution), in accordance with the instructions of the manufacturer. A 50% suspension of the gel in coupling buffer (1 ml) is transferred to a plastic tube and mixed with the same amount of purified antibody solution (19 mg of monoclonal anti-eglin C antibody 299S22-10), and the mixture is rotated at room temperature for 4 hours. The gel is then washed with coupling buffer. To block the active sites which are still free, the gel is treated with 0.1 ml of 1 M ethanolamine-HCl (pH 8.0) per ml of gel for 2 hours at room temperature and then washed with phosphate-buffered salt solution containing 10 mM sodium azide per ml of gel, the mixture being kept at 4° C. The degree of coupling is determined by measurement of the extinction at 280 nm and is 15 to 30 mg of antibody per ml of gel. 0.8 ml of the immunogel formed is used to prepare the monoclonal antibody column 1K-F299-22-10.

Example 25

Isolation and Purification of $N^\alpha$acetyl-eglin C with the Aid of an Anhydrochymotrypsin Column a. Preparation of the Polypeptide Solution for the Anhydrochymotrypsin Column 150 ml of culture broth (obtained according to Example 22) are cooled to 4° C. and the cells are separated off by centrifugation (5,000 rpm, 15 minutes, Sorvall RC 3B). The clear supernatant liquor contains no eglin.

The cells are then suspended in 12 ml of lysis buffer (50 mM tris.HCl, pH 8, and 30 mM NaCl). 15 mg of lysosyme (Boehringer) are added to this mixture, and the mixture is then kept at 4° C. for 30 minutes. The cells are then destroyed by freezing in liquid nitrogen, with subsequent thawing at 37° C., 4 times. The mixture is then centrifuged at 16,000 rpm and 4° C. for 30 minutes. The supernatant liquor contains the-$N^\alpha$-acetyl-eglin C activity. 7.7 9 of solid ammonium sulfate are subsequently dissolved in the supernatant liquor (15 ml). The cloudy mixture is left to stand at 4° C. for 30 minutes and then centrifuged (see above). The wet sediment is dissolved in 1 ml of 0.05 mM tris.HCl buffer, pH 8, and the desired polypeptide solution is obtained.

b. Purification of N$\alpha$-acetyl-eglin C on an Anhydrochymotrypsin (AnCht) Column The AnCht column (bed volume 4 ml) is equilibrated with 0.05 M tris HCl, pH 8. 2.5 ml portions of the polypeptide solution obtained above are discharged onto the column with a flow rate of 7 ml/hour at 4° C. The column is then washed with 25 ml of 0.05 M tris.HCl (pH 8). The first fractions contain the non-adsorbed polypeptides, which are discarded. The column is then washed with 10 ml of 5 M sodium thiocyanate (Merck) in 0.05 M tris.HCl (pH 8) and the resulting fractions are tested for N$\alpha$-acetyl-eglin C activity by the HLE test (1). The fractions containing the polypeptides are determined by-measurement of the $OD_{280}$nm. Fractions 30 and 31 contain the $N^\alpha$-acetyl-eglin C activity; they are kept at −20° C., or on an ice-bath until further processing. The $N^\alpha$-acetyl-eglin C activity is 30 ug/ml in fraction 30 and 64 $\mu$g/ml in fraction 31. The fractions are then dialysed or demineralised over Sephadex-G25 (Pharmacia). SDS-polyacrylamide gel electrophoresis (7) gives a molecular weight of $N^\alpha$-acetyl-eglin C of about 8,100 Daltons.

c. Preparation of the Anhydrochymotrypsin Column

A. Preparation of Anhydrochymotrypsin (AnCht)

AnCht is prepared as described by Ako et at. (27):

500 mg of chymotrypsin (Merck) are dissolved in 50 ml of 0.1 M tris-HCl buffer (pH 8), containing 0.1 M NaCl, 0.12 M $CaCl_2$ and 13% (v/v) of methanot. Seven 0.1 ml aliquot portions of phenylmethylsulfonyl fluoride (PMSF) (Fluka, solution of 7 mg/ml in acetone) are added to this solution, with stirring, and the decrease in chymotrypsin activity is in each case determined (28). When the chymotrypsin activity has fallen to below 1%, the solution is dialysed against 1 mM HCl overnight at 4° C. (3×10 litres) and then lyophilised.

The phenylmethylsulfonyl-chymotrypsin (PMS-Cht) formed is dissolved in 100 ml of ice-cold 0.1 M KOH and the solution is left to stand in ice for 1 hour and then brought to pH 3 with 6 N HCl. The resulting solution is dialysed against 1 mM HCl at 4° C. overnight (3×10 litres) and then lyophilised. AnCht is obtained as a white powder (120 mg).

B. Preparation of the AnCht Column

Affi gel 10 (Bio Rad) is washed with cold distilled water and coupling buffer, pH 8.5 (0.1 M $NaHCO_3/Na_2CO_3$ solution) in accoruance with the instructions of the manufacturer. A 50% suspension of the gel in coupling buffer (4 ml) is transferred to a plastic tube and mixed with the same amount of anhydrochymotrypsin solution (120 mg in 4 ml of coupling buffer), and the mixture is rotated at 4° C. overnight. The gel is then washed with coupling buffer. To block the active sites which are still free, the gel is treated with 0.1 ml of 1 M ethanotamine-HCl (pH 8.0) per ml of gel at 4° C. for 3 hours and then with phosphate-buffered salt solution, containing 10 mM of sodium azide per ml of gel, the temperature being kept at 4° C. The degree of coupling is determined by measuring the extinction at 280 nm and is 15 to 30 mg of AnCht per ml of gel.

4 ml of the AnCht gel formed are used to prepare the affinity column.

$N^\alpha$-Acetyl-eglin B, eglin C and eglin B can also be purified in the same manner.

Example 26

Alternative Purification Processes for N$\alpha$-acetyl-eglin C

The following purification steps can be used alternatively or in addition to the above purification processes (cf. Examples 24 and 25):

a. Butanol Extraction of the Lysate

Acetic acid (to a final concentration of 0.1%; pH 4.5) is added to the cells destroyed after lysis by freezing and thawing four times (cf. Example 24a). The bacterial proteins precipitating are separated off by means of centrifugation. N$\alpha$-Acetyl-eglin C remains in the supernatant liquor.

The two-phase mixture of n-butanol/glacial acetic acid/water 5:1:4 (25 ml) is vigorously premixed. It is then allowed to equilibrate at room temperature for 2 hours, whereupon the mixture separates into two phases. 0.5 ml of the 0.1% acetic acid lysate sample (see above) is diluted with 250 $\mu$l of the lower phase and N$\alpha$-acetyl-eglin C is extracted with 750 $\mu$l of the upper phase (5 minutes, Vortex, Bender Hobein). The phases are then separated by centrifugation (5,400 rpm) at room temperature for 60 minutes. (Hettich bench centrifuge EBA 3S). The sample is evaporated to dryness under a high vacuum with a Savant apparatus (Speed Vac Concentrator). Detection of the N$\alpha$-acetyl-eglin C is effected by means of the HLE test, RP-HPLC and SDS-gel electrophoresis.

b. Gel Filtration on Sephadex G50

31 mg of the material thus obtained are suspended in 600 $\mu$l of 30% acetic acid, the suspension is centrifuged at 5,000 rpm at room temperature for 5 minutes and the clear supernatant liquor is discharged onto the Sephadex G50 fine column (Pharmacia) (column dimensions: 1.5 cm×30 cm; detection: LKB8300 Uvicord II; 254 nm, transmission 500 mv; flow: 0.4 ml/minute). The column is eluted with 50 ml of 2% acetic acid. Fractions 6–8 (2.5 ml) contain Nα-acetyl-eglin C. Yield: 3 mg of pure lyophilisate, purity about 95%.

c) Anion Exchange Chromatography on DEAE-cellulose to Obtain Nα-acetyl-eglin C and eglin C 100 ml of a supernatant liquor obtained after protein precipitation by means of acetic acid (cf. Example 26a) are concentrated and subjected to anion exchange chromatography on DEAE-53 (Whatman) at pH 6.6 (chromatography conditions: column: 1.5×80 cm, elution buffer: 30 mM ammonium acetate, pH 6.6, flow. 15 ml/h, fraction volume: 3.5 ml). The column is equilibrated with the elution buffer and developed until the first peak (eglin C) between fractions 18–25 is eluted. From fraction 50, a linear salt gradient of in each case 300 ml of elution buffer and 0.06 M ammonium acetate/0.4 M NaCl, pH 4.5, is excluded. Nα-Acetyl-eglin C is eluted between fractions 70 and 85. Detection is by means of RP-HPLC, PAGE and the HLE test. The purity of the product is about 90% in respect of the protein content.

IP (pool fractions 18–25): 6.5
IP (pool fractions 70–85): 5.4.

Nα-Acetyl-eglin B, eglin 8 and other eglin compounds (methionine-eglin C. inter alia, from the biosynthesis) can also be separated off and purified in this manner described.

Example 27

Proof of Structure and Physico-chemical Characterisation of Nα-acetyl-eglin C a. Determination of the Aminoacid Composition 200 μg of Nα-acetyl-eglin C are hydrolysed with 6N HCl at 110° C. for 24 hours and the mixture is then analysed by the method of S. Moore et at. (29). The hydrolysate has the following composition:

| Amino acid | Hydrolysate | Amino acid | Hydrolysate |
|---|---|---|---|
| Asp | 7.2 (7) | Met | 0 (0) |
| Thr | 4.6 (5) | Leu | 5.3 (5) |
| Ser | 3.5 (3) | Tyr | 4.9 (6) |
| Glu | 7.8 (7) | Phe | 4.9 (5) |
| Pro | 5.4 (6) | Lys | 2.3 (2) |
| Gly | 5.7 (5) | His | 2.5 (3) |
| Ala | 1.6 (1) | Trp | 0 (0) |
| Val | 10.1 (11) | Arg | 4.5 (4) |
| | | Total: | (70) | b. Peptide Mapping of Nα-acetyl-eglin C

The aminoacid sequence of Nα-acetyl-eglin C and the cleavage sites for trypsin and *Staphylococcus aureus* protease (V8) are marked in the following scheme (cf. reference 31):

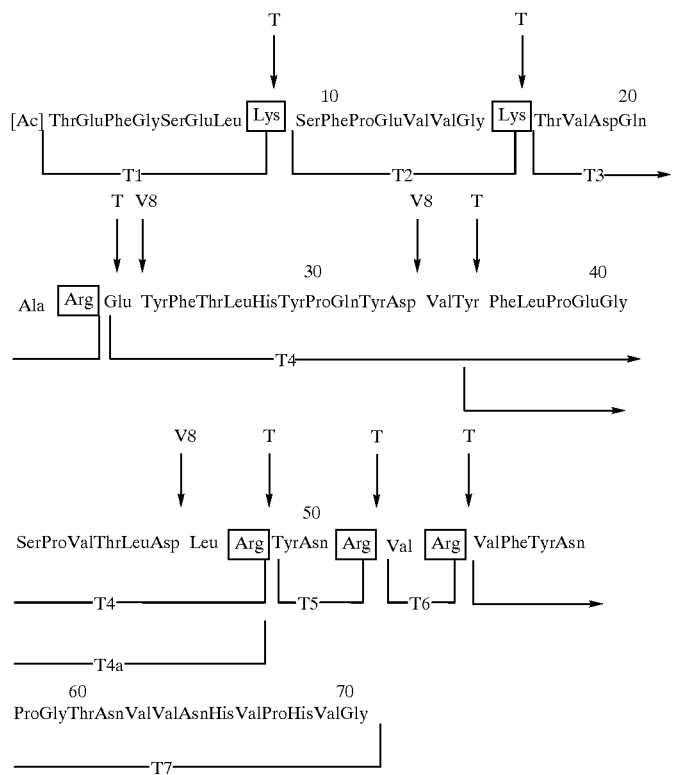

T: Cleavage sites for trypsin; V8: cleavage sites for *Staphylococcus aureus* protease (V8)

I) Tryptic Degradation of Nα-acetyl-eglin C

Nα-Acetyl-eglin C (9.6 mg, 1.18 μmol) is suspended in 2 ml of 0.1 N ammonium acetate buffer and $10^3$ M $CaCl_2$, the pH is brought to 7.5 with dilute ammonia and the mixture is incubated with TPCK trypsin (Worthington, 500 μg) at 37° C. for 90 hours; The enzyme reaction is stopped by addition of 50 μl of glacial acetic acid. A tryptic fragment ($T_4$) is removed by centrifugation and the clear supernatant liquor is then separated into the remaining tryptic fragments ($T_{1-T7}$) by means of reverse phase HPLC (cf. the above scheme). Analysis is by means of FAB mapping (30).

The tryptic degradation of Nα-acetyl-eglin C (200 pmol) and micro-preparative RP-HPLC isolation of DABTC peptides by the method of R. Knecht et at. (32), as well as the comparison with natural eglin C confirms the identity of the tryptic peptides $T_2$, $T_3$, $T_4$, $T_5$, $T_6$ and T7 (cf. the above scheme).

The peptide $T_1$ (threonine on the N-terminus) has a different retention time in HPLC analysis to natural eglin C in both experiments (Nucleosil 5/C18, 4.6×120 mm; 1.2 ml/min; eluting agent: 0.1% trifluoroacetic acid; acetonitrile/water 8:2 with 0.07% trifluoroacetic acid): $R_t$=9.44 minutes (for comparison, peptide $T_1$ in natural eglin C: $R_t$=7.34 minutes).

II. Staphylococcus Aureus Protease V8 Degradation of the Tryptic Fragment $T_4$ of Nα-acetyl-eglin C The degradation of about 100 μg of the tryptic fragment $T_4$ of $N^α$-acetyl-eglin C (see above) by *Staphylococcus aureus* protease V8 is carried out in 100 μl of 0.1 M ammonium acetate, pH 8.0, at 37° C. for 4 hours. The degradation gives the expected fragments (cf. the above scheme; mixture analysis by means of FAB-MS).

c. Partial Sequence Analysis

I) Edman Degradation

The failure of classical sequence analysis by the method of EJ under standard conditions 3) (no N-terminal aminoacid radicals are identified) indicates a modified (blocked) N-terminus in $N^α$-acetyl-eglin C.

II) Sequencing by Means of FAB-MS

The N-terminal tryptic fragment "$T_1$" has, according to FAB ("fast atom bombardment")-MS, a nominal molecular weight of 951. This is thus 42 higher than in the corresponding $T_1$ fragment from natural eglin C (909). On the basis of the differences in weight the modification must be on the N-terminal aminoacid threonine.

The molecular weights of the remaining tryptic fragments from the above experiment (Example 27bI) correspond to expectations.

d) Molecular Weight Determination of Nα-acetyl-eglin C (Comparison with Natural Eglin C)

| Sample 1 ($N^α$-acetyl-eglin C) | Sample 2 (natural eglin C from leeches) |
|---|---|
| Empirical formula: $C_{375}H_{522}N_{96}O_{108}$ chemical molecular weight found: 8,133.1 calculated: 8.133.06 | Empirical formula $C_{373}H_{550}N_{69}O_{107}$ chemical molecular weight found: 8,091.4 calculated: 8,091.03 |

The chemical molecular weights are averaged from 3 different measurements (C, 12.011; H, 1.0079; N, 14.0067; and 0 15.9994).

Experimental conditions: about 30 μg of sample are dissolved directly in thioglycerol as the matrix on the presenter and are measured with a ZAB-HF (resolution of 1,000) mass spectrometer from VG-Anatytical Ltd. Manchester: Xenon bombardment; ion energy 3 keV; scanning linear mode; calibration: CsI/RbI reference mixture e. Isoelectric Focussing

| Isoelectric point | IP | $N^α$-Acetyl-eglin C | 5.4 |
|---|---|---|---|
| | IP | natural eglin C | 6.5 |

Conditions: In each case 20 μg of sample applied in 20 μl of $H_2O$. PAGplate LKB-Ampholine pH 3.5–9.5, 5% of PAG 1 mm. Electrolyte: anode(+) 1M $H_3PO_4$, cathode(−) 1N NaOH, 20 mA, 700V, 2.5 hours. Staining by means of 10% (weight/volume) trichloroacetic acid solution or Coomassie Brilliant Blue R-250 in the usual manner.

f. Cellulose Acetate Electrophoresis (Ascending)

$N^α$-Acetyl-eglin C: 4.7 cm from the start in the direction of the cathode

Eglin C: 5.8 cm from the start in the direction of the cathode

Conditions: In each case 2 μg of sample applied, in 2 μl of $H_2O$, to Cellogel 8×17 cm foil (Chemetron, Milan): Horiphor flat-bed electrophoresis chamber (Innovativ Labor), electrolyte pH 1.9, 250 volts, 1 hour; detection with the usual staining reagents, such as TDM, ninhydrin, Ponceau S solution (Biotec-Fischer).

g. Detection of the N-acetyl Group in $N^α$-acetyl-eglin C

I) 100 μg of $N^α$-acetyl-eglin C are partially hydrolysed in 100 μl of 0.03 N hydrochloric acid for 16 hours at 110° C. and the mixture is dried under a high vacuum. More than 0.5 equivalent of acetic acid is identified by means of gas chromatography (34).

II) The acetyl function is identified unambiguously by means of 360 MHz proton resonance spectroscopy in the tryptic fragment "$T_1$" (cf. Example 27BI): 400 μg of fragment "$T_1$" from $N^α$-acetyl-eglin C are dried under a high vacuum for 2 hours and dissolved in 1 ml of $D_2O$. The 360 MHz $^1$H-NMR spectrum is measured overnight at 297° k with 4,000 SW. Reference $H_2O$ (δ4.95 ppm). δ2.15 ppm singlet (3H) $CH_3$ from the N-acetyl group δ1.2 ppm doublet (3H, J=7 Hz) γ-$CH_3$ from the threonine.

Example 28

Transformation of Various *E. coli* Strains with the Plasmid pML147 and Culture of the Transformed Host Cells The strains *E. coli* LM1035, *E. coli* JA221 and *E. coli* W3110 trpR, trp Δ ED24 (cf. reference 38) are transformed with the plasmid pML147 in a manner analogous to that described in Example 18d. Transformed colonies are tested for the presence of $F_1$(C)-$F_2$-DNA, as described in Example 15e. 3, 5 and, respectively, 3 positive colonies are obtained, which have the following designations: *E. coli* LM1035/pML 147/1, *E. coli* LM1035/pML147/2, *E. coli* LM1035/pML147/3, *E. coli* JA221/pML147/1, *E. coli* JA221/pML147/2, *E. coli* JA221/pML147/3, *E. coli* JA221/pML147/4, *E. coli* JA221/pML147/ 5, *E. coli* W3110trpR, Δ trpED24/pML147/1, *E. coli* W3110trpR, Δ trpED24/pML147/2 and *E. coli* W3110trp, Δ trpED24/pML147/3.

The clones mentioned are cultured in a modified M9 medium which has the following composition: 9.0 g of $Na_2HPO_4.7H_2O$, 3.0 g of $KH_2PO_4$ 0.5 g of NaCl, 3.5 g of $NH_4Cl$, 0.015 g of $CaCl_2.2H_2O$, 0.25 g of $MgSO_4.7H_2O$, 7.0 g of casaminoacids, 5.0 g of yeast extract, 0.0099 g of vitamin $B_1$, 0.006 g of iron-III citrate, 34.0 g of MOPS (3-morpholinopropane-1-sulfonic acid), 20.0 g of glucose and 0.1 g of ampicillin.

Culturing is continued at 37° C. and 180 rpm until the bacteria suspension has reached an optical density ($OD_{623}$) of about 13.0. The cells (5 ml of the growing culture) are then harvested and the bacteria are resuspended in 0.5 ml of a solution of 50 mM tris.HCl (pH 8) and 30 mM NaCl. The suspension is then brought to 1 mg/ml of lysosyme (Boehringer) and placed in ice for 30 minutes. The bacteria are destroyed by alternately freezing the suspension in liquid nitrogen and thawing at 37° C. This operation is repeated 5 times. The mixture is then centrifuged at 16,000 rpm and 4° C. for 30 minutes.

Each of the clones is tested for the formation of eglin C activity, as described in Example 21. Eglin C activities of 3.0–13 μg/ml of culture are obtained in the bacteria extracts. The following activities are obtained, for example:

| Strain | Eglin C activity (μg/ml of culture solution) |
|---|---|
| E. coli LM1035/pML147/1 | 3.0 |
| E. coli JA 221/pML147/1 | 6.0 |
| E. coli W3110trpR,trp Δ ED24/pML147/1 | 11.0 |

Example 29

Fermentation of the Transformed Strain E. coli W3110trpR,trp Δ ED24/pML147/1 and Working Up of the Culture Broth E. coli W3110trpR,trp Δ ED24/pML147/1 cells are cultured in 3,000 l of modified M9 medium in a 5,000 l fermenter in a manner analogous to that described in Example 28, until the suspension has reached an optical density ($OD_{623}$) of about 10–13.

The culture broth (pH 7.4) is cooled to 10° C. and the cells are treated with an Alfa-Laval BRPX-207 de-sludging device. The clear supernatant liquor contains no eglin activity and is discarded. During the desludging, the sludge chamber is continuously partly destudged with lysis buffer A (50 mM tris.HCl and 30 mM NaCl, brought to pH 8.0 with HCl) and, finally, the contents of the centrifuge dish (7 l) are ejected, with complete desludging with lysis buffer A. The resulting cell mass is brought to 375 l with buffer A and has a pH value of 7.6. After cooling to 5–10° C., the suspension is passed through a Dyno mitt (type KD5) equipped with 4.2 l of glass beads 0.5–0.75 mm in diameter. The cells are thereby destroyed. The suspension thus obtained is brought to an acetic acid content of about 2% (v/v) with acetic acid and is stirred at 10° C. overnight. The suspension, with a pH of 3.9, is desludged by the technique described above. The clear supernatant liquor of 300 l is concentrated to 35 l in a falling film evaporator (hourly capacity: 60 l of water). The slightly turbid concentrate is centrifuged and the clear supernatant liquor thus obtained is subjected to diafiltration against 2% acetic acid on a DDS=Lab 35 ultrafiltration unit equipped with GR 81 PP membrane (area 2.5 m²). The final volume is 31 l.

An aliquot test on 2 l of this clear protein solution is applied to a Sephadex G-50 F column (KS 370 Pharmacia) with a bed volume of 96 L, the column being equilibrated with 2% acetic acid. The main fraction contained in 15 l of eluate is concentrated by means of ultrafiltration and then subjected to diafiltration against water. The clear aqueous solution thus obtained is lyophilised. The residue consists of pure eglin C compounds.

Example 30

Analysis of the Product Mixture of the Fermentation of E. coli W3110trpR,trp Δ ED24/pML147/1

The residue obtained in Example 29, consisting of eglin C compounds, is subjected to HPLC analysis.
Experimental conditions: Vydac 218 TP510-RP-HPLC column, 10×250 mm; 1 mg of eglin compounds per separation; AUFC: 2.0 at 220 nm; flow rate: 2 ml/minute; eluant: A: 0.1% trifluoroacetic acid, B: acetonitrile/water 8:2+ 0.07% trifluoroacetic acid, 1 minute 40% B, then increase to 60% B for 30 minutes.

Result: Seven products are identified, which are fractionated and subjected individuaLly to the HLE test. The isoelectric points (IP; isoelectric focussing as described in Example 27e, LKS-Ampholine pH 4.0–6.5) are also determined. The results are summarised in the following table:

| Fraction | Retention time (minutes) | IP | HLE |
|---|---|---|---|
| F0 | 28.2 | 6.5 | + |
| F1 | 29.1 | 6.4 / 6.3 | + |
| F1A | 30.0 | 5.3 | |
| F2 | 31.2 | 5.4 | + |
| F3 | 33.8 | 4.8 | + |
| F4 | 34.6 | 4.8 | + |
| F4A | 35.4 | | |

On the basis of the isoelectric point measured, the HPLC value and the molecular weight determination carried out as a check (molecuLar weight found: 8,133.2), the main product (fraction F2) is Nα-acetyl-eglin C. The substance in fraction 0 (F0) is natural eglin C, as proved by the isoelectric point, the HPLC value and the molecular weight determination carried out as a check (molecular weight found: 8,091.2).

Example 31

Isolation, Structure and Characterization of Several Eglin Compounds from the Fermentation of E. coli W3110 trp Δ ED 24/pML 147/1

The transformed E. coli strain is grown, harvested, the cells disrupted and the expression products processed as described in examples 28/29. The recovered products are further purified by passing them through a reversed phase column (Vydac 300 Å, 30 μm) on a HPLC apparatus (Waters Prep LC 500). The main fraction containing Nα-acetyl-eglin C is recovered and the more hydrophilic side fractions are further purified by semipreparative reversed phase h.p.l.c. The experimental conditions are as follows:

Column: Vydac 218 TP510 (the separation group), size: 10×250 mm. Eluent: buffer A: 0,1 % trifluoroacetic acid, buffer B: Acetonitrile/Water 8:2+0.07 % trifluoroacetic acid. Gradient: 1 min 27 % buffer B, during 9,5 min increase to 46 % B, 20 min. isocrgtic, then increase in 7 min. to 60 % B, 4 min. isocratic, decrease in 2 min to initial condition. Flow 3 ml/min. AUFS: 4.0 at 220 nm back pressure: 130 bar, load: 4.0 mg per separation. 15 runs are performed.
Results:

| fraction | yield (mg) | FPLC[1] (NaCl) mM | HPLC[2] min. | HLE-inhibition |
|---|---|---|---|---|
| 2B | 3 | 0 | 20 | + |
| 4 | 3.4 | 55 | 23.6 | + |

-continued

| fraction | yield (mg) | FPLC[1]) (NaCl) mM | HPLC[2]) min. | HLE-inhi- bition |
|---|---|---|---|---|
| 6 | 2.5 | not tested | 28.8 | + |
| 8 | 18 | 65 | 37 | + |

[1])FPLC condition: column Mono Q; buffer A: 20 mM Tris.HCl pH 7.5; buffer B: 20 mM Tris.HCl pH 7.5, 500 mM NaCl; flow 1.5 ml/min; AUFS 0.05 (280 nm).
[2])retention time given in min.; conditions as above.

Characterization of the Fractions (cf. Example 27)

A) Fraction 2B a) Determination of the N-terminal amino acid: Phe b) Partial sequence analysis using a gas phase sequencer (Applied Biosystems) (200 pMol are applied)

Sequence found: PheGlySerGluLeuLysSerPhePro-GluValValGlyLysThrValAspGlnAlaArgGluTyrPheThrLeun.d-.Tyrn.d.n.d.TyrAspValn.d.Phe . . . (n.d.: not determined)

c) Peptide mapping using fast atom bombardmenrt (FAB-MS)

The molecular weights of the tryptic peptides found are as follows:

$T_1$ ("$A_3$–$A_8$") $M = 679$ $T_2$ ("$A_9$–$A_{16}$") $M = 861$ $T_3$ ("$A_{17}$–$A_{22}$") $M = 688$ $T_{4a}$ ("$A_{36}$–$A_{48}$") $M = 1442$ $T_7$ ("$A_{54}$–$A_{70}$") $M = 1848$ $A_3$ means amino acid 3 of natural eglin C etc.

d) Molecular weight determination by FAB-MS (details as in example 27d)

found: expected: molecular formula

MH$^+$ 7859.8 7861.9 $C_{364}H_{537}N_{94}O_{102}$ e) isoelectric point (pI): 6.8

According to the results obtained fraction 2B consists of Des [Thr$^1$, Glu$^2$]-eglin C, viz. eglin C lacking N-terminal amino acids 1 and 2.

B) Fraction 4 a) Determination of the N-terminal amino acid: Thr b) Partial sequence analysis using a gas phase sequencer (300 pMol are applied)

Sequence found: ThrGluPheGlySerGluLeuLysSerPheProGluValValGlyLysThrVal . . .

c) Peptide mapping by FAB-MS

The molecular weights of the tryptic peptides found are as follows:

$T_1$ ($A_1$–$A_8$) $M = 909$ $T_2$ ($A_9$–$A_{16}$) $M = 861$ $T_3$ ($A_{17}$–$A_{22}$) $M = 688$ $T_{4a}$ ($A_{36}$–$A_{48}$) $M = 1442$ $T_7$ ($A_{54}$–$A_{70}$) $M = 1848$ d) Molecular weight determination by FAB-MS (details as in example 27d)

found: expected: molecular formula

MH$^+$: 8091.48 8092.03 $C_{373}H_{551}N_{96}O_{107}$ e) Isoelectric point (pI): 6.5

Accordingly, the product of fraction 4 is eglin C.

C) Fraction 6 a) Determination of the N-terminal amino acid: Met b) Partial sequence analysis using a gas phase sequencer (200 pMoL are applied)

Sequence found: MetThrGluPheGlySerGluLeu-LysSerPheProGluValVaGyLysThrValn.d.Gln . . . (n.d.: not determined)

c) Peptide mapping by FAB-MS

The molecular weights of the tryptic peptides found are as follows:

$T_1$ ($A_1$–$A_9$) $M = 1040$ $T_2$ ($A_{10}$–$A_{17}$) $M = 861$ $T_3$ ($A_{18}$–$A_{23}$) $M = 688$ $T_4$ ($A_{24}$–$A_{49}$) $M = 3160$ $T_{4a}$ ($A_{37}$–$A_{49}$) $M = 1442$ $T_7$ ($A_{55}$–$A_{71}$) $M = 1848$ d) Molecular weight determination by FAB-MS (details as in example 27d)

found: expected: molecular formula

MH$^+$: 8223.5 8223.06 $C_{378}H_{560}N_{97}O_{108}S$ e) Isoelectric point (pI): 6.5

As evidenced by the analytical data, the product of fraction 6 is Nα-methionyl eglin C.

In analogous manner fraction 8 is subjected to partial sequence analysis, peptide mapping, FAB-MS and isoelectric focussing. The data reveals that the product of fraction 8 is Nα-acetyl-eglin C.

The amino acid compositions of all products analysed are determined. The results are consistent with the structures given.

The same products, eglin C, Nα-acetyl-eglin C, Nα-methionyl-eglin C and Des-eglin C are also detected in the harvest broths obtained from cultured E. coli HB 101/pML 147, E. coli LM 1035/pML 147/1 and E. coli JA 221/pML 147/1 cells.

Example 32

Synthesis of Modified Eglin C Compounds by E. coli HB101 Cells Transformed with the Plasmid pML147 (C') or pML147 (C")

The strains E. coli HB101 pML147 (C') and E. coli HB101 pML147 (C") are cultured as described in Example 22 and, after the cells have been broken down, the culture broth is purified by chromatography on an anhydrochymotrypsin column (cf. Example 25).

Two products (A and B) are isolated from the culture broth of *E. coli* HB101 pML147 (C') by HPLC separation (conditions: cf. Example 30). Product A has an $R_f$ value of 0.42 in disc electrophoresis (pH 8.9, 15% gel; corresponding to a Maurer system No. 2). Degradation with trypsin gives 7 fragments, 6 of which are identical to the fragments obtained by degradation of $N^\alpha$-acetyl-eglin C (cf. Example 27b). The 7th fragment, corresponding to the N-terminus of the peptide, consists of the sequence Ser-Glu-Leu-Lys, according to amino-acid sequence analysis by the method of Edman (33). Product A thus has the structure expected for eglin C':

SerGluLeuLysSerPheProGluValValGlyLysThrVal AspGlnAlaArg-GluTyrPheThrLeuHisTyrProGlnTyrAspValTyrPheLeuPro GluGlySerProValThrLeuAs-pLeuArgTyrAsnArgValArgValPheTyrAsnProGly ThrAsnValV-alAsnHisValProHisValGly.

On tryptic degradation, product B likewise gives 7 fragments. It differs from product A only in the N-terminal fragment, which carries an additional N-acetyl group on the serine radical and thus has the sequence N-acetyl-Ser-Glu-Leu-Lys. Product B is thus to be designated $N_\alpha$-acetyl-eglin C'.

Only one product (product C) can be identified from the broken down cells of the cultured *E. coli* HB101pML147 (C") cells, after chromatography on an anhydrochymotrypsin column and fine purification with HPLC. Product C has an $R_f$ value of 0.30 in disc electrophoresis (conditions as above). Tryptic degradation gives the dipeptide Leu-Lys as the N-terminal fragment; the remaining fragments are identical to the corresponding fragments isolated on tryptic degradation of $N^\alpha$-acetyl-eglin C. Product C thus has the structure expected for eglin C":

LeuLysSerPheProGluValValGlyLysThrVal AspGlnAlaArgGluTyr-PheThrLeuHisTyrProGlnTyrAspvalTyrPheLeuPro GluGlySer-ProValhrLeuAspLeuArgTyrAsnArgValArgValPheTyrAsnProGly ThrAsnValValAsnHisValProHisValGly.

Example 33

Enzymatic Synthesis of Nα-acetyl-eglin C 0.5 μmol of acetyl-coenzyme A and about 200 μg of an *E. coli* HB101 extract containing Nα-acetyl-transferase are added to 8 mg (1 μmol) of eglin C (obtained according to Example 26c with subsequent fine purification by HPLC) in a 0.06 M phosphate buffer, pH 7.5. Incubation is carried out at 37° C. After 3 hours, the enzyme is inactivated by heating at 60° C. and the mixture is subjected to HPLC purification. The Nα-acetyl-eglin C separated off is identical to the biosynthetic product (cf. Example 26c).

Example 34

Expression of Eglin in Yeast

An expression system for foreign genes in yeast requires a strong yeast promoter, preferably an inducible promoter, and a yeast transcription termination signal in a tandem array separated by unique restriction sites for the insertion of foreign genes. An expression vector also contains yeast DNA sequences that allow autonomous replication in yeast and lead to a high plasmid copy number. These sequences preferably are yeast 2μ sequences. The vector also has a yeast selectable marker, preferably the yeast LEU2 gene, as well as pBR322 DNA sequences with the origin of replication and the ampicillin resistance gene for amplification in *E. coli*. Such a vector is a "shuttle" vector for use in *E. coli* and yeast.

A suitable expression system, as described above, has been published in European Patent Application No. 100,561 and has been shown to be highly efficient in yeast. Foreign genes are expressed under the control of the inducible PH05 promoter of yeast acid phosphatase. PH05 promoter, foreign gene and PH05 transcription termination signals are inserted in a tandem array in plasmid pJDB207. It contains yeast 2μ sequences, the yeast LEU2 gene, the *E. coli* origin of replication and the ampicillin resistance gene.

The expression plasmid pJDB207R/PH05-EGL is constructed as follows:

a) Isolation of the pJDB207 Vector Fragment

Six μg of plasmid pJDB207R/IF (α-3) (EP 100,561) are digested to completion with restriction endonuclease BamHI. The resulting DNA fragments of 6.85 kb and 1,15 kb in size are precipitated by ethanol and resuspended in 400 μl of 50 mM Tris -HCL pH 8.0. 4.5 units of calf intestine alkaline phosphatase (Boehringer, Mannheim) are added. The mixture is incubated for 1 hour at 37° C. Subsequently, the phosphatase is inactivated by incubation at 65° C. for 1.5 hours. The solution is adjusted to 150 mM NaCl. The DNA solution is applied to a 100 μl bed of DE 52 (Whatman) anion exchanger equilibrated with 10 mM Tris-HCL pH 7,5 containing 150 mM NaCl and 1 mM EDTA. After washing with the same buffer, the DNA is eluted with 400 μl of 1.5 M NaCl, 10 mM Tris. HCL pH 7.5, 1 mM EDTA and precipitated by ethanol. The large 6.85 kb BamHI fragment is separated from the small fragment on a 0.6% Low melting agarose gel in Tris-borate-EDTA buffer pH 8.3.

b) Isolation of a 534 bp PH05 Promoter Fragment

Ten μg of plasmid p31/R (EP 100,561) are digested with restriction endonucleases EcoRI and BamHI. The resulting 3 fragments are separated on a 0.6% low melting agarose gel in Tris-borate-EDTA buffer pH 8.3. The 534 bp BamHI-EcoRI fragment is isolated which contains the PH05 promoter including the mRNA start sites.

c) Isolation of a 221 bp DNA Fragment Containing the Coding Sequence for Eglin

Eight μg of plasmid pML 147 are digested with restriction endonucleases BamHI and EcoRI. The resulting 2 DNA fragments are separated on a 0.6% low melting agarose gel in Tris-borate-EDTA buffer pH 8.3. The 221 bp fragment is isolated.

d) Ligation of DNA Fragments

Three DNA fragments described above (Example 34a–c) with appropriate sticky ends are Ligated in one reaction. 0.1 pmole (0.45 μg) of the 6.85 kb BamHI vector fragment, 0.2 pmole (70 ng) of the 534 bp BamHI-EcoRI PH05 promoter fragment and 0.2 pmole (29 ng) of the 221 bp EcoRI-BamHI fragment of pML 147 are ligated. All three DNA fragments are contained in small gel blocks of low melting agarose. The three pieces of agarose gel are pooled, liquified at 65° C. and diluted 2 times. The ligation is done in a total volume of 270 μl of 60 mM Tris-HCl pH 7.5, 10 mM MgCl$_2$, 10 mM DTT, 1 mM ATP with 16 units of T4 DNA ligase (Boehringer, Mannheim) at 15° C. for 16 hours. A 10 μl aliquot of the ligation mixture is added to 100 μl of calcium treated, transformation competent *E. coli* HB101 cells.

24 transformed, amp$^R$ colonies are grown individually in LB medium containing 100 μg/ml of ampicillin. Plasmid DNA is prepared according to the method of Holmes et al. (39) and is analysed by HindIII/EcoRI double digestion. The appearance of a 600 bp-EcoRI-HindIII fragment indicates that the particular clone has the PH05 promoter-eglin CDNA fragment inserted in the expression vector in the correct orientation. As expected, about 50% of the clones have an insert in the right orientation. One of these clones is isolated and referred to as pJDB207R/PH05-EGL.

e) Transformation of *Saccharomyces cerevisiae* GRF 18

Plasmid pJDB207R/PH05-EGL is introduced into *Saccharomyces cerevisiae* strain GRF18 (α, his3–11, his3–15, leu2–3, leu2–112, can$^R$) using the transformation protocol described by Hinnen et al. (4). Transformed yeast cells are selected on yeast minimal media plates deficient in leucine. Single transformed yeast colonies are isolated and referred to as *Saccharomyces cerevisiae* GRF18/pJDB207R/PH05-EGL.

f) Fermentation of *S. cerevisiae* GRF18/pJDB207R/PH05-EGL

Cells of *S. cerevisiae* GRF18/pJDB207R/PH05-EGL are grown in 300 ml of yeast minimal medium (Difco Yeast Nitrogen Base without amincacids to which 2% glucose and 20 mg/l L-histidine are added) in a 1 l Erlenmeyer flask with shaking at 30° C. for 24 hours to a density of $3 \times 10^7$ cells/ml. The cells are washed in 0,9% NaCl and used to inoculate 3 l of low $P_i$ minimal medium prepared according to the recipe of the Difco Yeast Nitrogen Base medium (without aminoacids) with 0.03 g/l KH$_2$PO$_4$, 1 g/l KCl, 10 g/l L-asparagine instead of (NH$_4$)$_2$SO$_4$, 2% glucose and 1 g/l L-histidine. The medium is inoculated to a starting OD$_{600}$ of 0.25. The cells are grown in a MBR Mini-Bioreactor at 300° C. for 24 hours with stirring at 500 rpm and harvested at an OD$_{600}$ of 1.9.

Example 35

Recovery of eglin C and Nα-acetyl-eglin C from Transformed *Saccharomyces cerevisiae* GRF 18/ pJDB 207R/PH05-EGL Both eglin C and Nα-acetyl-eglin C are recovered from *Saccharomyces cerevisiae* that has been transformed with a plasmid containing the eglin C structural gene. The products are expressed in a ratio of 2:1 (w/w) and with a yield of 15–20 mg per liter culture broth, based on reversed phase HPLC. The cells of *S. cerevisiae* are grown to a cell density (O.D.) of 1.9 at 600 nm as described in example 34f).

The 3 l harvest of the transformed yeast cells is cooled to 4° C. and centrifuged. The cells in the pellet are resuspended in 150 ml buffer and disrupted by glass beads. The homogenate is centrifuged and the supernatant diluted with an equal amount of 2% acetic acid. The suspension is centrifuged for 15 min. at 4000 rpm, the precipitate separated and the opaque supernatant again centrifuged for 60 min at 12,000 rpm. The clear supernatant is passed through a carboxymethylcellulose (CM) cationic exchange column (bed volume 32 ml) at pH 4 (1 bed volume starting buffer). Elution is carried out with a linear salt gradient of five bed volumes buffer A and five bed volumes buffer B (buffer A: 20 mM ammoniumacetate, pH 4.0; buffer B: 200 mM ammoniumacetate, pH 6.5; flow 43 ml per hour; fraction size: 14 ml). Nα-acetyl-eglin C is recovered in fractions 29–31 (15 mg) and further purified by semipreparative reversed phase HPLC, as described elsewhere (yield: 8 mg).

Eglin C is recovered in fractions 32–33 (24 mg), lyophilized and further purified by chromatography on a diethytaminoethylcellulose column (DE 53, Whatman, 32 ml bed volume) The product is dissolved in 15 ml starting buffer (pH 7.6 ) loaded and washed with one bed volume buffer A. More than 90% pure eglin C (based on total protein content) elutes between fractions 48–54 using a linear salt gradient. Pure fractions (based on isoelectric focussing) are pooled and three times lyophilized (yield 18 mg).

Both recovered eglins are assayed and chemically characterized as described above (Examples 27–30).

Results

| Eglin C | isoelectric point | 6.5 |
|---|---|---|
| | molecular weight (FAB-MS) | 8091 |
| | N-terminal amino acid | |
| | HLE inhibition | + |
| Nα-acetyl-eglin C | isoelectric point | 5.4 |
| | molecular weight (FAB-MS) | 8133 |
| | N-terminal amino acid | |
| | Nα-Acetyl-Thr | |
| | HLE inhibition | + |

Eglin C from transformed yeast has the same retention times on HPLC as observed for natural eglin C from Leech. Nα-acetyl-eglin C from transformed yeast comigrates with its counterpart from *E. coli*. The amino acid compositions and other data are as expected.

Example 36

Fermentation of *Saccharomyces cerevisiae* GRF 18/ pJDB 207R/PH05-EGL in a 30 l Fermenter The strain *Saccharomyces cerevisiae* GRF 18/pJDB 207 R/PH05-EGL is grown in the following growth medium (low P;) to a cell density (O.D.) of 1.87 at 600 nm (concentration in g or mg per 1 l solution):

| L-asparagine H$_2$O | 10 g |
|---|---|
| L-histidine | 1,0 g |
| KH$_2$PO$_4$ | 0,03 g |
| MgSO$_4$.7H$_2$O | 0,5 g |
| NaCl | 0,1 g |
| KCl | 1,0 g |
| CaCl$_2$.2H$_2$O | 0,1 g |
| cerelose (separately sterilized) | 20 g |
| boric acid | 50 mg |
| CuSO$_4$ | 5 mg |
| potassium iodide | 10 mg |
| FeCl$_3$ | 20 mg |
| MnSO$_4$ | 40 mg |
| sodium molybdate | 20 mg |
| ZnSO$_4$ | 40 mg |
| Ca-pantothenate | 40 mg |
| folic acid | 5 mg |
| inositol | 200 mg |
| nicotinic acid | 40 mg |
| para-amino-benzoicacid | 20 mg |
| pyridoxalphosphate | 40 mg |
| riboflavine | 20 mg |
| thiamine | 40 mg |
| biotine solution (10 mg/100 ml 50% ethanol) | |

Conditions: pH Control with NaOH; Lower Limit pH 4.6; Temperature 30° C.

Test samples (totally 8, of 100 ml culture broth) are taken every 6 hours, the cells are disrupted mechanically and after treatment with acetic acid the clear supernatants are assayed by RP-HPLC, PAGE and human leucocyte elastase (HLE)-inhibition.

After cultivation time of 36 hours optimal yields are obtained with 4.4 mg Nα-acetyl-eglin C and 13.6 mg eglin C per 1 l culture broth. The apparent molecular weights on PAGE are as expected.

The pH control with the lower limit at pH 5 and cultivation for 30 hours under the same conditions shifted the ratio between the two products towards eglin C (yield: 6.4 mg/l;

yield of Nα-acetyl-eglin C: 0.1 mg/l). Yeast eglin C and yeast Nα-acetyl-eglin C are recovered and purified to homogeneity as described in example 29.

Example 37

Purification of Nα-acetyl-eglin C by Free Flow Electrophoresis

Nα-acetyl-eglin C (1 g, material approximately 75% pure, based on RP-HPLC) is further purified using free flow zone-electrophoresis on a Elphor VAP 21 apparatus (Bender and Hobein, Munich, FRG). The experimental conditions are as follows: separation chamber 100×250×0.5 mm; buffer: ammoniumacetate/acetic acid pH 4.8. 1000 V/180 mA; temperature (chamber) 8° C.; duration 5 min.
Flow: 2 ml per hour, sample solution: 5% Nα-acetyl-eglin c in water. Essentially pure material eluted as samples 49–52 is collected, pooled and twice lyophilized (yield: 520 mg) Purity: >95% based on isotachophoresis, isoelectric focussing (pI 5.4) and reversed phase HPLC.

Example 38

Test Kit with Monoclonal Anti-eglin C Antibodies for the Determination of Eglin C, Competitive Radioimmunoassay A solution, prepared according to Example 24cC), of anti-eglin C antibodies is diluted with phosphate-buffered salt solution (PBS solution) to a concentration of 1 μg per 100 μl. 100 μl of this solution are incubated at 37° C. in plastic tubes or on plastic microtitre plates for 2 hours, antibodies being adsorbed non-specifically onto the surface of the plastic. For saturation of the active sites which are still free on the surface of the plastic, the plastic is after-treated with a bovine serum albumin solution (BSA solution).

In each case 50 μl of a solution of eglin C, Labelled in the known manner (20) with radioactive $^{125}$iodine and having an activity of 10,000 cpm per 50 μl are added to dilution series of a sample solution or of the standard solution in BSA solution, and the mixtures are then incubated on the surface of the plastic at 37° C. for 2 hours and subsequently at 4° C. for 12 hours. The tubes or microtitre plates are washed with phosphate-buffered salt solution and the radioactivity is measured. The concentration of eglin C in the sample solution is determined by means of a calibration curve measured with the standard solution.

A test kit for the radioimmunoassay described contains: 2 ml of solution of anti-eglin antibodies from Example 24cC) with a concentration of 1 to 10 mg per ml, 100 ml of phosphate-buffered salt solution (PBS solution), 100 ml of 0.3% bovine serum albumin and 0.1% sodium azide in PBS solution (BSA solution), 2 ml of solution of radioactive eglin C of activity 200,000 cpm/ml, 2 ml of standard solution containing 100 ng/ml of eglin C and 1 ml tubes or microtitre plates of plastic.

Example 39

Test Kit for Tandem ELISA with Monoclonal Anti-eglin C Antibodies 300 ng/depression of monoctonal antibodies 299S18-20, dissolved in sodium bicarbonate fixing buffer (pH 9.6) are fixed on microtitre plates by incubation at 4° C. overnight. The plates are washed three times with phosphate-buffered sodium chloride solution, containing 0.005% Tween 20 (H 7.2), and the depressions are then treated overnight at 4° C.
with 200 μl/depression of phosphate-buffered sodium chloride solution containing 0.2% of gelatine and 0.02% of sodium azide (PBS+gelatine+A). The plates are washed three times as before. Various concentrations of eglin C, diluted in PBS+gelatine+A, are added and the plates are incubated at room temperature for 4 hours. After washing three times as before, 100 μl/depression of a mixture of the second monoclonal antibody (299S22-1) coupled to alkaline phosphatase are added in an optimum titre (0.5 mg/ml of conjugate, diluted 1:200 for the test with PBS+gelatine+A) and the plates are incubated at room temperature for 2 hours, after which, after addition of 150 μl of p-nitrophenyl phosphate in diethanolamine buffer (pH 9.8), the colour is developed. The colour intensity ($OD_{405}$) is determined every 15 minutes for one hour using a Multiscan ELISA reading instrument.

The content of eglin C in the sample to be investigated is determined, by comparison of the $OD_{405}$ measured, with the aid of a calibration curve using known amounts of natural eglin C, for example from $10^1$ to $10^3$ ng/ml.

The method can also be used for the determination of eglin B or another eglin, for example Nα-acetyl-eglin C, and can also be used if the eglins to be determined are in plasma, for example in rat, cat or rabbit plasma.

A test kit for this tandem ELISA includes the reagents necessary for the test, in particular monoclonat anti-eglin antibodies, for example 299S18-20 and 299S22-1, if appropriate as a solution in the buffer to be used, the buffers to be used, including the substrate buffer, wash solutions, p-nitrophenyl phosphate, as the substrate, a standard solution containing the eglin to be determined, for example eglin C, a plastic microtitre plate, and/or, if appropriate, a table or calibration curve, for example the following, obtained according to the tandem ELISA described above:

|  | $OD_{405}$ |
|---|---|
| Natural eglin C (ng/ml) |  |
| $10^0$ | 0.09 |
| $10^1$ | 0.18 |
| $10^2$ | 0.73 |
| $10^3$ | 1.23 |
| Nα-Acetyl-eglin C (ng/ml) |  |
| $10^0$ | 0.08 |
| $10^1$ | 0.32 |
| $10^2$ | 1.00 |
| $10^3$ | 1.26 |

Example 40

Pharmaceutical Product Containing Nα-acetyl-eglin C for Parenteral Administration A solution containing Nα-acetyl-eglin C and prepared according to Example 24 or 25 is dialysed against 0.9% NaCl solution. The concentration of the solution is then brought to 1 mg/ml or 10 mg/ml by dilution with the same NaCl solution. These solutions are sterilised by ultrafiltration (membranes with 0.22 μm pores).

The sterilised solutions can be used directly for intravenous administration, for continuous* infusion and for misting in an inhalation apparatus (for example Bird).

The hybridoma cells which produce monoclonal anti-eglin antibodies and are obtained according to the invention were deposited in the "Collection Nationale de Cultures de Microorganismes" of the Pasteur Institute, Paris, France, on Nov. 6, 1984 under the following numbers:

| | |
|---|---|
| 299S18-20 | No. I-361 |
| 299S22-1 | No. I-362 |
| 299S22-10 | No. I-363 |

REFERENCES

1. U. Seemüller et al., Hoppe-Seyler's Z. Physiol. Chem. 358, 1105 (1977)
2. R. Knecht et al., Anal. Biochem. 130, 65 (1983)
3. A. M. Maxam and W. Gilbert, Proc. Natl. Acad. Sci. USA 74, 560 (1977); see also Meth. Enzym. 65, 499 (1980)
4. A. Hinnen et al., Proc. Natl. Acad. Sci. USA 75, 1929 (1978)
5. Anagnostopoulos et al., J. Bacteriol. 81, 741 (1961)
6. M. Mandel et al., J. Mol. Biol. 53, 159 (1970)
7. U. K. Laemmli, Nature 227, 680 (1970)
8. S. Tsunasawa and F. Sakiyama, in Methods Enzymol. 106, 165 (1984)
9. S. Alkan et al., Mol. Immunol. 20, 203 (1983)
10. T. Chard, An Introduction to Radioimmunoassay and related Techniques, North-Holland Publ. Comp., Amsterdam 1978
11. S. A. Narang, Tetrahedron 39, 3 (1983)
12. K. L. Agarwat et al., Angew. Chem. 84, 489 (1972)
13. C. B. Reese, Tetrahedron 34, 3143 (1972)
14. R. L. Letsinger and W. B. Lunsford, J. Am. Chem. Soc. 98, 3655 (1976)
15. K. Itakura et al., J. Am. Chem. Soc. 103, 706 (1981)
16. H. G. Khorana et al., J. Biol. Chem. 251, 565 (1976)
17. S. A. Narang et al., Anat. Biochem. 121, 356 (1982)
18. K. Itakura et al., J. Biol. Chem. 257, 9226 (1982)
19. Molecular Cloning, A Laboratory Manual (ed. T. Maniatis et al.), Cold Spring Harbor Lab., 1982, page 125
20. A. E. Bolton and W. M. Hunter, Biochem. J. 133, 529 (1973)
21. German Offentegungsschrift 3,111,405 (Genentech)
22. A. C. Peacock et al., Biochemistry 6, 1818 (1967)
23. W. Müller et al., J. Mol. Biol. 124, 343 (1978)
24. M. Grunstein and D. S. Hogness, Proc. Natl. Acad. Sci. USA 72, 3961 (1979)
25. Ish-Horowitz, in loc. cit. 19), page 368
26. Köhler and Milstein, Nature 256, 495 (1975)
27. H. Ako et al., Biochem. Biophys. Res. Comm., 46, 1639 (1972)
28. H. Fritz et al., in: "Methoden der enzymatischen Analyse" ("Methods of Enzymatic Analysis") (edited by H. U. Bergmeyer), 3rd edition, Weinheim 1974, page 1105
29. S. Moore et al., J. Biol. Chem. 192, 663 (1951), D. H. Spadman et al., Anal. Chem. 30, 1190 (1958)
30. H. Morris et al., Biochem. Biophys. Res. Comm. 117, 299 (1983)
31. U. Seemüller et al., Hoppe-Seyter's Z. Physiol. Chem. 361, 1841 (1980)
32. R. Knecht et al., Analyt. Biochem. 130, 65 (1983)
33. W. F. Brandt et al., Z. Physiol. Chem. 357, 1505 (1976)
34. A. Goldstein et al., Proc. Natl. Acad. Sci. USA 74, 725 (1977)
35. R. Wetzel and D. V. Goeddel, in "The Peptides" (edited by E. Gross and J. Meienhofer), Academic Press, New York 1983, pages 1–64
36. J. G. Bieth, Bull. europ. physiopath. respirat. 16 (suppl.), 183 (1980)
37. L. Clarke and J. Carbon, J. Mol. Biol. 120, 517 (1978)
38. D. S. Oppenheim and C. Yanofsky, J. Mol. Biol. 144, 143 (1980)
39. D. S. Holmes et al., Anal. Biochem. 114, 193 (1981)

What is claimed is:

1. A process for the preparation of an eglin compound having the following N-acetyl amino acid sequence:

N-acetyl-Thr-Glu-Phe-Gly-Ser-Glu-Leu-Lys-Ser-Phe-Pro-Glu-Val-Val-Gly-Lys-Thr-Val-Asp-Gln-Ala-Arg-Glu-Tyr-Phe-Thr-Leu-His-Tyr-Pro-Gln-Tyr-Asp-Val-W-Phe-Leu-Pro-Glu-Gly-Ser-Pro-Val-Thr-Leu-Asp-Leu-Arg-Tyr-Asn-Arg-Val-Arg-Val-Phe-Tyr-Asn-Pro-Gly-Thr-Asn-Val-Val-Asn-His-Val-Pro-His-Val-Gly (Formula XIV')

in which W is Tyr or His, said process comprising:

a) transforming host cells of *Escherichia coli* or *Saccharomyces cerevisiae* with an expression vector, said expression vector comprising a promoter of host cell origin and a DNA (sequence coding for said eglin compound, wherein said DNA sequence is directly and operably linked to and in proper reading frame relative to said promoter, in a liquid medium containing assimilable sources of carbon and nitrogen, b) culturing the transformed host cells in a liquid medium containing assimilable sources of carbon and nitrogen suitable for expression of said expression vector, and c) isolating said eglin compound.

2. A process according to claim 1 for the preparation of a compound of formula XIV', wherein W is Tyr.

3. A process according to claim 1 for the preparation of a compound of formula XIV', wherein W is His.

* * * * *

UNITED STATES PATENT AND TRADEMARK OFFICE
CERTIFICATE OF CORRECTION

PATENT NO. : 6,342,373 B1
DATED : January 29, 2002
INVENTOR(S) : Rink et al.

It is certified that error appears in the above-identified patent and that said Letters Patent is hereby corrected as shown below:

<u>Title page,</u>
Item [30], the Foreign Application Priority information should read:
-- [30]                 Foreign Application Priority Data
Nov. 21, 1983   (CH) ................................................ 6422/83
Apr. 13, 1984   (CH) ................................................ 1863/84
Nov. 12, 1984   (CH) ................................................ 5403/84

Signed and Sealed this

Eighteenth Day of June, 2002

*Attest:*

*Attesting Officer*

JAMES E. ROGAN
*Director of the United States Patent and Trademark Office*